(12) United States Patent
Choi et al.

(10) Patent No.: US 11,773,081 B2
(45) Date of Patent: Oct. 3, 2023

(54) PHARMACEUTICAL COMPOSITION FOR PREVENTING OR TREATING WOUND, COMPRISING INDIRUBIN DERIVATIVE AS ACTIVE INGREDIENT

(71) Applicant: CK Regeon Inc., Seoul (KR)

(72) Inventors: Kang-Yell Choi, Seoul (KR); Eunhwan Kim, Gyeonggi-do (KR); Seol Hwa Seo, Seoul (KR); Minguen Yoon, Seoul (KR)

(73) Assignee: CK REGEON INC., Seoul (KR)

( * ) Notice: Subject to any disclaimer, the term of this patent is extended or adjusted under 35 U.S.C. 154(b) by 0 days.

(21) Appl. No.: 18/046,536

(22) Filed: Oct. 14, 2022

(65) Prior Publication Data

US 2023/0105449 A1    Apr. 6, 2023

Related U.S. Application Data

(63) Continuation of application No. 16/973,646, filed as application No. PCT/KR2019/008235 on Jul. 4, 2019.

(30) Foreign Application Priority Data

Jul. 6, 2018 (KR) .................. 10-2018-0078585
Jul. 3, 2019 (KR) .................. 10-2019-0080244

(51) Int. Cl.

| | | |
|---|---|---|
| *C07D 403/04* | (2006.01) | |
| *A23L 33/105* | (2016.01) | |
| *A23L 33/00* | (2016.01) | |
| *A61K 8/9789* | (2017.01) | |
| *A61P 17/02* | (2006.01) | |
| *A61K 8/06* | (2006.01) | |
| *A61K 8/34* | (2006.01) | |
| *A61K 8/37* | (2006.01) | |
| *A61K 8/49* | (2006.01) | |
| *A61K 8/60* | (2006.01) | |
| *A61K 8/73* | (2006.01) | |
| *A61K 8/92* | (2006.01) | |
| *A61K 9/00* | (2006.01) | |
| *A61K 9/06* | (2006.01) | |
| *A61K 9/107* | (2006.01) | |
| *A61K 31/235* | (2006.01) | |
| *A61K 31/404* | (2006.01) | |
| *A61K 31/7048* | (2006.01) | |
| *A61K 36/754* | (2006.01) | |
| *A61K 47/10* | (2017.01) | |
| *A61K 47/26* | (2006.01) | |
| *A61K 47/40* | (2006.01) | |
| *A61K 47/44* | (2017.01) | |
| *A61Q 19/00* | (2006.01) | |

(52) U.S. Cl.
CPC .......... *C07D 403/04* (2013.01); *A23L 33/105* (2016.08); *A23L 33/40* (2016.08); *A61K 8/06* (2013.01); *A61K 8/345* (2013.01); *A61K 8/37* (2013.01); *A61K 8/492* (2013.01); *A61K 8/602* (2013.01); *A61K 8/604* (2013.01); *A61K 8/738* (2013.01); *A61K 8/922* (2013.01); *A61K 8/9789* (2017.08); *A61K 9/0014* (2013.01); *A61K 9/0056* (2013.01); *A61K 9/06* (2013.01); *A61K 9/107* (2013.01); *A61K 31/235* (2013.01); *A61K 31/404* (2013.01); *A61K 31/7048* (2013.01); *A61K 36/754* (2013.01); *A61K 47/10* (2013.01); *A61K 47/26* (2013.01); *A61K 47/40* (2013.01); *A61K 47/44* (2013.01); *A61P 17/02* (2018.01); *A61Q 19/00* (2013.01); *A23V 2002/00* (2013.01)

(58) Field of Classification Search
CPC .......... A61P 17/02; A61K 47/40; A61K 8/738
See application file for complete search history.

(56) References Cited

U.S. PATENT DOCUMENTS

2020/0179425 A1    6/2020    Choi

FOREIGN PATENT DOCUMENTS

| CN | 101284005 | 10/2008 |
|---|---|---|
| CN | 104055733 | 9/2014 |
| KR | 1020130103148 | 9/2013 |
| KR | 10-2015-0094900 | 8/2015 |

(Continued)

OTHER PUBLICATIONS

Partially translated pp. 6 and 16 of Lim, Jeong Ah, et al., "The Research on Skin Regeneration and Pharmaceutical Effects of Evodia Daniellii Hemsley", The 51st National Science Contest, 2005, pp. 1-43.

(Continued)

*Primary Examiner* — Qiuwen Mi
(74) *Attorney, Agent, or Firm* — DUANE MORRIS LLP; Gregory M. Lefkowitz

(57) ABSTRACT

The present disclosure relates to a composition for preventing or treating wound. The composition according to the present disclosure contains, as an active ingredient, an indirubin derivative alone or one or more selected from a group consisting of an indirubin derivative, an *Euodia sutchuenensis* Dode extract, methyl vanillate, hesperidin and quercitrin, and thus can be used as a pharmaceutical composition capable of promoting wound healing and reducing scarring not only in a normal state but also in a diabetic state. Furthermore, since the composition exhibits excellent effects in healing diabetic wound as well as general wound, it can be usefully used as a pharmaceutical composition, cosmetic composition or food composition for alleviating, preventing or treating general wound or diabetic wound, or as a veterinary composition for treating diabetic wound.

13 Claims, 21 Drawing Sheets

(56) References Cited

FOREIGN PATENT DOCUMENTS

| KR | 10-2016-0128764 | 11/2016 | | |
|---|---|---|---|---|
| KR | 10-1855423 | 5/2018 | | |
| KR | 10-2018-0119941 | 11/2018 | | |
| WO | 2005/041954 | 5/2005 | | |
| WO | WO-2005041954 A1 * | 5/2005 | ........... | A61K 31/404 |
| WO | 2008/070310 | 6/2008 | | |

OTHER PUBLICATIONS

Doersch, et al., "The impact of quercetin on wound healing relates to changes in $\alpha V$ and $\beta 1$ integrin expression", Exp Biol Med (Maywood), Aug. 2017, 242(14):1424-1431.

Jagetia, et al., "Topical Application of Hesperidin, a Citrus Bioflavanone Accelerates Healing of Full Thickness Dermal Excision Wounds in Mice Exposed to 6 Gy of Whole Body r-Radiation", Clin Res Dermatol Open Access 4(3):1-8.

Nam, et al., "Indirubin derivatives inhibit Stat3 signaling and induce apoptosis in human cancer cells." Proceedings of the Nation Academy of Sciences of the United States of America (2005), 102(17), 5998-6003.

Begum, et al., "An evaluation of indirubin analogues as phosphorylase kinase inhibitors," Journal of Molecular Graphics & Modeling (2015), 61, 231-242.

* cited by examiner

PHARMACEUTICAL COMPOSITION FOR PREVENTING OR TREATING WOUND, COMPRISING INDIRUBIN DERIVATIVE AS ACTIVE INGREDIENT

CROSS-REFERENCE TO RELATED APPLICATIONS

This application is a continuation of co-pending U.S. patent application Ser. No. 16/973,646, filed Dec. 9, 2020, which is a § 371 national stage entry of International Application No. PCT/KR2019/008235, filed on Jul. 4, 2019, which claims priority to Korean Patent Application No. 10-2018-0078585, filed on Jul. 6, 2018, and Korean Patent Application No. 10-2019-0080244, filed on Jul. 3, 2019, the entire contents of which are incorporated herein by reference.

TECHNICAL FIELD

The present disclosure relates to a composition for preventing or treating wound, more particularly to a pharmaceutical composition for preventing or treating wound, which contains an indirubin derivative as an active ingredient, and a cosmetic composition or food composition for preventing or treating wound, which contains the same.

BACKGROUND ART

Skin functions as a protective barrier that protects the body and can be seen as the first line of defense from microbial invasion, etc. Wound healing and recovery are the basis of tissue integrity and functional recovery after wound, burn, abrasion or other traumatic skin damages or surgical procedures. If wound healing is delayed or surgical wound opening occurs, significant clinical problems will occur.

At present, Dong Kook Pharm's 'Madecassol' (released in 1985) and Dong Wha Pharm's 'Fucidin' (released in 1980) are mainly used as wound healing agents in Korea. Although the two agents are generally similar in efficacy, Fucidin has a strong point in antibacterial activity whereas Madecassol is more effective in reducing scars.

The existing steroid ointments are effective in reducing inflammation, suppressing immunity, treating allergic diseases, etc., but they cause pockmarks, skin wrinkles, folliculitis, etc. as side effects and are not effective for bacterial diseases such as athlete's foot, etc. In addition, antibiotic-containing ointments may have resistance issues and may cause various side effects when used on wounds of children's soft skin. Therefore, wound healing agents based on wound healing mechanism are available on Korean market in order to overcome the limitations of steroid ointments or antibiotic ointments. Meanwhile, unlike ordinary skin wounds, severe accident wounds, large wounds occurring after surgery on skin diseases such as melanoma, wounds associated with other disease such as diabetes, etc. require long time for healing and often cause scars. Daewoong Pharmaceutical released 'EGF Saesal Yongo', which is the first over-the-counter wound healing agent containing epidermal growth factor (EGF) in Korea. The epidermal growth factor is helpful in preventing scars by promoting covering of the wound (re-epithelialization) and proliferation of granulation tissue. However, a lot of cost and effort are required for the production of the epidermal growth factor because it is a protein.

Use of stem cells for wound healing has been proposed to overcome these limitations. However, use of the stem cells as they are, has a risk of carcinogenesis due to DNA transfer and may cause vascular occlusion or myocardial infarction due to the large size of the stem cells themselves. And, transplantation using allogenic cells such as umbilical cord blood cells may cause rejection due to cell-surface antigens. In addition, the cell therapy agents such as stem cells have disadvantages in that the preparation procedure is complicated and there are a lot of limitations in storage and transportation. Therefore, a way capable of achieving the maximum therapeutic effect with minimum side effects, while resolving the fundamental problems of the cell therapy agents, is necessary.

The inventors of the present disclosure have made efforts to develop a wound healing agent with a generally mild mode of action and consistent and superior bioavailability with no side effect on the human body. As a result, they have invented a novel composition for preventing microbial infection at the wound site, healing wound and reducing scars (through re-epithelialization and proliferation of granulation tissue).

DISCLOSURE

Technical Problem

The present disclosure is directed to providing a pharmaceutical composition for preventing or treating wound, containing an indirubin derivative as an active ingredient, which has no side effect on the human body and exhibits superior wound healing effect.

The present disclosure is also directed to providing a pharmaceutical composition for a non-human animal for treating or alleviating diabetic wound, which contains one or more indirubin derivative selected from Chemical Formulas 1-4 as an active ingredient.

The present disclosure is also directed to providing a cosmetic composition for preventing or alleviating wound, which contains one or more indirubin derivative selected from Chemical Formulas 1-4 as an active ingredient.

The present disclosure is also directed to providing a food composition containing one or more indirubin derivative selected from Chemical Formulas 1-4 as an active ingredient.

The present disclosure is also directed to providing a method for treating wound by transdermally administering the composition to human or a non-human animal.

The present disclosure is also directed to providing a novel use of one or more indirubin derivative selected from Chemical Formulas 1-4 for preparation of a medication or a medication for an animal for treating wound.

Technical Solution

The present disclosure provides a pharmaceutical composition for preventing or treating wound, which contains one or more indirubin derivative selected from Chemical Formulas 1-4 as an active ingredient.

[Chemical Formula 1]

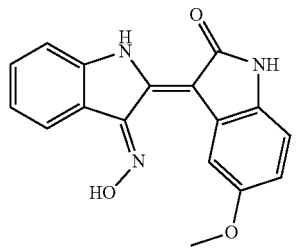

[Chemical Formula 2]

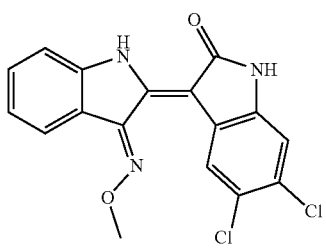

[Chemical Formula 3]

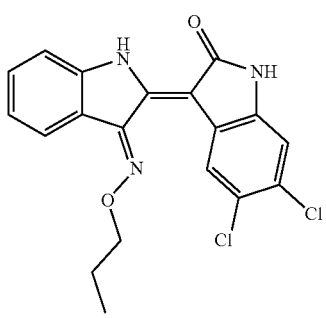

[Chemical Formula 4]

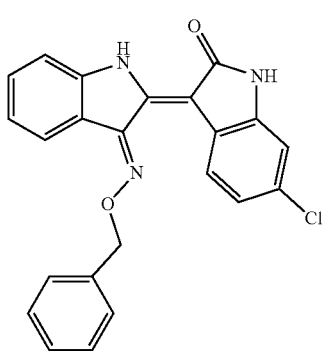

According to an exemplary embodiment of the present disclosure, the composition may further contain an *Euodia sutchuenensis* Dode extract or may further contain one or more selected from a group consisting of methyl vanillate, hesperidin and quercitrin.

According to an exemplary embodiment of the present disclosure, the wound may be caused by burn, ulcer, injury, surgical operation, childbirth, chronic wound, diabetic wound or dermatitis.

According to an exemplary embodiment of the present disclosure, the pharmaceutical composition may be for topical application to skin.

According to an exemplary embodiment of the present disclosure, the pharmaceutical composition may be prepared into a formulation selected from a group consisting of a cream, a gel, an ointment, an emulsion, a suspension, a spray and a transdermal patch.

According to an exemplary embodiment of the present disclosure, the composition may be an emulsion formulation further containing an oil, a surfactant and a polyethylene glycol.

According to an exemplary embodiment of the present disclosure, a mixing weight ratio of the oil, the surfactant and the polyethylene glycol may be 0.3-30:1:2-2.5.

According to an exemplary embodiment of the present disclosure, the active ingredient may be contained in an amount of 1-20 wt % based on the total weight of the composition.

According to an exemplary embodiment of the present disclosure, the surfactant may be one or more selected from a group consisting of polyoxyethylene sorbitan monolaurate (Tween 20), polyoxyethylene sorbitan monopalmitate (Tween 40), polyoxyethylene sorbitan monostearate (Tween 60) and polyoxyethylene sorbitan oleate (Tween 80).

According to an exemplary embodiment of the present disclosure, the oil may be one or more selected from a group consisting of polyethoxylated castor oil (Kolliphor® EL), sunflower oil and olive oil.

According to an exemplary embodiment of the present disclosure, the composition may further contain a cyclodextrin and the cyclodextrin may be contained in an amount of 100-1000 parts by weight based on 100 parts by weight of the active ingredient present in the composition.

The present disclosure also provides a pharmaceutical composition for a non-human animal for treating or alleviating wound, which contains one or more indirubin derivative selected from Chemical Formulas 1-4 as an active ingredient.

The present disclosure also provides a cosmetic composition for preventing or alleviating wound, which contains one or more indirubin derivative selected from Chemical Formulas 1-4 as an active ingredient.

[Chemical Formula 1]

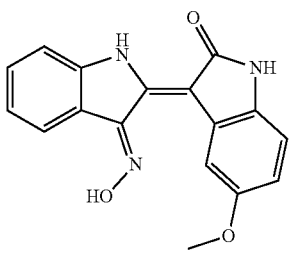

[Chemical Formula 2]

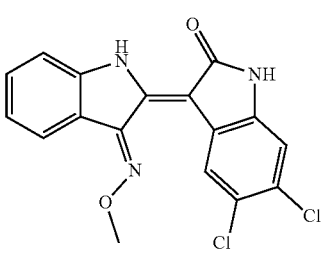

[Chemical Formula 3]

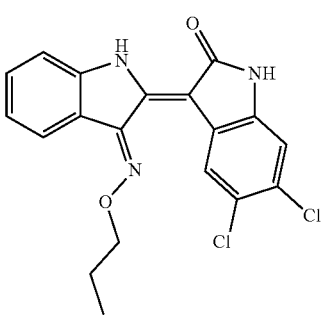

[Chemical Formula 4]

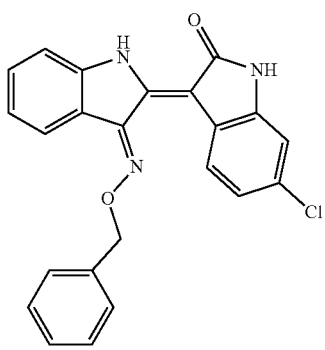

[Chemical Formula 1]

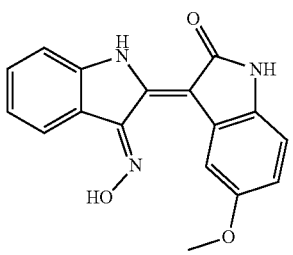

[Chemical Formula 2]

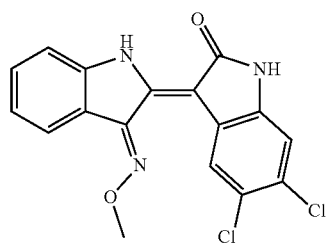

[Chemical Formula 3]

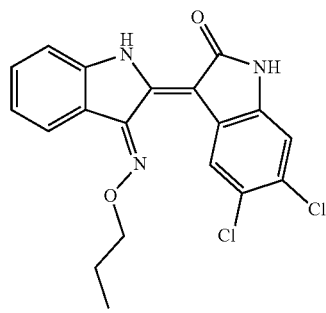

[Chemical Formula 4]

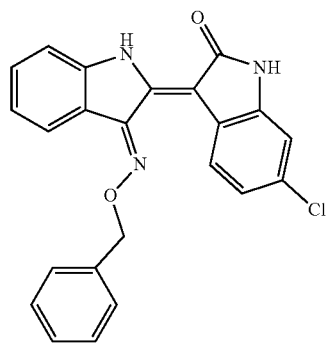

According to an exemplary embodiment of the present disclosure, the composition may further contain an *Euodia sutchuenensis* Dode extract or may further contain one or more selected from a group consisting of methyl vanillate, hesperidin and quercitrin.

According to an exemplary embodiment of the present disclosure, the cosmetic composition may be one selected from a group consisting of a toilet water, an essence, a lotion, a cream, a pack, a gel, a powder, a foundation and a cleanser.

According to an exemplary embodiment of the present disclosure, the composition may be an emulsion formulation further containing an oil, a surfactant and a polyethylene glycol.

According to an exemplary embodiment of the present disclosure, a mixing weight ratio of the oil, the surfactant and the polyethylene glycol may be 0.3-30:1:2-2.5.

According to an exemplary embodiment of the present disclosure, the active ingredient may be contained in an amount of 1-20 wt % based on the total weight of the composition.

According to an exemplary embodiment of the present disclosure, the surfactant may be one or more selected from a group consisting of polyoxyethylene sorbitan monolaurate (Tween 20), polyoxyethylene sorbitan monopalmitate (Tween 40), polyoxyethylene sorbitan monostearate (Tween 60) and polyoxyethylene sorbitan oleate (Tween 80).

According to an exemplary embodiment of the present disclosure, the oil may be one or more selected from a group consisting of polyethoxylated castor oil (Kolliphor® EL), sunflower oil and olive oil.

According to an exemplary embodiment of the present disclosure, the composition may further contain a cyclodextrin for better solubilization. The content of the cyclodextrin may be 100-1000 parts by weight based on 100 parts by weight of the active ingredient present in the composition.

The present disclosure also provides a food composition for preventing or alleviating wound, which contains one or more indirubin derivative selected from Chemical Formulas 1-4 as an active ingredient.

According to an exemplary embodiment of the present disclosure, the composition may further contain an *Euodia sutchuenensis* Dode extract or may further contain one or more selected from a group consisting of methyl vanillate, hesperidin and quercitrin.

Advantageous Effects

A composition containing one or more indirubin derivative selected from Chemical Formulas 1-4 as an active ingredient of the present disclosure promotes wound healing not only in a normal state but also in a diabetic state and exhibits superior effect of alleviating, preventing or treating wound including diabetic wound. Therefore, it can be usefully used as a pharmaceutical composition, cosmetic composition or food composition for alleviating, preventing or treating general wound or diabetic wound, or as a veterinary composition for treating diabetic wound.

In addition, an *Euodia sutchuenensis* Dode extract or methyl vanillate, hesperidin and quercitrin according to the present disclosure have little toxicity and provide better effect of wound recovery and healing, elasticity improvement, etc. when used together with the indirubin derivative, without exhibiting side effects on the human body unlike the existing steroid medications.

BEST MODE

Figure 1:
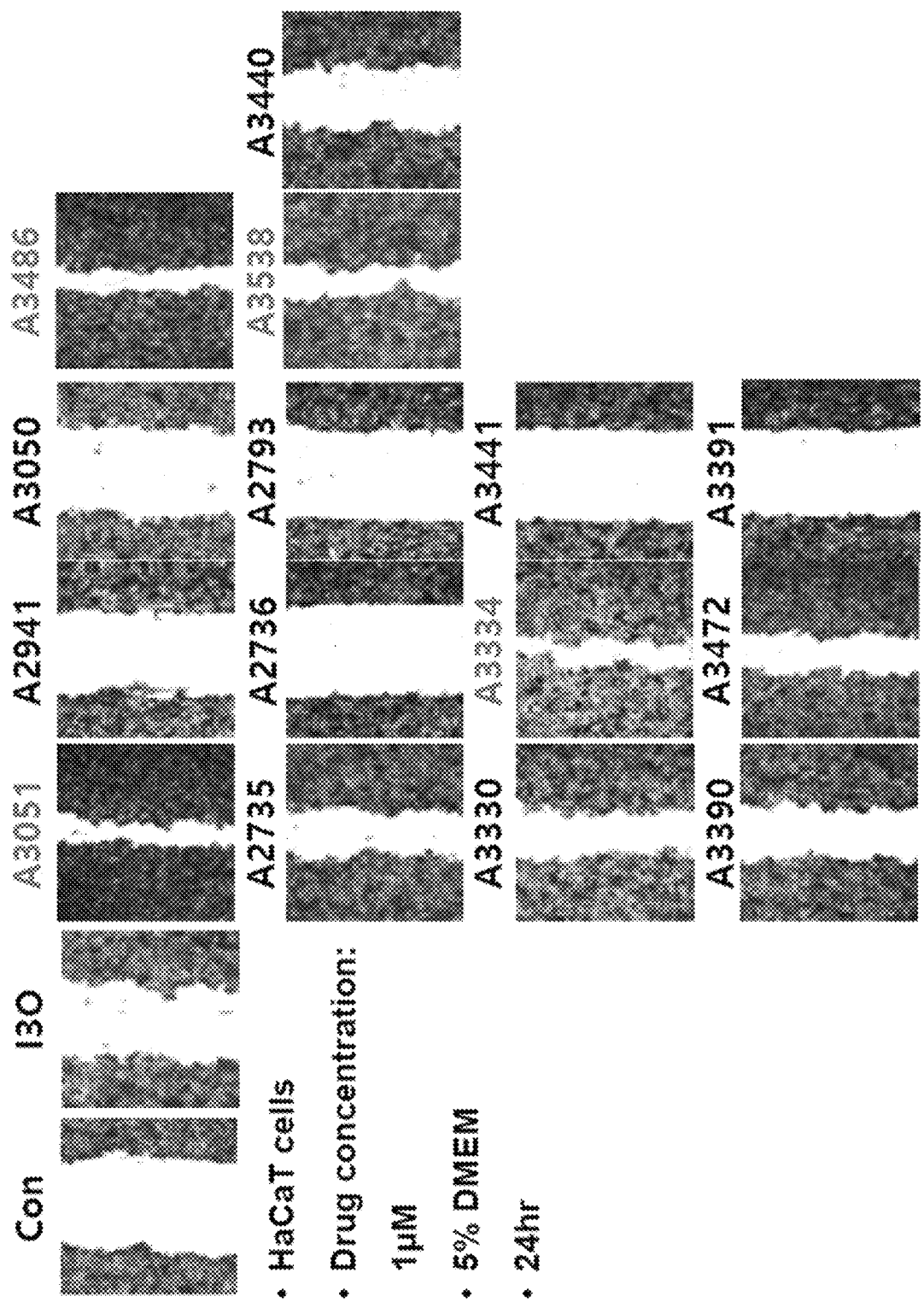
FIG. 1 shows the cell motility of keratinocytes depending on treatment with indirubin derivatives prepared in Examples 1-4 and Comparative Examples 1-12. The control group (con) means keratinocytes not treatment with an indirubin derivative.

Hereinafter, the present disclosure is described in detail.

The inventors of the present disclosure have made wound in a general animal model or a diabetes-induced animal model. Then, after dermally administering one or more indirubin derivative selected from Chemical Formulas 1-4 to the wound site, wound area, histological structure, collagen content, etc. were evaluated depending on time. As a result, the effect of healing wound and regenerating skin of the dermal administration of one or more indirubin derivative selected from Chemical Formulas 1-4 was confirmed.

The present disclosure also provides a pharmaceutical composition for preventing or treating wound, which contains one or more indirubin derivative selected from Chemical Formulas 1-4 as an active ingredient.

[Chemical Formula 1]

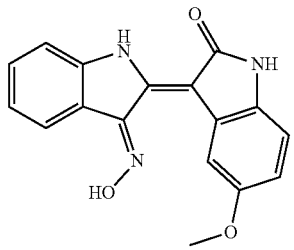

[Chemical Formula 2]

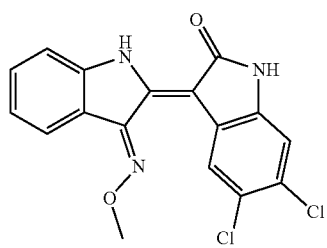

[Chemical Formula 3]

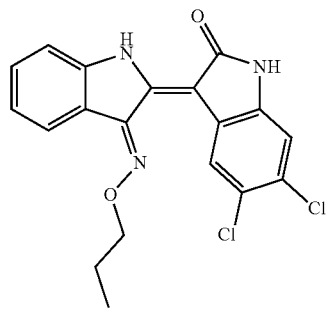

[Chemical Formula 4]

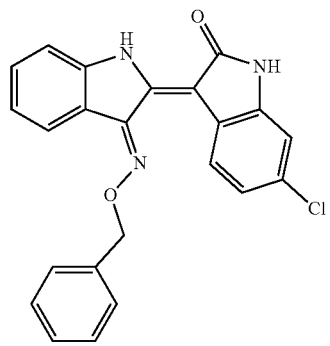

The one or more indirubin derivative selected from Chemical Formulas 1-4 is a substance which exhibits little cytotoxicity even when treated to cells for a long period of time. Because it exhibits excellent effect in regenerating cells, healing wound and producing collagen, it can be widely used for medications, foods, cosmetics, etc. having the function of preventing or treating wound. In addition, it was confirmed that, since the one or more indirubin derivative selected from Chemical Formulas 1-4 exhibits excellent effect in regenerating cells, healing wound and producing collagen for wound induced in diabetic state, it can be widely used for medications, foods, cosmetics, etc. having the function of preventing or treating diabetic wound.

There are various indirubin derivatives such as 5-methoxylindirubin-3'-oxime, 5-methoxylindirubin-3'-methoxime, indirubin-3'-oxime, 6-bromoindirubin-3'-oxime, 5,6-dichloroindirubin, 5,6-dichloroindirubin-3'-oxime, 5,6-dichloroindirubin-3'-methoxime, 5,6-dichloroindirubin-3'-propyloxime, 6-chloro-5-nitroindirubin, 6-chloro-5-nitroindirubin-3'-oxime, 6-chloroindirubin-3'-methoxime, 5-chloroindirubin-3'-methoxime, 5-bromoindirubin-3'-oxime, 5-bromoindirubin-3'-methoxime, 5-bromoindirubin-3'-ethyloxime, 5,6-dichloroindirubin-3'-oximepropyloxime, 6-chloroindirubin-3'-benzyloxime, etc. Among them, one or more indirubin derivative selected from Chemical Formulas 1-4 was confirmed to have the most superior effect of treating and healing wound.

Meanwhile, it was confirmed through in-vitro experiments that treatment with the one or more indirubin derivative selected from Chemical Formulas 1-4 improves wound closure rate (%), provides better wound healing effect (1.5-2.0 fold) and enables fastest wound healing as compared to other existing indirubin derivatives.

In addition, when one or more indirubin derivative selected from Chemical Formulas 1-4 was applied to the wound of mouse, it was confirmed that the acute wound of mouse was re-epithelialized comparably to or faster than the positive control group EGF and various wound healing markers of collagen tissue were increased. Specifically, an indirubin derivative of Chemical Formula 1 (A3334) showed slightly better wound repair effect than the positive control group EGF but was confirmed to be more effective in 'reducing scarring' as the epidermal layer of skin is repaired uniformly without remaining scars such as lump, recess, etc.

And, it was confirmed that an indirubin derivative of Chemical Formula 2 (A3051) exhibits 2-6 times better wound repair effect during the same period of time as compared to the positive control group EGF, suggesting that it can repair wound faster. In addition, it was confirmed that the epidermal layer is repaired cleanly and uniformly during wound healing without remaining scars such as lump, recess, etc. as compared to when treated with the positive control group EGF, suggesting that it is very effective in reducing scarring as compared to EGF.

That is to say, it was confirmed that the one or more indirubin derivative selected from Chemical Formulas 1-4 has an unexpectedly remarkable effect of reducing scarring by inducing uniform repair of the epidermal layer of skin, in addition to healing wound, unlike the existing wound healing agents or indirubin derivatives.

In diabetic state, wound healing is delayed significantly when wound such as ulcer, etc. occurs due to several causes, which was demonstrated through the test examples described later. It was confirmed that treatment with the one or more indirubin derivative selected from Chemical Formulas 1-4 provides an excellent effect of treating, alleviating or preventing diabetic wound as compared to the existing Wnt signaling pathway activator, VPA.

Accordingly, the one or more indirubin derivative selected from Chemical Formulas 1-4 according to the present disclosure can be used as a pharmaceutical composition, a cosmetic composition, etc. having an effect of treating wound including diabetic wound.

The composition according to the present disclosure maximizes cell motility and improves collagen production and accumulation in keratinocytes and fibroblasts, which play an important role in healing of wound induced in normal state or diabetic state.

Keratinocytes are the primary type of cells found in the epidermis. They constitute the basal layer of the epidermis, and form the outermost layer (horny layer, stratum corneum) through expansion and modification of the structure of keratinocytes until they form a cornified layer of mature cells on skin surface. The rate of wound healing is affected by the proliferation and migration speed of keratinocytes among other factors. It can be seen that the composition according to the present disclosure has an effective effect for wound healing since it increases the migration speed of keratinocytes. In addition, as described above, the composition according to the present disclosure has a scar-reducing effect of inducing repair of the epidermal layer of skin, in addition to superior wound healing effect. Considering that most wound healing agents are limited to wound treatment, scars formed during wound healing should be treated afterwards with scar-treating agents and wound treatment and scar treatment cannot be achieved simultaneously due to secondary problems such as inflammation, etc., a therapeutic agent having both wound-healing and scar-reducing effects will be very useful.

In other words, the composition according to the present disclosure may contain, among various existing indirubin derivatives, one or more indirubin derivative selected from Chemical Formulas 1-4, which exhibits remarkable effect of preventing or healing wound (about 2-fold), as an active ingredient (Test Example 1). As described above, the composition has advantages in that acute wound is re-epithelialized quickly and collagen production and accumulation are activated. In addition, it exhibits very remarkable wound healing effect by activating the migration and proliferation of fibroblasts.

The composition of the present disclosure may be a mixture further containing an *Euodia sutchuenensis* Dode extract and may be a mixture further containing one or more low-molecular-weight compound selected from a group consisting of methyl vanillate, hesperidin and quercitrin.

A mixture containing an *Euodia sutchuenensis* Dode extract and an indirubin derivative at a specific ratio exhibits excellent effect in wound healing. Specifically, it was confirmed through in-vitro experiments that wound closure rate (%) and wound healing effect are improved beyond a simple synergistic effect (2 fold) when treated together with the indirubin derivative and the extract, as compared to when treated with the one or more indirubin derivative selected from Chemical Formulas 1-4 alone.

In particular, as compared to when treated with the *Euodia sutchuenensis* Dode extract alone or with the indirubin derivative alone, about 1.5-2 times better result was achieved when treated with their mixture. That is to say, the composition for treating wound of the present disclosure provides a remarkable effect as compared to when the *Euodia sutchuenensis* Dode extract or the indirubin derivative is used alone, beyond the simple sum of the effects expected to be obtained from the respective compositions.

In addition, it was also confirmed through animal experiments that a mixture with the indirubin derivative has a remarkable effect as compared to the *Euodia sutchuenensis* Dode extract or the indirubin derivative alone.

The extract may be prepared from the stem, leaf, fruit, a pulverization product thereof or a mixture thereof of *Euodia sutchuenensis* Dode, as a raw material. The raw material may be extracted using a solvent selected from a group consisting of water, a $C_1$-$C_4$ anhydrous or water-containing lower alcohol, a mixture solvent of the lower alcohol and water, acetone, ethyl acetate, butyl acetate, chloroform and 1,3-butylene glycol as an extraction solvent.

The composition of the present disclosure may be a mixture further containing one or more low-molecular-weight compound selected from a group consisting of methyl vanillate, hesperidin and quercitrin. A mixture of the low-molecular-weight compound and the indirubin derivative at a specific ratio exhibits an excellent effect for wound healing. Specifically, it was confirmed through in-vitro experiments that when treated with the indirubin derivative together with one or more selected from a group consisting of methyl vanillate, hesperidin and quercitrin, wound closure rate (%) is improved, wound healing effect is improved beyond a simple synergistic effect (1.4-2.3 fold) and wound heals 6 hours faster as compared to when treated with the one or more indirubin derivative selected from Chemical Formulas 1-4 alone. In other words, it was confirmed through experiments that it is the most preferred use the indirubin derivative together with the one or more selected from a group consisting of methyl vanillate, hesperidin and quercitrin.

As demonstrated in the test examples described below, a mixture of the one or more low-molecular-weight compound selected from a group consisting of methyl vanillate, hesperidin and quercitrin and the one or more indirubin derivative selected from Chemical Formulas 1-4 recovered cell motility within 18 hours. In particular, a mixture of methyl vanillate and the indirubin derivative (A3051) showed 5 times better effect as compared to a non-treated control group.

The one or more low-molecular-weight compound selected from a group consisting of methyl vanillate, hesperidin and quercitrin is an ingredient included in an *Euodia sutchuenensis* Dode extract, a *Hovenia dulcis* extract, a tangerine extract, a *Polygonum aviculare* extract, a smartweed extract and a *Houttuynia cordata* extract. The extract is not specially limited as long as it is one extracted from the stem, leaf, fruit, a pulverization product thereof or a mixture thereof of one or more selected from *Euodia sutchuenensis* Dode, *Hovenia dulcis*, tangerine, *Polygonum aviculare*, smartweed and *Houttuynia cordata* as a raw material. Specifically, the raw material may be extracted using a solvent selected from a group consisting of water, a $C_1$-$C_4$ anhydrous or water-containing lower alcohol, a mixture solvent of the lower alcohol and water, acetone, ethyl acetate, butyl acetate, chloroform and 1,3-butylene glycol as an extraction solvent.

The methyl vanillate may exist mainly in the *Hovenia dulcis* extract, the hesperidin may exist mainly in the *Euodia sutchuenensis* Dode extract and the tangerine extract, and the quercitrin may exist mainly in the smartweed extract, the *Polygonum aviculare* extract and the *Houttuynia cordata* extract.

The indirubin derivative used in the present disclosure may be provided not only in free form but also as a pharmaceutically acceptable salt, pharmaceutically acceptable solvate, pharmaceutically acceptable polymorph or pharmaceutically acceptable prodrug thereof. The salt of the indirubin derivative is not specially limited as long as it can be mixed in a pharmaceutical or cosmetic composition. It includes an inorganic salt or an organic salt and can be an acidic salt or an alkaline salt. In particular, a cationic salt may be an alkali metal salt such as a sodium salt, a potassium salt, etc., an alkaline earth metal salt such as a calcium salt, a magnesium salt, a barium salt, etc., a basic amino acid salt such as arginine, lysine, etc., an ammonium salt such as an ammonium salt, a tricyclohexylammonium salt, etc., or an alkanolamine salt such as a monoethanolamine salt, a diethanolamine salt, a triethanolamine salt, a monoisopropanolamine salt, a diisopropanolamine salt, a triisopropanolamine salt, etc. The salt may be specifically an alkali metal salt, more specifically a tetrasodium salt.

Since the composition according to the present disclosure exhibits excellent effect of treating wound and reducing scarring, is capable of repairing cell damage and is capable of treating wound, repairing skin and reducing scarring, it can be usefully used to treat and prevent skin wound caused by, e.g., burn, ulcer, injury, surgical operation, childbirth, chronic wound, diabetic wound or dermatitis.

In the present disclosure, the "diabetic wound" refers to chronic wound occurring in patients with diabetes. The chronic wound refers to a wound the healing of which is delayed due to poor blood circulation cause by diabetes-induced peripheral vascular impairment.

Specifically, the diabetic wound may be caused by burn, ulcer, injury, surgical operation, plastic surgery, implantation, childbirth, chronic wound or dermatitis of the epidermal, dermal or subcutaneous tissue of skin occurring in diabetic state. More specifically, it may be caused by one or more selected from a group consisting of diabetic foot ulcer, diabetic angiopathy and diabetic foot infection. The composition of the present disclosure may be applied to a patch to be used as a medical device.

Specifically, the burn may be a burn caused by sunlight, chemicals, radiation or heat. Specifically, the ulcer may be diabetic ulcer. Specifically, the chronic wound may be bedsore or pressure ulcer. Specifically, the dermatitis may be one selected from a group consisting of impetigo, intertrigo, folliculitis and eczema, although not being limited thereto.

In the present disclosure, the term 'containing as an active ingredient' means an amount sufficient to treat wound on skin.

In the present disclosure, "alleviation" may refer to any action related with a parameter associated with the alleviation or treatment of a condition, e.g., decrease of the severity of a symptom, and "prevention" may refer to any action related with a parameter associated with the alleviation, treatment or delay of a condition, e.g., delay of the onset of a symptom.

In the composition, the indirubin derivative may be contained in an amount of 0.001-80 wt % based on the total weight of the composition. If the content is less than 0.01 wt %, a sufficient effect of preventing or healing wound may not be achieved. And, if it exceeds 80 wt %, skin irritation may be induced.

When the composition further contains an *Euodia sutchuenensis* Dode extract, a mixing weight ratio of the one or more indirubin derivative selected from Chemical Formulas 1-4 and the extract is not particularly limited. Specifically, 5-15 parts by weight of the indirubin derivative may be mixed based on 10 parts by weight of the extract based on dry weight. Outside this range, the increase in wound healing effect may be insignificant.

And, when the composition further contains one or more low-molecular-weight compound selected from a group consisting of methyl vanillate, hesperidin and quercitrin, a mixing weight ratio of the one or more indirubin derivative selected from Chemical Formulas 1-4 and the one or more low-molecular-weight compound selected from a group consisting of methyl vanillate, hesperidin and quercitrin is not particularly limited. Specifically, 1-20 mol of the indirubin derivative may be mixed based on 1 mol of the low-molecular-weight compound. Outside this range, the increase in wound healing effect may be insignificant.

The concentration of the *Euodia sutchuenensis* Dode extract or the low-molecular-weight compound in the composition is not particularly limited as long as it is one general in the art. The *Euodia sutchuenensis* Dode extract or the low-molecular-weight compound may be contained in an amount of 0.001-5 wt % based on dry weight or 0.001-50 wt % based on wet weight, based on the total weight of the composition. If the content is less than 0.01 wt %, a sufficient wound healing effect may not be achieved. And, if it exceeds 5 wt % (dry weight) or 50 wt % (wet weight), skin irritation may be induced.

The composition for preventing or treating wound of the present disclosure may be administered orally or parenterally. Parenteral administration may be achieved by intravenous injection, subcutaneous injection, intramuscular injection, intraperitoneal injection, dermal administration, transdermal administration, etc. Specifically, it may be achieved by dermal administration or transdermal administration.

The dosage of the pharmaceutical composition or medication may vary depending on the age, sex or body weight of a patient or an animal to be treated. Most importantly, it will depend on the condition of a subject to be treated, the specific category or type of a disease to be treated, administration route or the characteristics of the therapeutic agent.

The dosage of the pharmaceutical composition is selected adequately depending on the in-vivo absorption rate of the active ingredient, excretion rate, the age, body weight, sex and condition of a patient or subject to be treated, the severity of a disease to be treated, etc. In general, a daily dosage may be 0.1-1,000 mg/kg, specifically 1-500 mg/kg, more specifically 5-250 mg/kg, most specifically 10-100 mg/kg. If necessary, formulations prepared as unit dosage forms may be administered several times with given time intervals.

When the composition of the present disclosure is a composition for oral administration or injection, the composition according to the present disclosure may further contain a commonly used suitable carrier, excipient or diluent, and may be prepared into an oral formulation such as a powder, a granule, a tablet, a capsule, a suspension, an emulsion, a syrup, an aerosol, etc., a formulation for external application, a suppository or a sterilized solution for injection according to common methods.

The composition may be administered either alone or in combination with another therapeutic agent, as a medication for prevention or treatment. When administered in combination, it may be administered sequentially or simultaneously with another therapeutic agent.

The carrier, excipient or diluent that may be contained in the composition of the present disclosure may include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate and mineral oil.

In general, a formulation is prepared using a commonly used diluent or excipient such as a filler, an extender, a binder, a wetting agent, a disintegrant, a surfactant, etc. Solid formulations for oral administration include a tablet, a pill, a powder, a granule, a capsule, etc., and the solid formulation is prepared by mixing the composition of the present disclosure with at least one excipient, e.g., starch, calcium carbonate, sucrose, lactose, gelatin, etc. In addition to simple excipients, a lubricant such as magnesium stearate or talc is also used. Liquid formulations include a suspension, a liquid for internal use, an emulsion, a syrup, etc. In addition to a commonly used simple diluent such as water or liquid paraffin, the formulation may contain various excipients, e.g., a wetting agent, a sweetener, an aromatic, a preservative, etc. Formulations for parenteral administration include a sterilized aqueous solution, a non-aqueous solution, a suspension, an emulsion, a lyophilized formulation and a suppository. As the non-aqueous solution or suspension, propylene glycol, polyethylene glycol, vegetable oil such as olive oil, injectable ester such as ethyl oleate, etc. may be used. As a base of the suppository, witepsol, macrogol, Tween 61, cocoa butter, laurin butter, glycerogelatin, etc. may be used.

When the composition is formulated for parenteral administration into a liquid, a cream, a lotion, a gel or an aerosol, a common suitable additive, e.g., a preservative, a solvent which helps penetration of a medication, a softener in case of an ointment or a cream, etc. may be contained. A formulation for topical application may also contain a commonly used carrier, e.g., a cream or ointment base or ethanol or oleyl alcohol for a lotion. The carrier may constitute about 1-98% of a formulation, more generally, up to about 80% of a formulation.

The composition according to the present disclosure may be prepared into a formulation that can be applied or sprayed directly onto skin or wound, e.g., a cream, a lotion, an ointment, an aerosol, a gel or a pack. The ingredients suitable to be mixed in each formulation and methods for preparing the formulation are well known in the art. Those skilled in the art can adequately select the ingredients used for preparing common formulations for external application when preparing the formulation.

Such ingredients include, for an ointment, a cream, a gel, a lotion, etc., a base such as white petrolatum, yellow petrolatum, lanolin, white beeswax, cetanol, stearyl alcohol, stearic acid, hydrogenated oil, a gelled hydrocarbon, polyethylene glycol, liquid paraffin, squalane, etc., a solvent or solubilizer such as oleic acid, isopropyl myristate, glyceryl triisooctanoate, crotamiton, diethyl sebacate, diisopropyl adipate, hexyl laurate, a fatty acid, a fatty acid ester, an aliphatic alcohol, vegetable oil, etc., an antioxidant such as a tocopherol derivative, L-ascorbic acid, dibutylhydroxytoluene, butylhydroxyanisole, etc., a preservative such as p-hydroxybenzoic acid ester, etc., a humectant such as glycerin, propylene glycol, sodium hyaluronate, etc., a surfactant such as a polyoxyethylene derivative, glycerin fatty acid ester, sucrose fatty acid ester, sorbitan fatty acid ester, propylene glycol fatty acid ester, lecithin, etc., or a thickener such as carboxyvinyl polymer, xanthan gum, carboxymethyl cellulose, a carboxymethyl cellulose sodium salt, hydroxypropyl cellulose, hydroxypropylmethyl cellulose, etc.

For an aerosol formulation, in addition to the ingredients used for preparation of an ointment, a cream, a gel, a suspension, an emulsion, a liquid, a lotion, etc., a stabilizer, a buffer, a flavoring agent, a suspending agent, an emulsifying agent, an aromatic, a preservative, a solubilizer or other suitable additives may be mixed.

Specifically, the composition may also be prepared into an emulsion formulation containing an oil, a surfactant and a polyethylene glycol.

In the emulsion formulation, a mixing weight ratio of the oil, the surfactant and the polyethylene glycol may be 0.3-30:1:2-2.5, more specifically 10-20:1:2-2.5. The composition of the emulsion formulation may be determined by a pseudo-ternary phase diagram constructed according to a common method. Specifically, the pseudo-ternary phase diagram may be constructed by, after completely mixing an oil (polyethoxylated castor oil (Kolliphor® EL)) and a surfactant (e.g., a mixture of Tween 80 and a polyethylene glycol) at different mixing weight ratios within a specific range, plotting dots corresponding to an emulsion-forming region while adding water to the mixture of the oil and the surfactant. By determining an emulsion region from the constructed pseudo-ternary phase diagram and selecting a specific composition included in the region, the composition of an emulsion formulation in which the active ingredient (the indirubin derivative, or a mixture of the indirubin derivative and the *Euodia sutchuenensis* Dode extract or one or more selected from a group consisting of methyl vanillate, hesperidin and quercitrin) is dissolved can be determined.

Specifically, when the composition is an emulsion formulation, the active ingredient (the indirubin derivative, or a mixture of the indirubin derivative and the *Euodia sutchuenensis* Dode extract or one or more selected from a group consisting of methyl vanillate, hesperidin and quercitrin) may be contained in an amount of 1-20 wt % based on the total weight of the composition.

The surfactant is a Tween-based non-ionic surfactant and serves as a solubilizer. It is used as an emulsifier or a wetting agent in oral or parenteral pharmaceutical formulations and is also used in cosmetics or foods as an additive. In addition, it is used as a substance for inhibiting p-glycoprotein in order to increase the bioavailability of drugs. The Tween-based surfactant includes one or more selected from a group consisting of polyoxyethylene sorbitan monolaurate (Tween 20), polyoxyethylene sorbitan monopalmitate (Tween 40), polyoxyethylene sorbitan monostearate (Tween 60) and polyoxyethylene sorbitan oleate (Tween 80), although not being limited thereto. The Tween-based surfactant is approved by the US Food and Drug Administration for use in intravenous injection to human.

The polyethylene glycol is an amphiphilic polymer having both hydrophilicity and hydrophobicity. A polyethylene glycol with a small molecular weight is a liquid, but it becomes a solid as the molecular weight is increased. The polyethylene glycol may be one selected from a group consisting of PEG 150, 300, 400, 1000, 6000, 8000, 10000, 20000, 30000 and 40000. PEG 300 means a polyethylene glycol with a molecular weight of 300. A polyethylene glycol with a molecular weight exceeding 10,000 is also referred to as a polyethylene oxide (PEO). Among them, PEG 400 is in liquid state and is used frequently for solubilization of various poorly soluble drugs. In particular, it is a stable substance the oral and parenteral (intravenous injection, subcutaneous injection, intramuscular injection, etc.) use of which to human is approved by the US Food and Drug Administration (FDA).

In an exemplary embodiment of the present disclosure, the surfactant is polyoxyethylene sorbitan oleate (Tween 80) and the polyethylene glycol is PEG 400, which is amphiphilic, water-dispersible and non-ionic. Therefore, an emulsion formulation optimized for the poorly soluble active ingredient (the active ingredient including a mixture of one or more indirubin derivative of Chemical Formulas 1-4 and an *Euodia sutchuenensis* Dode extract or one or more low-molecular-weight compound selected from a group consisting of methyl vanillate, hesperidin and quercitrin) may be provided.

The oil may be one or more selected from a group consisting of polyethoxylated castor oil (Kolliphor® EL), sunflower oil and olive oil.

The composition may further contain a cyclodextrin for better solubilization. The cyclodextrin may be contained in an amount of 100-1000 parts by weight based on 100 parts by weight of the active ingredient present in the composition.

It was confirmed that the emulsion formulation is a stable formulation which does not show change in Wnt activity and solubility in distilled water at 4-25° C. for 3 months, capable of maintaining the activity of the active ingredient for a long period of time and effectively improving absorption into the body.

A method for preparing an emulsion composition for preventing or treating wound, which contains one or more indirubin derivative selected from Chemical Formulas 1-4 as an active ingredient, includes:

1) a step of preparing a first solution by mixing an oil, a surfactant and a polyethylene glycol;

2) a step of preparing a second solution containing one or more indirubin derivative selected from Chemical Formulas 1-4 as an active ingredient; and 3) a step of preparing an emulsion composition by mixing the first solution with the second solution.

The second solution may further contain an *Euodia sutchuenensis* Dode extract and one or more selected from a group consisting of methyl vanillate, hesperidin and quercitrin.

The second solution may further contain a cyclodextrin for better solubilization.

The polyethylene glycol is an amphiphilic polymer having both hydrophilicity and hydrophobicity. A polyethylene glycol with a small molecular weight is a liquid, but it becomes a solid as the molecular weight is increased. The polyethylene glycol may be one selected from a group consisting of PEG 150, 300, 400, 1000, 6000, 8000, 10000, 20000, 30000 and 40000. PEG 300 means a polyethylene glycol with a molecular weight of 300. A polyethylene glycol with a molecular weight exceeding 10,000 is also referred to as a polyethylene oxide (PEO). Among them, PEG 400 is in liquid state and is used frequently for solubilization of various poorly soluble drugs. In particular, it is a stable substance the oral and parenteral (intravenous injection, subcutaneous injection, intramuscular injection, etc.) use of which to human is approved by the US Food and Drug Administration (FDA).

The surfactant is a Tween-based non-ionic surfactant and serves as a solubilizer. It is used as an emulsifier or a wetting agent in oral or parenteral pharmaceutical formulations and is also used in cosmetics or foods as an additive. In addition, it is used as a substance for inhibiting p-glycoprotein in order to increase the bioavailability of drugs. The Tween-based surfactant includes one or more selected from a group consisting of polyoxyethylene sorbitan monolaurate (Tween 20), polyoxyethylene sorbitan monopalmitate (Tween 40), polyoxyethylene sorbitan monostearate (Tween 60) and polyoxyethylene sorbitan oleate (Tween 80), although not being limited thereto. The Tween-based surfactant is approved by the US Food and Drug Administration for use in intravenous injection to human.

A mixing weight ratio of the oil, the surfactant and the polyethylene glycol may be 0.3-30:1:2-2.5, more specifically 10-20:1:2-2.5. Specifically, when the composition is an emulsion formulation, the active ingredient (the indirubin derivative, or a mixture of the indirubin derivative and the *Euodia sutchuenensis* Dode extract or one or more selected from a group consisting of methyl vanillate, hesperidin and quercitrin) may be contained in an amount of 1-20 wt % based on the total weight of the composition.

When the emulsion composition of the present disclosure was observed with a microscope after adding water, the emulsion of the present disclosure was completely dissolved and an emulsion formulation (F8) in solution state was formed. As a result of observing the stability of the emulsion of the present disclosure, it was confirmed that nanosized spherical droplets with an average diameter of 20-1500 nm, specifically 30-50 nm, were formed and they showed a narrow size distribution.

In addition, it was confirmed that the emulsion of the present disclosure maintains stability for a long period of time, without change in the solubility or activity of the active ingredient at room temperature for 3 months. In addition, the emulsion formulation of the present disclosure can provide effectively improved absorption when administered orally or applied topically.

The present disclosure also provides a pharmaceutical composition for a non-human animal for preventing or alleviating wound, which contains one or more indirubin derivative selected from Chemical Formulas 1-4 as an active ingredient.

The present disclosure also provides a method for treating wound by transdermally administering the composition to human or a non-human animal.

The present disclosure also provides a novel use of one or more indirubin derivative selected from Chemical Formulas 1-4 for preparing a medication or a medication for an animal for treating wound.

Since the composition according to the present disclosure exhibits excellent effect of treating wound and reducing scarring, is capable of repairing cell damage and is capable of treating wound, repairing skin and reducing scarring, it can be usefully used to treat and prevent skin wound caused by, e.g., burn, ulcer, injury, surgical operation, childbirth, chronic wound, diabetic wound or dermatitis.

In the present disclosure, the "diabetic wound" refers to chronic wound occurring in patients with diabetes. The chronic wound refers to a wound the healing of which is delayed due to poor blood circulation cause by diabetes-induced peripheral vascular impairment.

Specifically, the diabetic wound may be caused by burn, ulcer, injury, surgical operation, plastic surgery, implantation, childbirth, chronic wound or dermatitis of the epidermal, dermal or subcutaneous tissue of skin occurring in diabetic state. More specifically, it may be caused by one or more selected from a group consisting of diabetic foot ulcer, diabetic angiopathy and diabetic foot infection. The composition of the present disclosure may be applied to a patch to be used as a medical device.

The 'medication', 'veterinary composition' or 'medication for an animal' may further contain, in addition to one or more indirubin derivative selected from Chemical Formulas 1-4 as an active ingredient, a suitable carrier, excipient or diluent commonly used for preparation of a pharmaceutical composition, etc.

The 'carrier' is a compound which makes delivery to a cell or a tissue easy. The 'diluent' is a compound dissolved in water in which a target compound is dissolved, which stabilizes a biologically active form of the target compound.

The carrier, excipient or diluent may be, for example, lactose, glucose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, etc., although not being specially limited thereto.

The dosage of the medication, veterinary composition or medication for an animal may vary depending on the age, sex or body weight of a patient or an animal to be treated. Most importantly, it will depend on the condition of a subject to be treated, the specific category or type of a disease to be treated, administration route or the characteristics of the therapeutic agent.

The dosage of the medication, veterinary composition or medication for an animal is selected adequately depending on the in-vivo absorption rate of the active ingredient, excretion rate, the age, body weight, sex and condition of a patient or subject to be treated, the severity of a disease to be treated, etc. In general, a daily dosage may be 0.1-1,000 mg/kg, specifically 1-500 mg/kg, more specifically 5-250 mg/kg, most specifically 10-100 mg/kg. If necessary, formulations prepared as unit dosage forms may be administered several times with given time intervals.

The medication, veterinary composition or medication for an animal may be administered either alone or in combination with another therapeutic agent, as a medication for prevention or treatment. When administered in combination, it may be administered sequentially or simultaneously with another therapeutic agent.

The medication, veterinary composition or medication for an animal may be prepared into an oral formulation such as a powder, granule, a tablet, a capsule, a troche, a suspension, an emulsion, a syrup, an aerosol, etc. according to common methods. The formulation may be prepared using a commonly used diluent or excipient such as a filler, an extender, a binder, a wetting agent, a disintegrant, a surfactant, etc.

For the formulation of the medication, veterinary composition or medication for an animal, the formulation of the pharmaceutical composition described above may be referred to.

The method for treating wound may include parenterally administering the composition to human or a non-human animal, particularly a mammal. For example, the composition may be administered dermally or transdermally to a subject to be treated in which wound is induced in normal or diabetic state.

For the administration dose, administration method and administration times for treatment, the administration dose, administration method and administration times of the pharmaceutical composition, medication, veterinary composition or medication for an animal described above may be referred to.

In another aspect, the present disclosure relates to a cosmetic composition for preventing or alleviating wound, which contains one or more indirubin derivative selected from Chemical Formulas 1-4 as an active ingredient.

[Chemical Formula 1]

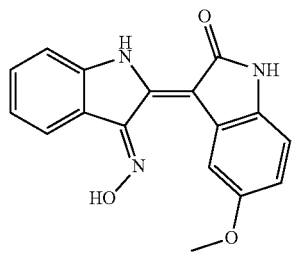

[Chemical Formula 2]

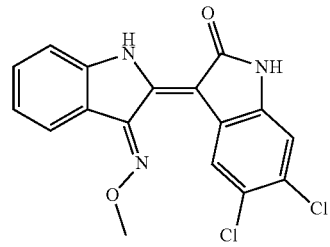

[Chemical Formula 3]

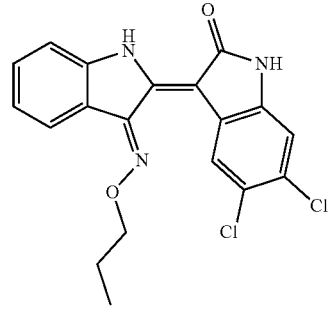

-continued

[Chemical Formula 4]

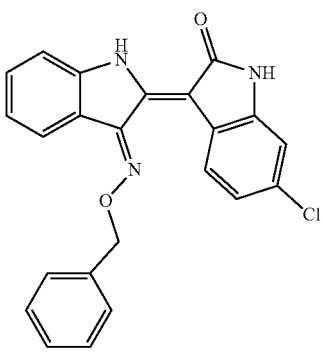

The indirubin derivative of the present disclosure is a substance which exhibits little cytotoxicity even when treated to cells for a long period of time. Because it exhibits excellent effect in regenerating cells, healing wound and producing collagen, it can provide cosmetic effect through prevention or treatment of wound. In addition, it was confirmed that, since the indirubin derivative exhibits excellent effect in regenerating cells, healing wound and producing collagen for wound induced in diabetic state, it can provide cosmetic effect through prevention or treatment of diabetic wound.

There are various indirubin derivatives such as 5-methoxylindirubin-3'-oxime, 5-methoxylindirubin-3'-methoxime, indirubin-3'-oxime, 6-bromoindirubin-3'-oxime, 5,6-dichloroindirubin, 5,6-dichloroindirubin-3'-oxime, 5,6-dichloroindirubin-3'-methoxime, 5,6-dichloroindirubin-3'-propyloxime, 6-chloro-5-nitroindirubin, 6-chloro-5-nitroindirubin-3'-oxime, 6-chloroindirubin-3'-methoxime, 5-chloroindirubin-3'-methoxime, 5-bromoindirubin-3'-oxime, 5-bromoindirubin-3'-methoxime, 5-bromoindirubin-3'-ethyloxime, 5,6-dichloroindirubin-3'-oximepropyloxime, 6-chloroindirubin-3'-benzyloxime, etc. Among them, one or more indirubin derivative selected from Chemical Formulas 1-4 was confirmed to have the most superior effect of treating and healing wound (Test Example 1).

Meanwhile, it was confirmed through in-vitro experiments that treatment with the one or more indirubin derivative selected from Chemical Formulas 1-4 improves wound closure rate (%), provides better wound healing effect (1.5-2.0 fold) and enables fastest wound healing as compared to other existing indirubin derivatives.

In addition, when one or more indirubin derivative selected from Chemical Formulas 1-4 was applied to the wound of mouse, it was confirmed that the acute wound of mouse was re-epithelialized comparably to or faster than the positive control group EGF and various wound healing markers of collagen tissue were increased. Specifically, an indirubin derivative of Chemical Formula 1 (A3334) showed slightly better wound repair effect than the positive control group EGF but was confirmed to be more effective in 'reducing scarring' as the epidermal layer of skin is repaired uniformly without remaining scars such as lump, recess, etc.

And, it was confirmed that an indirubin derivative of Chemical Formula 2 (A3051) exhibits 2-6 times better wound repair effect during the same period of time as compared to the positive control group EGF, suggesting that it can repair wound faster. In addition, it was confirmed that the epidermal layer is repaired cleanly and uniformly during wound healing without remaining scars such as lump, recess, etc. as compared to when treated with the positive control group EGF, suggesting that it is very effective in reducing scarring as compared to EGF.

That is to say, it was confirmed that the one or more indirubin derivative selected from Chemical Formulas 1-4 has an unexpectedly remarkable effect of reducing scarring by inducing uniform repair of the epidermal layer of skin, in addition to healing wound, unlike the existing wound healing agents or indirubin derivatives.

In diabetic state, wound healing is delayed significantly when wound such as ulcer, etc. occurs due to several causes, which was demonstrated through the test examples described later.

It was confirmed that treatment with the one or more indirubin derivative selected from Chemical Formulas 1-4 provides an excellent effect of treating, alleviating or preventing diabetic wound as compared to the existing Wnt signaling pathway activator, VPA.

Accordingly, the one or more indirubin derivative selected from Chemical Formulas 1-4 according to the present disclosure can be used as a cosmetic composition having an effect of treating wound including diabetic wound.

The composition according to the present disclosure maximizes cell motility and improves collagen production and accumulation in keratinocytes and fibroblasts, which play an important role in healing of wound induced in normal state or diabetic state.

In the composition, the indirubin derivative may be contained in an amount of 0.001-80 wt % based on the total weight of the composition. If the content is less than 0.01 wt %, a sufficient effect of preventing or healing wound may not be achieved. And, if it exceeds 80 wt %, skin irritation may be induced.

The composition of the present disclosure may be a mixture further containing an *Euodia sutchuenensis* Dode extract and may be a mixture further containing one or more low-molecular-weight compound selected from a group consisting of methyl vanillate, hesperidin and quercitrin.

A mixture of the *Euodia sutchuenensis* Dode extract and the indirubin derivative at a specific ratio exhibits an excellent effect for wound healing. Specifically, it was confirmed through in-vitro experiments that when treated with the indirubin derivative and the extract together, wound closure rate (%) is improved and wound healing effect is improved beyond a simple synergistic effect (2 fold) as compared to when treated with the one or more indirubin derivative selected from Chemical Formulas 1-4 alone.

In particular, about 1.5-2.0 fold better result was achieved when threated with the mixture as compared to when threated with the *Euodia sutchuenensis* Dode extract alone or when threated with the indirubin derivative alone. That is to say, the composition for treating wound of the present disclosure provides a remarkable effect as compared to when the *Euodia sutchuenensis* Dode extract or the indirubin derivative is used alone, beyond the simple sum of the effects expected to be obtained from the respective compositions.

In addition, it was also confirmed through animal experiments that a mixture with the indirubin derivative has a remarkable effect as compared to the *Euodia sutchuenensis* Dode extract or the indirubin derivative alone.

The extract may be prepared from the stem, leaf, fruit, a pulverization product thereof or a mixture thereof of *Euodia sutchuenensis* Dode, as a raw material. The raw material may be extracted using a solvent selected from a group consisting of water, a $C_1$-$C_4$ anhydrous or water-containing lower alcohol, a mixture solvent of the lower alcohol and water, acetone, ethyl acetate, butyl acetate, chloroform and 1,3-butylene glycol as an extraction solvent.

The composition of the present disclosure may be a mixture further containing one or more low-molecular-weight compound selected from a group consisting of methyl vanillate, hesperidin and quercitrin. A mixture of the low-molecular-weight compound and the indirubin derivative at a specific ratio exhibits an excellent effect for wound healing. Specifically, it was confirmed through in-vitro experiments that when treated with the indirubin derivative together with one or more selected from a group consisting of methyl vanillate, hesperidin and quercitrin, wound closure rate (%) is improved, wound healing effect is improved beyond a simple synergistic effect (1.4-2.3 fold) and wound heals 6 hours faster as compared to when treated with the one or more indirubin derivative selected from Chemical Formulas 1-4 alone. In other words, it was confirmed through experiments that it is the most preferred use the indirubin derivative together with the one or more selected from a group consisting of methyl vanillate, hesperidin and quercitrin.

As demonstrated in the test examples described below, a mixture of the one or more low-molecular-weight compound selected from a group consisting of methyl vanillate, hesperidin and quercitrin and the one or more indirubin derivative selected from Chemical Formulas 1-4 recovered cell motility within 18 hours. In particular, a mixture of methyl vanillate and the indirubin derivative (A3051) showed 5 times better effect as compared to a non-treated control group.

The one or more low-molecular-weight compound selected from a group consisting of methyl vanillate, hesperidin and quercitrin is an ingredient included in an *Euodia sutchuenensis* Dode extract, a *Hovenia dulcis* extract, a tangerine extract, a *Polygonum aviculare* extract, a smartweed extract and a *Houttuynia cordata* extract. The extract is not specially limited as long as it is one extracted from the stem, leaf, fruit, a pulverization product thereof or a mixture thereof of one or more selected from *Euodia sutchuenensis* Dode, *Hovenia dulcis*, tangerine, *Polygonum aviculare*, smartweed and *Houttuynia cordata* as a raw material. Specifically, the raw material may be extracted using a solvent selected from a group consisting of water, a $C_1$-$C_4$ anhydrous or water-containing lower alcohol, a mixture solvent of the lower alcohol and water, acetone, ethyl acetate, butyl acetate, chloroform and 1,3-butylene glycol as an extraction solvent.

The methyl vanillate may exist mainly in the *Hovenia dulcis* extract, the hesperidin may exist mainly in the *Euodia sutchuenensis* Dode extract and the tangerine extract, and the quercitrin may exist mainly in the smartweed extract, the *Polygonum aviculare* extract and the *Houttuynia cordata* extract.

When the composition further contains an *Euodia sutchuenensis* Dode extract, a mixing weight ratio of the one or more indirubin derivative selected from Chemical Formulas 1-4 and the extract is not particularly limited. Specifically, 5-15 parts by weight of the indirubin derivative may be mixed based on 10 parts by weight of the extract based on dry weight. Outside this range, the increase in wound healing effect may be insignificant.

And, when the composition further contains one or more low-molecular-weight compound selected from a group consisting of methyl vanillate, hesperidin and quercitrin, a mixing weight ratio of the one or more indirubin derivative selected from Chemical Formulas 1-4 and the one or more low-molecular-weight compound selected from a group consisting of methyl vanillate, hesperidin and quercitrin is not particularly limited. Specifically, 1-20 mol of the indirubin derivative may be mixed based on 1 mol of the low-molecular-weight compound. Outside this range, the increase in wound healing effect may be insignificant.

The concentration of the *Euodia sutchuenensis* Dode extract or the low-molecular-weight compound in the composition is not particularly limited as long as it is one general in the art. The *Euodia sutchuenensis* Dode extract or the low-molecular-weight compound may be contained in an amount of 0.001-5 wt % based on dry weight or 0.001-50 wt % based on wet weight, based on the total weight of the composition. If the content is less than 0.01 wt %, a sufficient wound healing effect may not be achieved. And, if it exceeds 5 wt % (dry weight) or 50 wt % (wet weight), skin irritation may be induced.

The cosmetic composition according to the present disclosure may further contain an additive capable of enhancing cosmetic effect by alleviating wound, although not being specially limited thereto.

The cosmetic composition according to the present disclosure may be a mixture further containing an *Euodia sutchuenensis* Dode extract, may be a mixture further containing one or more low-molecular-weight compound selected from a group consisting of methyl vanillate, hesperidin and quercitrin.

The cosmetic composition according to the present disclosure may be prepared into a toilet water, an essence, a lotion, a cream, a pack, a gel, a powder, a foundation or a cleanser formulation. For example, it may be prepared into a toilet water, a nourishing lotion, a nourishing essence, a massage cream, a cosmetic bath additive, a body lotion, a body milk lotion, a bath oil, a baby oil, a baby powder, a shower gel, a shower cream, a sunscreen lotion, a sunscreen cream, a suntan cream, a skin lotion, a skin cream, an anti-UV cosmetic, a cleansing milk, a cosmetic hair remover, a facial/body lotion, a facial/body cream, a skin-whitening cream, a hand cream, a hair lotion, a cosmetic cream, jasmine oil, a bath soap, a liquid soap, a beauty soap, a shampoo, a hand cleaner, a medicated soap not for medical use, a cream soap, a facial wash, a body cleanser, a scalp cleanser, a hair rinse, a toilet soap, a tooth-whitening gel, a toothpaste, etc. For this, the composition of the present disclosure may further contain a solvent commonly used for preparation of a cosmetic composition or a suitable carrier, excipient or diluent.

The solvent that may be further added in the cosmetic composition of the present disclosure is not specially limited. For example, water, saline, DMSO or a combination thereof may be used. The carrier, excipient or diluent may include purified water, an oil, a wax, a fatty acid, a fatty acid alcohol, a fatty acid ester, a surfactant, a humectant, a thickener, an antioxidant, a viscosity stabilizer, a chelating agent, a buffer, a lower alcohol, etc., although not being limited thereto. In addition, a skin-whitening agent, a moisturizer, a vitamin, anti-UV agent, a perfume, a dye, an antibiotic, an antibacterial agent or an antifungal agent may be included, if necessary.

The oil may be hydrogenated vegetable oil, castor oil, cottonseed oil, olive oil, palm kernel oil, jojoba oil or avocado oil, and the wax may be beeswax, spermaceti, carnauba, candelilla wax, montan wax, ceresin, liquid paraffin or lanolin.

The fatty acid may be stearic acid, linoleic acid, linolenic acid or oleic acid, the fatty acid alcohol may be cetyl alcohol, octyldodecanol, oleyl alcohol, panthenol, lanolin alcohol, stearyl alcohol or hexadecanol, and the fatty acid ester may be isopropyl myristate, isopropyl palmitate or butyl stearate. And, the surfactant may be a cationic surfactant, an anionic surfactant or a non-ionic surfactant known in the art. Specifically, a surfactant derived from a natural substance may be used.

In addition, various humectants, thickeners, antioxidants, etc. widely known in the cosmetic industry may also be used with amounts known in the art.

Specifically, the cosmetic composition of the present disclosure may be an emulsion formulation further containing an oil, a surfactant and a polyethylene glycol.

In the emulsion formulation, a mixing weight ratio of the oil, the surfactant and the polyethylene glycol may be 0.3-30:1:2-2.5, more specifically 10-20:1:2-2.5. The composition of the emulsion formulation may be determined by a pseudo-ternary phase diagram constructed according to a common method. Specifically, the pseudo-ternary phase diagram may be constructed by, after completely mixing an oil (polyethoxylated castor oil (Kolliphor® EL)) and a surfactant (e.g., a mixture of Tween 80 and a polyethylene glycol) at different mixing weight ratios within a specific range, plotting dots corresponding to an emulsion-forming region while adding water to the mixture of the oil and the surfactant. By determining an emulsion region from the constructed pseudo-ternary phase diagram and selecting a specific composition included in the region, the composition of an emulsion formulation in which the active ingredient (the indirubin derivative, or a mixture of the indirubin derivative and the *Euodia sutchuenensis* Dode extract or one or more selected from a group consisting of methyl vanillate, hesperidin and quercitrin) is dissolved can be determined.

Specifically, when the composition is an emulsion formulation, the active ingredient (the indirubin derivative, or a mixture of the indirubin derivative and the *Euodia sutchuenensis* Dode extract or one or more selected from a group consisting of methyl vanillate, hesperidin and quercitrin) may be contained in an amount of 1-20 wt % based on the total weight of the composition.

The surfactant is a Tween-based non-ionic surfactant and serves as a solubilizer. It is used as an emulsifier or a wetting agent in oral or parenteral pharmaceutical formulations and is also used in cosmetics or foods as an additive. In addition, it is used as a substance for inhibiting p-glycoprotein in order to increase the bioavailability of drugs. The Tween-based surfactant includes one or more selected from a group consisting of polyoxyethylene sorbitan monolaurate (Tween 20), polyoxyethylene sorbitan monopalmitate (Tween 40), polyoxyethylene sorbitan monostearate (Tween 60) and polyoxyethylene sorbitan oleate (Tween 80), although not being limited thereto. The Tween-based surfactant is a stable substance which is approved by the US Food and Drug Administration for use in intravenous injection to human.

The polyethylene glycol is an amphiphilic polymer having both hydrophilicity and hydrophobicity. A polyethylene glycol with a small molecular weight is a liquid, but it becomes a solid as the molecular weight is increased. The polyethylene glycol may be one selected from a group consisting of PEG 150, 300, 400, 1000, 6000, 8000, 10000, 20000, 30000 and 40000. PEG 300 means a polyethylene glycol with a molecular weight of 300. A polyethylene glycol with a molecular weight exceeding 10,000 is also referred to as a polyethylene oxide (PEO). Among them, PEG 400 is in liquid state and is used frequently for solubilization of various poorly soluble drugs. In particular, it is a stable substance the oral and parenteral (intravenous injection, subcutaneous injection, intramuscular injection, etc.) use of which to human is approved by the US Food and Drug Administration (FDA).

In an exemplary embodiment of the present disclosure, the surfactant is polyoxyethylene sorbitan oleate (Tween 80) and the polyethylene glycol is PEG 400, which is amphiphilic, water-dispersible and non-ionic. Therefore, an emulsion formulation optimized for the poorly soluble active ingredient (the active ingredient including a mixture of one or more indirubin derivative of Chemical Formulas 1-4 and an *Euodia sutchuenensis* Dode extract or one or more low-molecular-weight compound selected from a group consisting of methyl vanillate, hesperidin and quercitrin) may be provided.

The oil may be one or more selected from a group consisting of polyethoxylated castor oil (Kolliphor® EL), sunflower oil and olive oil.

The composition may further contain a cyclodextrin for better solubilization. The cyclodextrin may be contained in an amount of 100-1000 parts by weight based on 100 parts by weight of the active ingredient present in the composition.

It was confirmed that the emulsion formulation is a stable formulation which does not show change in Wnt activity and solubility in distilled water at 4-25° C. for 3 months, capable of maintaining the activity of the active ingredient for a long period of time and effectively improving absorption into the body.

A method for preparing an emulsion cosmetic composition for preventing or alleviating wound, which contains one or more indirubin derivative selected from Chemical Formulas 1-4 as an active ingredient, includes:

1) a step of preparing a first solution by mixing an oil, a surfactant and a polyethylene glycol;

2) a step of preparing a second solution containing one or more indirubin derivative selected from Chemical Formulas 1-4 as an active ingredient; and 3) a step of preparing an emulsion composition by mixing the first solution with the second solution.

The second solution may further contain an *Euodia sutchuenensis* Dode extract and one or more selected from a group consisting of methyl vanillate, hesperidin and quercitrin.

The second solution may further contain a cyclodextrin for better solubilization.

The polyethylene glycol is an amphiphilic polymer having both hydrophilicity and hydrophobicity. A polyethylene glycol with a small molecular weight is a liquid, but it becomes a solid as the molecular weight is increased. The polyethylene glycol may be one selected from a group consisting of PEG 150, 300, 400, 1000, 6000, 8000, 10000, 20000, 30000 and 40000. PEG 300 means a polyethylene glycol with a molecular weight of 300. A polyethylene glycol with a molecular weight exceeding 10,000 is also referred to as a polyethylene oxide (PEO). Among them, PEG 400 is in liquid state and is used frequently for solubilization of various poorly soluble drugs. In particular, it is a stable substance the oral and parenteral (intravenous injection, subcutaneous injection, intramuscular injection, etc.) use of which to human is approved by the US Food and Drug Administration (FDA).

The surfactant is a Tween-based non-ionic surfactant and serves as a solubilizer. It is used as an emulsifier or a wetting agent in oral or parenteral pharmaceutical formulations and is also used in cosmetics or foods as an additive. In addition, it is used as a substance for inhibiting p-glycoprotein in order to increase the bioavailability of drugs. The Tween-based surfactant includes one or more selected from a group consisting of polyoxyethylene sorbitan monolaurate (Tween 20), polyoxyethylene sorbitan monopalmitate (Tween 40), polyoxyethylene sorbitan monostearate (Tween 60) and polyoxyethylene sorbitan oleate (Tween 80), although not being limited thereto. The Tween-based surfactant is a stable substance which is approved by the US Food and Drug Administration for use in intravenous injection to human.

A mixing weight ratio of the oil, the surfactant and the polyethylene glycol may be 0.3-30:1:2-2.5, more specifically 10-20:1:2-2.5. Specifically, when the composition is an emulsion formulation, the active ingredient (the indirubin derivative, or a mixture of the indirubin derivative and the *Euodia sutchuenensis* Dode extract or one or more selected from a group consisting of methyl vanillate, hesperidin and quercitrin) may be contained in an amount of 1-20 wt % based on the total weight of the composition.

When the emulsion composition of the present disclosure was observed with a microscope after adding water, the emulsion of the present disclosure was completely dissolved and an emulsion formulation (F8) in solution state was formed. As a result of observing the stability of the emulsion of the present disclosure, it was confirmed that nanosized spherical droplets with an average diameter of 20-1500 nm, specifically 30-50 nm, were formed and they showed a narrow size distribution.

In addition, it was confirmed that the emulsion of the present disclosure maintains stability for a long period of time, without change in the solubility or activity of the active ingredient at room temperature for 3 months. In addition, the emulsion formulation of the present disclosure can provide effectively improved absorption when administered orally or applied topically.

In another aspect, the present disclosure relates to a food composition for preventing or alleviating wound, which contains one or more indirubin derivative selected from Chemical Formulas 1-4 as an active ingredient.

[Chemical Formula 1]

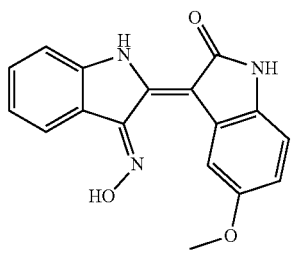

[Chemical Formula 2]

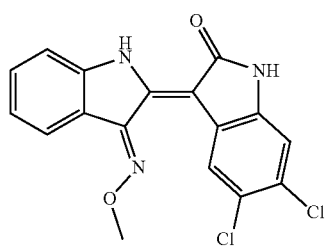

[Chemical Formula 3]

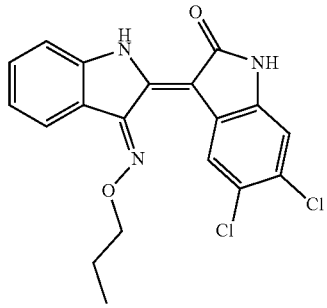

[Chemical Formula 4]

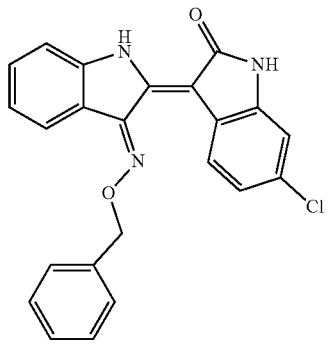

The one or more indirubin derivative selected from Chemical Formulas 1-4 is a substance which exhibits little cytotoxicity even when treated to cells for a long period of time. Because it exhibits excellent effect in regenerating cells, healing wound and producing collagen, it can be widely used for medications, foods, cosmetics, etc. having the function of preventing or treating wound. In addition, it was confirmed that, since the one or more indirubin derivative selected from Chemical Formulas 1-4 exhibits excellent effect in regenerating cells, healing wound and producing collagen for wound induced in diabetic state, it can be widely used for medications, foods, cosmetics, etc. having the function of preventing or treating diabetic wound.

There are various indirubin derivatives such as 5-methoxylindirubin-3'-oxime, 5-methoxylindirubin-3'-methoxime, indirubin-3'-oxime, 6-bromoindirubin-3'-oxime, 5,6-dichloroindirubin, 5,6-dichloroindirubin-3'-oxime, 5,6-dichloroindirubin-3'-methoxime, 5,6-dichloroindirubin-3'-propyloxime, 6-chloro-5-nitroindirubin, 6-chloro-5-nitroindirubin-3'-oxime, 6-chloroindirubin-3'-methoxime, 5-chloroindirubin-3'-methoxime, 5-bromoindirubin-3'-oxime, 5-bromoindirubin-3'-methoxime, 5-bromoindirubin-3'-ethyloxime, 5,6-dichloroindirubin-3'-oximepropyloxime, 6-chloroindirubin-3'-benzyloxime, etc. Among them, one or more indirubin derivative selected from Chemical Formulas 1-4 was confirmed to have the most superior effect of treating and healing wound.

Meanwhile, it was confirmed through in-vitro experiments that treatment with the one or more indirubin derivative selected from Chemical Formulas 1-4 improves wound closure rate (%), provides better wound healing effect (1.5-2.0 fold) and enables fastest wound healing as compared to other existing indirubin derivatives.

In addition, when one or more indirubin derivative selected from Chemical Formulas 1-4 was applied to the wound of mouse, it was confirmed that the acute wound of mouse was re-epithelialized comparably to or faster than the positive control group EGF and various wound healing markers of collagen tissue were increased. Specifically, an indirubin derivative of Chemical Formula 1 (A3334) showed slightly better wound repair effect than the positive control group EGF but was confirmed to be more effective in reducing scarring as the epidermal layer of skin is repaired uniformly without remaining scars such as lump, recess, etc.

And, it was confirmed that an indirubin derivative of Chemical Formula 2 (A3051) exhibits 2-6 times better wound repair effect during the same period of time as compared to the positive control group EGF, suggesting that it can repair wound faster. In addition, it was confirmed that the epidermal layer is repaired cleanly and uniformly during wound healing without remaining scars such as lump, recess, etc. as compared to when treated with the positive control group EGF, suggesting that it is very effective in reducing scarring as compared to EGF. That is to say, it was confirmed that the one or more indirubin derivative selected from Chemical Formulas 1-4 has an unexpectedly remarkable effect of reducing scarring by inducing uniform repair of the epidermal layer of skin, in addition to healing wound, unlike the existing wound healing agents or indirubin derivatives.

In diabetic state, wound healing is delayed significantly when wound such as ulcer, etc. occurs due to several causes, which was demonstrated through the test examples described later.

It was confirmed that treatment with the one or more indirubin derivative selected from Chemical Formulas 1-4 provides an excellent effect of treating, alleviating or preventing diabetic wound as compared to the existing Wnt signaling pathway activator, VPA.

The composition according to the present disclosure maximizes cell motility and improves collagen production and accumulation in keratinocytes and fibroblasts, which play an important role in healing of wound induced in normal state or diabetic state.

The composition of the present disclosure may be a mixture further containing an *Euodia sutchuenensis* Dode extract and may be a mixture further containing one or more low-molecular-weight compound selected from a group consisting of methyl vanillate, hesperidin and quercitrin.

A mixture of the *Euodia sutchuenensis* Dode extract and the indirubin derivative at a specific ratio exhibits an excellent effect for wound healing. Specifically, it was confirmed through in-vitro experiments that when treated with the indirubin derivative and the extract together, wound closure rate (%) is improved and wound healing effect is improved beyond a simple synergistic effect (2 fold) as compared to when treated with the one or more indirubin derivative selected from Chemical Formulas 1-4 alone.

In particular, about 1.5-2.0 fold better result was achieved when threated with the mixture as compared to when threated with the *Euodia sutchuenensis* Dode extract alone or when threated with the indirubin derivative alone. That is to say, the composition for treating wound of the present disclosure provides a remarkable effect as compared to when the *Euodia sutchuenensis* Dode extract or the indirubin derivative is used alone, beyond the simple sum of the effects expected to be obtained from the respective compositions.

In addition, it was also confirmed through animal experiments that a mixture with the indirubin derivative has a remarkable effect as compared to the *Euodia sutchuenensis* Dode extract or the indirubin derivative alone.

The extract may be prepared from the stem, leaf, fruit, a pulverization product thereof or a mixture thereof of *Euodia sutchuenensis* Dode, as a raw material. The raw material may be extracted using a solvent selected from a group consisting of water, a $C_1$-$C_4$ anhydrous or water-containing lower alcohol, a mixture solvent of the lower alcohol and water, acetone, ethyl acetate, butyl acetate, chloroform and 1,3-butylene glycol as an extraction solvent.

The composition of the present disclosure may be a mixture further containing one or more low-molecular-weight compound selected from a group consisting of methyl vanillate, hesperidin and quercitrin. A mixture of the low-molecular-weight compound and the indirubin derivative at a specific ratio exhibits an excellent effect for wound healing. Specifically, it was confirmed through in-vitro experiments that when treated with the indirubin derivative together with one or more selected from a group consisting of methyl vanillate, hesperidin and quercitrin, wound closure rate (%) is improved, wound healing effect is improved beyond a simple synergistic effect (1.4-2.3 fold) and wound heals 6 hours faster as compared to when treated with the one or more indirubin derivative selected from Chemical Formulas 1-4 alone. In other words, it was confirmed through experiments that it is the most preferred use the indirubin derivative together with the one or more selected from a group consisting of methyl vanillate, hesperidin and quercitrin.

As demonstrated in the test examples described below, a mixture of the one or more low-molecular-weight compound selected from a group consisting of methyl vanillate, hesperidin and quercitrin and the one or more indirubin derivative selected from Chemical Formulas 1-4 recovered cell motility within 18 hours. In particular, a mixture of methyl vanillate and the indirubin derivative (A3051) showed 5 times better effect as compared to a non-treated control group.

The one or more low-molecular-weight compound selected from a group consisting of methyl vanillate, hesperidin and quercitrin is an ingredient included in an *Euodia sutchuenensis* Dode extract, a *Hovenia dulcis* extract, a tangerine extract, a *Polygonum aviculare* extract, a smartweed extract and a *Houttuynia cordata* extract. The extract is not specially limited as long as it is one extracted from the stem, leaf, fruit, a pulverization product thereof or a mixture thereof of one or more selected from *Euodia sutchuenensis* Dode, *Hovenia dulcis*, tangerine, *Polygonum aviculare*, smartweed and *Houttuynia cordata* as a raw material. Specifically, the raw material may be extracted using a solvent selected from a group consisting of water, a $C_1$-$C_4$ anhydrous or water-containing lower alcohol, a mixture solvent of the lower alcohol and water, acetone, ethyl acetate, butyl acetate, chloroform and 1,3-butylene glycol as an extraction solvent.

The methyl vanillate may exist mainly in the *Hovenia dulcis* extract, the hesperidin may exist mainly in the *Euodia sutchuenensis* Dode extract and the tangerine extract, and the quercitrin may exist mainly in the smartweed extract, the *Polygonum aviculare* extract and the *Houttuynia cordata* extract.

When the composition further contains an *Euodia sutchuenensis* Dode extract, a mixing weight ratio of the one or more indirubin derivative selected from Chemical Formulas 1-4 and the extract is not particularly limited. Specifically, 5-15 parts by weight of the indirubin derivative may be mixed based on 10 parts by weight of the extract based on dry weight. Outside this range, the increase in wound healing effect may be insignificant.

And, when the composition further contains one or more low-molecular-weight compound selected from a group consisting of methyl vanillate, hesperidin and quercitrin, a mixing weight ratio of the one or more indirubin derivative selected from Chemical Formulas 1-4 and the one or more low-molecular-weight compound selected from a group consisting of methyl vanillate, hesperidin and quercitrin is not particularly limited. Specifically, 1-20 mol of the indirubin derivative may be mixed based on 1 mol of the low-molecular-weight compound. Outside this range, the increase in wound healing effect may be insignificant.

The concentration of the *Euodia sutchuenensis* Dode extract or the low-molecular-weight compound in the composition is not particularly limited as long as it is one general in the art. The *Euodia sutchuenensis* Dode extract or the low-molecular-weight compound may be contained in an amount of 0.001-5 wt % based on dry weight or 0.001-50 wt % based on wet weight, based on the total weight of the composition. If the content is less than 0.01 wt %, a sufficient wound healing effect may not be achieved. And, if it exceeds 5 wt % (dry weight) or 50 wt % (wet weight), skin irritation may be induced.

The food composition of the present disclosure may be prepared into various foods, for example, a beverage, gum, tea, a vitamin complex, a powder, granule, a tablet, a capsule, confectionery, a rice cake, bread, etc. Since the food composition of the present disclosure is prepared from a plant extract with little toxicity and few side effects, it can be safely used for a long period of time for the purpose of prevention.

When the indirubin derivative of the present disclosure is contained in the food composition, it may be added at a ratio of 0.001-80% based on total weight.

When the food composition is prepared as a beverage, there is no special limitation. Like common beverages, it may further contain additional ingredients such as various flavoring agents, natural carbohydrates, etc. The natural carbohydrate may include a monosaccharide such as glucose, etc., a disaccharide such as fructose, etc., a polysaccharide such as sucrose, etc., a common sugar such as a dextrin, a cyclodextrin, etc., a sugar alcohol such as xylitol, sorbitol, erythritol, etc., or the like. The flavoring agent may include a natural flavoring agent (thaumatin, stevia extract (e.g., rebaudioside A, glycyrrhizin, etc.), a synthetic flavoring agent (saccharin, aspartame, etc.), etc.

In addition, the food composition of the present disclosure may contain various nutrients, vitamins, minerals (electrolytes), flavoring agents such as synthetic flavoring agents, natural flavoring agents, etc., colorants, pectic acid and its salts, alginic acid and its salts, organic acids, protective colloidal thickeners, pH control agents, stabilizers, antiseptics, glycerin, alcohols, carbonating agents used in carbonated beverages, etc.

These ingredients may be used either alone or in combination. Although the proportion of the additives is not an important factor in the present disclosure, it is generally selected from a range of about 0.1-50 parts by weight based on 100 parts by weight of the food composition of the present disclosure.

Specifically, the food composition may be an emulsion formulation further containing an oil, a surfactant and a polyethylene glycol.

In the emulsion formulation, a mixing weight ratio of the oil, the surfactant and the polyethylene glycol may be 0.3-30:1:2-2.5, more specifically 10-20:1:2-2.5. The composition of the emulsion formulation may be determined by a pseudo-ternary phase diagram constructed according to a common method. Specifically, the pseudo-ternary phase diagram may be constructed by, after completely mixing an oil (polyethoxylated castor oil (Kolliphor® EL)) and a surfactant (e.g., a mixture of Tween 80 and a polyethylene glycol) at different mixing weight ratios within a specific range, plotting dots corresponding to an emulsion-forming region while adding water to the mixture of the oil and the surfactant. By determining an emulsion region from the constructed pseudo-ternary phase diagram and selecting a specific composition included in the region, the composition of an emulsion formulation in which the active ingredient (the indirubin derivative, or a mixture of the indirubin derivative and the *Euodia sutchuenensis* Dode extract or one or more selected from a group consisting of methyl vanillate, hesperidin and quercitrin) is dissolved can be determined.

Specifically, when the composition is an emulsion formulation, the active ingredient (the indirubin derivative, or a mixture of the indirubin derivative and the *Euodia sutchuenensis* Dode extract or one or more selected from a group consisting of methyl vanillate, hesperidin and quercitrin) may be contained in an amount of 1-20 wt % based on the total weight of the composition.

The surfactant is a Tween-based non-ionic surfactant and serves as a solubilizer. It is used as an emulsifier or a wetting agent in oral or parenteral pharmaceutical formulations and is also used in cosmetics or foods as an additive. In addition, it is used as a substance for inhibiting p-glycoprotein in order to increase the bioavailability of drugs. The Tween-based surfactant includes one or more selected from a group consisting of polyoxyethylene sorbitan monolaurate (Tween 20), polyoxyethylene sorbitan monopalmitate (Tween 40), polyoxyethylene sorbitan monostearate (Tween 60) and polyoxyethylene sorbitan oleate (Tween 80), although not being limited thereto. The Tween-based surfactant is a stable substance which is approved by the US Food and Drug Administration for use in intravenous injection to human.

The polyethylene glycol is an amphiphilic polymer having both hydrophilicity and hydrophobicity. A polyethylene glycol with a small molecular weight is a liquid, but it becomes a solid as the molecular weight is increased. The polyethylene glycol may be one selected from a group consisting of PEG 150, 300, 400, 1000, 6000, 8000, 10000, 20000, 30000 and 40000. PEG 300 means a polyethylene glycol with a molecular weight of 300. A polyethylene glycol with a molecular weight exceeding 10,000 is also referred to as a polyethylene oxide (PEO). Among them, PEG 400 is in liquid state and is used frequently for solubilization of various poorly soluble drugs. In particular, it is a stable substance the oral and parenteral (intravenous injection, subcutaneous injection, intramuscular injection, etc.) use of which to human is approved by the US Food and Drug Administration (FDA).

In an exemplary embodiment of the present disclosure, the surfactant is polyoxyethylene sorbitan oleate (Tween 80) and the polyethylene glycol is PEG 400, which is amphiphilic, water-dispersible and non-ionic. Therefore, an emulsion formulation optimized for the poorly soluble active ingredient (the active ingredient including an indirubin derivative, an *Euodia sutchuenensis* Dode extract and one or more selected from a group consisting of methyl vanillate, hesperidin and quercitrin) may be provided.

The oil may be one or more selected from a group consisting of polyethoxylated castor oil (Kolliphor® EL), sunflower oil and olive oil.

The composition may further contain a cyclodextrin for better solubilization. The cyclodextrin may be contained in an amount of 100-1000 parts by weight based on 100 parts by weight of the active ingredient present in the composition.

It was confirmed that the emulsion formulation is a stable formulation which does not show change in Wnt activity and solubility in distilled water at 4-25° C. for 3 months, capable of maintaining the activity of the active ingredient for a long period of time and effectively improving absorption into the body.

In addition, the present disclosure provides a method for preparing an emulsion food composition for preventing or alleviating wound, which includes:

1) a step of preparing a first solution by mixing an oil, a surfactant and a polyethylene glycol;
2) a step of preparing a second solution containing one or more indirubin derivative selected from Chemical Formulas 1-4 as an active ingredient; and
3) a step of preparing an emulsion composition by mixing the first solution with the second solution.

The second solution may further contain an *Euodia sutchuenensis* Dode extract and one or more selected from a group consisting of methyl vanillate, hesperidin and quercitrin.

The second solution may further contain a cyclodextrin for better solubilization.

The polyethylene glycol is an amphiphilic polymer having both hydrophilicity and hydrophobicity. A polyethylene glycol with a small molecular weight is a liquid, but it becomes a solid as the molecular weight is increased. The polyethylene glycol may be one selected from a group consisting of PEG 150, 300, 400, 1000, 6000, 8000, 10000, 20000, 30000 and 40000. PEG 300 means a polyethylene glycol with a molecular weight of 300. A polyethylene glycol with a molecular weight exceeding 10,000 is also referred to as a polyethylene oxide (PEO). Among them, PEG 400 is in liquid state and is used frequently for solubilization of various poorly soluble drugs. In particular, it is a stable substance the oral and parenteral (intravenous injection, subcutaneous injection, intramuscular injection, etc.) use of which to human is approved by the US Food and Drug Administration (FDA).

The surfactant is a Tween-based non-ionic surfactant and serves as a solubilizer. It is used as an emulsifier or a wetting agent in oral or parenteral pharmaceutical formulations and is also used in cosmetics or foods as an additive. In addition, it is used as a substance for inhibiting p-glycoprotein in order to increase the bioavailability of drugs. The Tween-based surfactant includes one or more selected from a group consisting of polyoxyethylene sorbitan monolaurate (Tween 20), polyoxyethylene sorbitan monopalmitate (Tween 40), polyoxyethylene sorbitan monostearate (Tween 60) and polyoxyethylene sorbitan oleate (Tween 80), although not being limited thereto. The Tween-based surfactant is a stable substance which is approved by the US Food and Drug Administration for use in intravenous injection to human.

A mixing weight ratio of the oil, the surfactant and the polyethylene glycol may be 0.3-30:1:2-2.5, more specifically 10-20:1:2-2.5. Specifically, when the composition is an emulsion formulation, the active ingredient (the indirubin derivative, or a mixture of the indirubin derivative and the *Euodia sutchuenensis* Dode extract or one or more selected from a group consisting of methyl vanillate, hesperidin and quercitrin) may be contained in an amount of 1-20 wt % based on the total weight of the composition.

When the emulsion composition of the present disclosure was observed with a microscope after adding water, the emulsion of the present disclosure was completely dissolved and an emulsion formulation (F8) in solution state was formed. As a result of observing the stability of the emulsion of the present disclosure, it was confirmed that nanosized spherical droplets with an average diameter of 20-1500 nm, specifically 30-50 nm, were formed and they showed a narrow size distribution.

In addition, it was confirmed that the emulsion of the present disclosure maintains stability for a long period of time, without change in the solubility or activity of the active ingredient at room temperature for 3 months. In addition, the emulsion formulation of the present disclosure can provide effectively improved absorption when administered orally or applied topically.

As can be confirmed from the examples described below, since the one or more indirubin derivative selected from Chemical Formulas 1-4 exhibits remarkably superior effect of regenerating skin and promoting collagen synthesis, it can be used as an active ingredient of medications, cosmetics, health foods, etc. for enhancing skin regeneration and skin elasticity.

In another aspect, the present disclosure relates to a composition for enhancing skin regeneration and skin elasticity, which contains one or more indirubin derivative selected from Chemical Formulas 1-4 as an active ingredient.

[Chemical Formula 1]

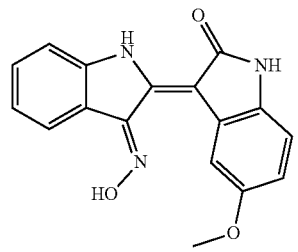

[Chemical Formula 2]

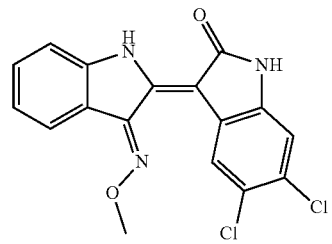

[Chemical Formula 3]

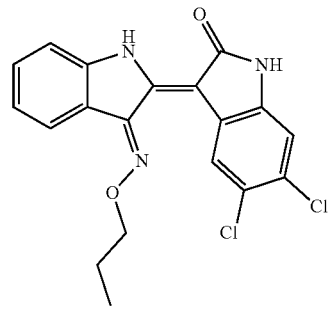

[Chemical Formula 4]

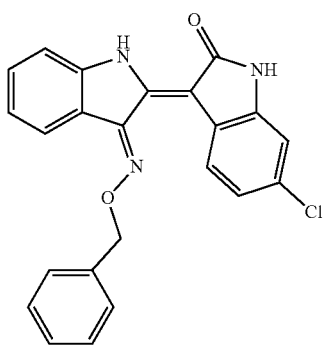

The indirubin derivative of the present disclosure is a substance which exhibits little cytotoxicity even when treated to cells for a long period of time. Because it exhibits excellent effect in regenerating cells, healing wound and producing collagen not only in normal state but also in diabetic state, it can be widely used for medications, foods, cosmetics, etc. having the function of regenerating skin and enhancing skin elasticity.

In the present disclosure, 'skin regeneration' refers to alleviation, removal, mitigation or improvement of skin damage, and 'enhancement of skin elasticity' refers to maintenance and strengthening of the function related with skin elasticity. Skin elasticity is affected mainly by the protein collagen in the dermal layer of the skin. The biosynthesis of collagen is affected by the internal and external factors of the skin. Specifically, collagen biosynthesis is decreased as the cellular activity of skin cells is decreased due to natural aging. Also, reactive oxygen species produced due to external factors such as excessive exposure to UV, skin damage, stress, etc. may inhibit enzymatic activity by reacting with the thiol (—SH) group of the protein or increase the expression of collagen-degrading enzymes, thereby increasing skin wrinkles and decreasing skin elasticity. This leads to skin aging.

There are various indirubin derivatives such as 5-methoxylindirubin-3'-oxime, 5-methoxylindirubin-3'-methoxime, indirubin-3'-oxime, 6-bromoindirubin-3'-oxime, 5,6-dichloroindirubin, 5,6-dichloroindirubin-3'-oxime, 5,6-dichloroindirubin-3'-methoxime, 5,6-dichloroindirubin-3'-propyloxime, 6-chloro-5-nitroindirubin, 6-chloro-5-nitroindirubin-3'-oxime, 6-chloroindirubin-3'-methoxime, 5-chloroindirubin-3'-methoxime, 5-bromoindirubin-3'-oxime, 5-bromoindirubin-3'-methoxime, 5-bromoindirubin-3'-ethyloxime, 5,6-dichloroindirubin-3'-oximepropyloxime, 6-chloroindirubin-3'-benzyloxime, etc. Among them, one or more indirubin derivative selected from Chemical Formulas 1-4 was confirmed to have the most superior effect of treating and healing wound.

When one or more indirubin derivative selected from Chemical Formulas 1-4 was applied to the wound of mouse, it was confirmed that the acute wound of mouse was re-epithelialized comparably to or faster than the positive control group EGF and various collagen activities are increased. It was confirmed that the composition according to the present disclosure has an effect of maximizing cell motility and improving collagen production and accumulation in keratinocytes and fibroblasts, which play an important role in wound healing. Accordingly, the composition according to the present disclosure can be used as an active ingredient of medications, cosmetics, health foods, etc. for enhancing skin regeneration and skin elasticity.

It was confirmed that, when the one or more indirubin derivative selected from Chemical Formulas 1-4 are applied to the wound of a diabetic animal model, the wound was re-epithelialized quickly, collagen activity was enhanced and the cell motility of keratinocytes and fibroblasts was maximized. The effect of enhancing skin regeneration and skin elasticity in diabetic state was remarkably superior as compared to the existing Wnt signaling pathway activator, VPA.

The indirubin derivative used in the present disclosure may be provided not only in free form but also as a pharmaceutically acceptable salt, pharmaceutically acceptable solvate, pharmaceutically acceptable polymorph or pharmaceutically acceptable prodrug thereof. The salt of the indirubin derivative is not specially limited as long as it can be mixed in a pharmaceutical or cosmetic composition. It includes an inorganic salt or an organic salt and can be an acidic salt or an alkaline salt. In particular, a cationic salt may be an alkali metal salt such as a sodium salt, a potassium salt, etc., an alkaline earth metal salt such as a calcium salt, a magnesium salt, a barium salt, etc., a basic amino acid salt such as arginine, lysine, etc., an ammonium salt such as an ammonium salt, a tricyclohexylammonium salt, etc., or an alkanolamine salt such as a monoethanolamine salt, a diethanolamine salt, a triethanolamine salt, a monoisopropanolamine salt, a diisopropanolamine salt, a triisopropanolamine salt, etc. The salt may be specifically an alkali metal salt, more specifically a tetrasodium salt.

In the composition, the indirubin derivative may be contained in an amount of 0.001-80 wt % based on the total weight of the composition. If the content is less than 0.01 wt %, a sufficient effect of preventing or healing wound may not be achieved. And, if it exceeds 80 wt %, skin irritation may be induced.

The composition of the present disclosure may be a mixture further containing an *Euodia sutchuenensis* Dode extract and may be a mixture further containing one or more low-molecular-weight compound selected from a group consisting of methyl vanillate, hesperidin and quercitrin.

A mixture of the *Euodia sutchuenensis* Dode extract and the indirubin derivative at a specific ratio exhibits an excellent effect for wound healing. Specifically, it was confirmed through in-vitro experiments that when treated with the indirubin derivative and the extract together, wound closure rate (%) is improved and wound healing effect is improved beyond a simple synergistic effect (2 fold) as compared to when treated with the one or more indirubin derivative selected from Chemical Formulas 1-4 alone.

In particular, about 1.5-2.0 fold better result was achieved when threated with the mixture as compared to when threated with the *Euodia sutchuenensis* Dode extract alone or when threated with the indirubin derivative alone.

In addition, it was also confirmed through animal experiments that a mixture with the indirubin derivative has a remarkable effect as compared to the *Euodia sutchuenensis* Dode extract or the indirubin derivative alone.

The extract may be prepared from the stem, leaf, fruit, a pulverization product thereof or a mixture thereof of *Euodia sutchuenensis* Dode, as a raw material. The raw material may be extracted using a solvent selected from a group consisting of water, a $C_1$-$C_4$ anhydrous or water-containing lower alcohol, a mixture solvent of the lower alcohol and water, acetone, ethyl acetate, butyl acetate, chloroform and 1,3-butylene glycol as an extraction solvent.

When the composition further contains an *Euodia sutchuenensis* Dode extract, a mixing weight ratio of the one or more indirubin derivative selected from Chemical Formulas 1-4 and the extract is not particularly limited. Specifically, 5-15 parts by weight of the indirubin derivative may be mixed based on 10 parts by weight of the extract based on dry weight. Outside this range, the increase in wound healing effect may be insignificant.

The composition of the present disclosure may be a mixture further containing one or more selected from a group consisting of methyl vanillate, hesperidin and quercitrin. A mixture of the methyl vanillate, hesperidin and quercitrin and the indirubin derivative at a specific ratio exhibits an excellent effect for enhancement of skin regeneration and skin elasticity. Specifically, it was confirmed through in-vitro experiments that when treated with the indirubin derivative together with one or more selected from a group consisting of methyl vanillate, hesperidin and quercitrin, wound closure rate (%) is improved, wound healing effect is improved beyond a simple synergistic effect (1.4-2.3 fold) and wound heals 6 hours faster as compared to when treated with the one or more indirubin derivative selected from Chemical Formulas 1-4 alone. In other words, it was confirmed through experiments that it is the most preferred use the indirubin derivative together with the one or more selected from a group consisting of methyl vanillate, hesperidin and quercitrin.

As demonstrated in the test examples described below, a mixture of the one or more low-molecular-weight compound selected from a group consisting of methyl vanillate, hesperidin and quercitrin and the one or more indirubin derivative selected from Chemical Formulas 1-4 recovered cell motility within 18 hours. In particular, a mixture of methyl vanillate and the indirubin derivative (A3051) showed 5 times better effect as compared to a non-treated control group.

The one or more low-molecular-weight compound selected from a group consisting of methyl vanillate, hesperidin and quercitrin is an ingredient included in an *Euodia sutchuenensis* Dode extract, a *Hovenia dulcis* extract, a tangerine extract, a *Polygonum aviculare* extract, a smartweed extract and a *Houttuynia cordata* extract. The extract is not specially limited as long as it is one extracted from the stem, leaf, fruit, a pulverization product thereof or a mixture thereof of one or more selected from *Euodia sutchuenensis* Dode, *Hovenia dulcis*, tangerine, *Polygonum aviculare*, smartweed and *Houttuynia cordata* as a raw material. Specifically, the raw material may be extracted using a solvent selected from a group consisting of water, a $C_1$-$C_4$ anhydrous or water-containing lower alcohol, a mixture solvent of the lower alcohol and water, acetone, ethyl acetate, butyl acetate, chloroform and 1,3-butylene glycol as an extraction solvent.

The methyl vanillate may exist mainly in the *Hovenia dulcis* extract, the hesperidin may exist mainly in the *Euodia sutchuenensis* Dode extract and the tangerine extract, and the quercitrin may exist mainly in the smartweed extract, the *Polygonum aviculare* extract and the *Houttuynia cordata* extract.

When the composition further contains one or more low-molecular-weight compound selected from a group consisting of methyl vanillate, hesperidin and quercitrin, a mixing weight ratio of the one or more indirubin derivative selected from Chemical Formulas 1-4 and the one or more low-molecular-weight compound selected from a group consisting of methyl vanillate, hesperidin and quercitrin is not particularly limited. Specifically, 1-20 mol of the indirubin derivative may be mixed based on 1 mol of the low-molecular-weight compound. Outside this range, the increase in wound healing effect may be insignificant.

The concentration of the *Euodia sutchuenensis* Dode extract or the low-molecular-weight compound in the composition is not particularly limited as long as it is one general in the art. The *Euodia sutchuenensis* Dode extract or the low-molecular-weight compound may be contained in an amount of 0.001-5 wt % based on dry weight or 0.001-50 wt % based on wet weight, based on the total weight of the composition. If the content is less than 0.001 wt %, a sufficient wound healing effect may not be achieved. And, if it exceeds 5 wt % (dry weight) or 50 wt % (wet weight), skin irritation may be induced.

The cosmetic composition according to the present disclosure may further contain an additive capable of enhancing cosmetic effect by alleviating wound, although not being specially limited thereto.

The cosmetic composition containing the indirubin derivative as an active ingredient according to the present disclosure may be prepared into a toilet water, an essence, a lotion, a cream, a pack, a gel, a powder, a foundation or a cleanser formulation. For example, it may be prepared into a toilet water, a nourishing lotion, a nourishing essence, a massage cream, a cosmetic bath additive, a body lotion, a body milk lotion, a bath oil, a baby oil, a baby powder, a shower gel, a shower cream, a sunscreen lotion, a sunscreen cream, a suntan cream, a skin lotion, a skin cream, an anti-UV cosmetic, a cleansing milk, a cosmetic hair remover, a facial/body lotion, a facial/body cream, a skin-whitening cream, a hand cream, a hair lotion, a cosmetic cream, jasmine oil, a bath soap, a liquid soap, a beauty soap, a shampoo, a hand cleaner, a medicated soap not for medical use, a cream soap, a facial wash, a body cleanser, a scalp cleanser, a hair rinse, a toilet soap, a tooth-whitening gel, a toothpaste, etc. For this, the cosmetic composition of the present disclosure may further contain a solvent commonly used for preparation of a cosmetic composition or a suitable carrier, excipient or diluent.

The solvent that may be further added in the cosmetic composition of the present disclosure is not specially limited. For example, water, saline, DMSO or a combination thereof may be used. The carrier, excipient or diluent may include purified water, an oil, a wax, a fatty acid, a fatty acid alcohol, a fatty acid ester, a surfactant, a humectant, a thickener, an antioxidant, a viscosity stabilizer, a chelating agent, a buffer, a lower alcohol, etc., although not being limited thereto. In addition, a skin-whitening agent, a moisturizer, a vitamin, anti-UV agent, a perfume, a dye, an antibiotic, an antibacterial agent or an antifungal agent may be included, if necessary.

The oil may be hydrogenated vegetable oil, castor oil, cottonseed oil, olive oil, palm kernel oil, jojoba oil or avocado oil, and the wax may be beeswax, spermaceti, carnauba, candelilla wax, montan wax, ceresin, liquid paraffin or lanolin.

The fatty acid may be stearic acid, linoleic acid, linolenic acid or oleic acid, the fatty acid alcohol may be cetyl alcohol, octyldodecanol, oleyl alcohol, panthenol, lanolin alcohol, stearyl alcohol or hexadecanol, and the fatty acid ester may be isopropyl myristate, isopropyl palmitate or butyl stearate. And, the surfactant may be a cationic surfactant, an anionic surfactant or a non-ionic surfactant known in the art. Specifically, a surfactant derived from a natural substance may be used.

In addition, various humectants, thickeners, antioxidants, etc. widely known in the cosmetic industry may also be used with amounts known in the art.

The composition of the present disclosure may be applied or sprayed directly onto the skin.

The present disclosure also relates to a food composition for enhancing skin regeneration or skin elasticity, which contains one or more indirubin derivative selected from Chemical Formulas 1-4 as an active ingredient. The food composition may be prepared from the composition containing the indirubin derivative into a capsule, a tablet, a powder, a granule, a liquid, a pill, a flake, a paste, a syrup, a gel, a jelly or a bar. Also, it may be prepared into regular food by adding to a beverage, a tea, a spice, gum, confectionery, etc. Although it provides specific health benefits when consumed as a food, it has no side effect when a drug is taken for a long period of time.

The food composition is very useful since it can be taken routinely. In the food composition, the addition amount of the indirubin derivative will vary depending on the type of the food composition within a range not negatively affecting the taste of the food. In general, the content of the indirubin derivative in the food composition is 0.001-50 wt %, specifically 0.1-20 wt %. For a functional health food in the form of a capsule, a tablet, a powder, a granule, a liquid, a pill, a flake, a paste, a syrup, a gel, a jelly or a bar, the addition amount is generally 0.1-100 wt %, specifically 0.5-80 wt %.

The food composition may further contain, in addition to the indirubin derivative as an active ingredient, ingredients commonly added when preparing food. Examples include a protein, a carbohydrate, a fat, a nutrient, a seasoning agent and a flavoring agent. Examples of the carbohydrate include a monosaccharide, e.g., glucose, fructose, etc., a disaccharide, e.g., maltose, sucrose, an oligosaccharide, etc., a polysaccharide, e.g., dextrin, cyclodextrin, etc. and a sugar alcohol such as xylitol, sorbitol, erythritol, etc.

The flavoring agent may be a natural flavoring agent (thaumatin or stevia extract (e.g., rebaudioside A, glycyrrhizin, etc.)) or a synthetic flavoring agent (saccharin, aspartame, etc.). For example, when the functional health food of the present disclosure is prepared into a drink or a beverage, it may further contain, in addition to the composition of the present disclosure, citric acid, fructose syrup, sucrose, glucose, acetic acid, malic acid, fruit juice, plant extract, etc.

Specifically, the composition for enhancing skin regeneration or skin elasticity of the present disclosure may be an emulsion formulation further containing an oil, a surfactant and a polyethylene glycol.

In the emulsion formulation, a mixing weight ratio of the oil, the surfactant and the polyethylene glycol may be 0.3-30:1:2-2.5, more specifically 10-20:1:2-2.5. The composition of the emulsion formulation may be determined by a pseudo-ternary phase diagram constructed according to a common method. Specifically, the pseudo-ternary phase diagram may be constructed by, after completely mixing an oil (polyethoxylated castor oil (Kolliphor® EL)) and a surfactant (e.g., a mixture of Tween 80 and a polyethylene glycol) at different mixing weight ratios within a specific range, plotting dots corresponding to an emulsion-forming region while adding water to the mixture of the oil and the surfactant. By determining an emulsion region from the constructed pseudo-ternary phase diagram and selecting a specific composition included in the region, the composition of an emulsion formulation in which the active ingredient (the indirubin derivative, or a mixture of the indirubin derivative and the *Euodia sutchuenensis* Dode extract or one or more selected from a group consisting of methyl vanillate, hesperidin and quercitrin) is dissolved can be determined.

Specifically, when the composition is an emulsion formulation, the active ingredient (the indirubin derivative, or a mixture of the indirubin derivative and the *Euodia sutchuenensis* Dode extract or one or more selected from a group consisting of methyl vanillate, hesperidin and quercitrin) may be contained in an amount of 1-20 wt % based on the total weight of the composition.

The surfactant is a Tween-based non-ionic surfactant and serves as a solubilizer. It is used as an emulsifier or a wetting agent in oral or parenteral pharmaceutical formulations and is also used in cosmetics or foods as an additive. In addition, it is used as a substance for inhibiting p-glycoprotein in order to increase the bioavailability of drugs. The Tween-based surfactant includes one or more selected from a group consisting of polyoxyethylene sorbitan monolaurate (Tween 20), polyoxyethylene sorbitan monopalmitate (Tween 40), polyoxyethylene sorbitan monostearate (Tween 60) and polyoxyethylene sorbitan oleate (Tween 80), although not being limited thereto. The Tween-based surfactant is a stable substance which is approved by the US Food and Drug Administration for use in intravenous injection to human.

The polyethylene glycol is an amphiphilic polymer having both hydrophilicity and hydrophobicity. A polyethylene glycol with a small molecular weight is a liquid, but it becomes a solid as the molecular weight is increased. The polyethylene glycol may be one selected from a group consisting of PEG 150, 300, 400, 1000, 6000, 8000, 10000, 20000, 30000 and 40000. PEG 300 means a polyethylene glycol with a molecular weight of 300. A polyethylene glycol with a molecular weight exceeding 10,000 is also referred to as a polyethylene oxide (PEO). Among them, PEG 400 is in liquid state and is used frequently for solubilization of various poorly soluble drugs. In particular, it is a stable substance the oral and parenteral (intravenous injection, subcutaneous injection, intramuscular injection, etc.) use of which to human is approved by the US Food and Drug Administration (FDA).

In an exemplary embodiment of the present disclosure, the surfactant is polyoxyethylene sorbitan oleate (Tween 80) and the polyethylene glycol is PEG 400, which is amphiphilic, water-dispersible and non-ionic. Therefore, an emulsion formulation optimized for the poorly soluble active ingredient (the active ingredient including an indirubin derivative, an *Euodia sutchuenensis* Dode extract and one or more selected from a group consisting of methyl vanillate, hesperidin and quercitrin) may be provided.

The oil may be one or more selected from a group consisting of polyethoxylated castor oil (Kolliphor® EL), sunflower oil and olive oil.

The composition may further contain a cyclodextrin for better solubilization. The cyclodextrin may be contained in an amount of 100-1000 parts by weight based on 100 parts by weight of the active ingredient present in the composition.

It was confirmed that the emulsion formulation is a stable formulation which does not show change in Wnt activity and solubility in distilled water at 4-25° C. for 3 months, capable of maintaining the activity of the active ingredient for a long period of time and effectively improving absorption into the body.

MODE FOR INVENTION

Hereinafter, the present disclosure will be described in detail through examples, etc. However, the scope and contents of the present disclosure are not reduced or limited by the examples, etc. Also, it is apparent that those of ordinary skill can easily carry out the present disclosure based on the description of the present disclosure including the following examples, even for the matters experimental results of which are not described specifically. It is also apparent that such changes and modifications are included within the scope of the present disclosure.

Example 1. Synthesis of 5-methoxylindirubin-3'-oxime (A3334)

① Synthesis of intermediate 5'-methoxy-[2,3'-biindolinylidene]-2',3-dione

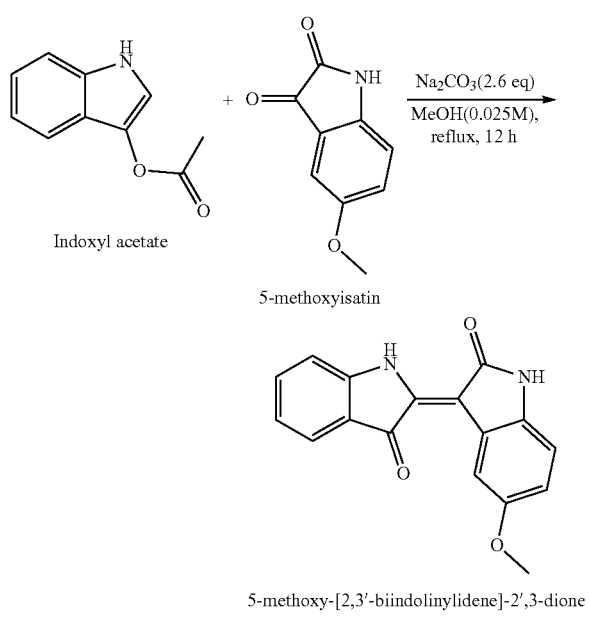 [SMILES: CC(=O)Oc1c[nH]c2ccccc12 ; COc1ccc2c(c1)C(=O)C(=O)N2 ; COc1ccc2c(c1)/C(=C1/Nc3ccccc3C1=O)C(=O)N2]

After dissolving 5-methoxyisatin (1000 mg, 5.65 mmol) in methanol (MeOH; 225 mL) in a 250-mL round-bottom flask and adding indoxyl acetate (989 mg, 5.65 mmol) and sodium carbonate (Na$_2$CO$_3$; 1496 mg, 14.11 mmol), the mixture was stirred at 65° C. for 12 hours. After identifying the completion of reaction by TLC (R$_f$=0.4, ethyl acetate/hexane=1/2 (v/v)), the product was cooled on ice until a crystal lump was formed. The formed crystal was filtered and the solvent was removed. After discarding the filtrate, the product was washed several times with a solvent (ethanol/water=1/1 (v/v)). The product was filtered, dried in a vacuum pump and then used in the next step without further purification.

② Synthesis of A3334

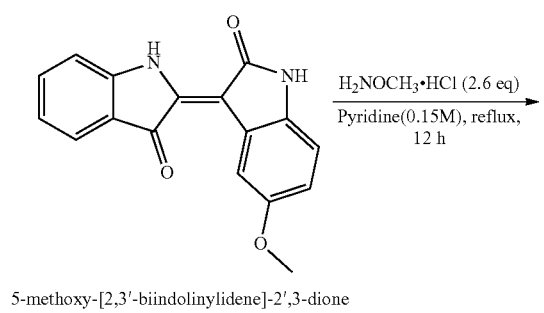

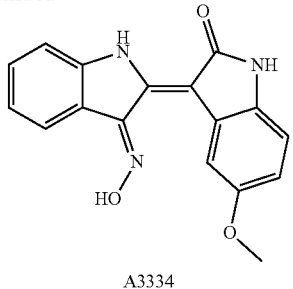

After dissolving 5'-methoxy-[2,3'-biindolinylidene]-2',3-dione (670 mg, 2.29 mmol) in pyridine (27 mL) in a 100-mL round-bottom flask and adding H$_2$NOH·HCl (3186 mg, 45.85 mmol), the mixture was stirred at 120° C. for 12 hours. After identifying the completion of reaction by TLC (R$_f$=0.5, ethyl acetate/hexane=1/1 (v/v)), the temperature of the reaction solution was lowered to room temperature. After completely evaporating the pyridine solvent and dissolving the product in water and ethyl acetate by sonicating for 30 minutes, the solution was extracted twice with ethyl acetate and then washed with a saturated sodium bicarbonate (NaHCO$_3$) solution. After dehydrating the extracted solution with anhydrous magnesium sulfate and evaporating the solvent, the product was recrystallized using methanol and hexane. A3334 (420 mg, yield: 59%) could be obtained as a red solid by drying the product in a vacuum pump. $^1$H NMR (400 MHz, DMSO-d$_6$) δ 13.52 (s, 1H), 11.79 (s, 1H), 10.54 (s, 1H), 8.35 (d, J=1.5 Hz, 1H), 8.26 (d, J=7.6 Hz, 1H), 7.41 (d, J=2.8 Hz, 2H), 7.08-7.00 (m, 1H), 6.82-6.71 (m, 2H), 3.78 (s, 3H).

Example 2. Synthesis of 5,6-dichloroindirubin-3'-methoxime (A3051)

① Synthesis of Intermediate 5',6'-dichloro-[2,3'-biindolinylidene]-2'3-dione

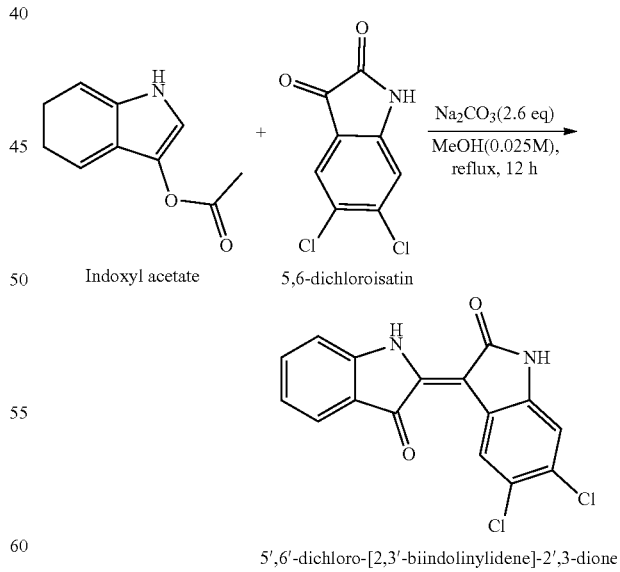

After dissolving 5,6-dichloroisatin (500 mg, 2.32 mmol) in methanol (MeOH; 92.80 mL) in a 250-mL round-bottom flask and adding indoxyl acetate (405.48 mg, 2.315 mmol) and sodium carbonate (Na$_2$CO$_3$; 637.83 mg, 6.02 mmol), the mixture was stirred at 65° C. for 12 hours. After identifying the completion of reaction by TLC ($R_f$=0.4, ethyl acetate/hexane=1/2 (v/v)), the product was cooled on ice until a crystal lump was formed. The formed crystal was filtered and the solvent was removed. After discarding the filtrate, the product was washed several times with a solvent (ethanol/water=1/1 (v/v)). The product was filtered, dried in a vacuum pump and then used in the next step without further purification.

② Synthesis of A3051

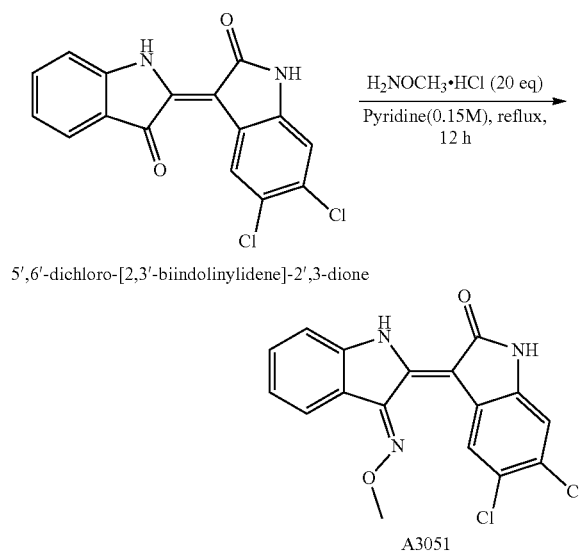

5',6'-dichloro-[2,3'-biindolinylidene]-2',3-dione

A3051

After dissolving 5',6'-dichloro-[2,3'-biindolinylidene]-2'3-dione (600 mg, 1.81 mmol) in pyridine (151 mL) in a 100-mL round-bottom flask and adding $H_2NOCH_3 \cdot HCl$ (3026.4 mg, 36.24 mmol), the mixture was stirred at 120° C. for 12 hours. After identifying the completion of reaction by TLC ($R_f$=0.4, ethyl acetate/hexane=1/1 (v/v)), the temperature of the reaction solution was lowered to room temperature. After completely evaporating the pyridine solvent and dissolving the product in water and ethyl acetate by sonicating for 30 minutes, the solution was extracted twice with ethyl acetate and then washed with a saturated sodium bicarbonate ($NaHCO_3$) solution. After dehydrating the extracted solution with anhydrous magnesium sulfate and evaporating the solvent, the product was recrystallized using methanol and hexane. A3051 (326 mg, yield: 47.94%) could be obtained as a red solid by drying the product in a vacuum pump. $^1$H NMR (400 MHz, DMSO-$d_6$) δ 11.36 (s, 2H), 8.80 (s, 1H), 8.08 (d, 1H, J=7.7 Hz), 7.46-7.41 (m, 2H), 7.07-6.99 (m, 2H), 4.38 (s, 3H).

Examples 3 and 4. Preparation of Indirubin Derivatives of Chemical Formula 3 and Chemical Formula 4

5,6-Dichloroindirubin-3'-oximepropyloxime (A3486) of Chemical Formula 3 and 6-chloroindirubin-3'-benzyloxime (A3538) of Chemical Formula 4 were synthesized in the same manner as the 5,6-dichloroindirubin-3'-methoxime or 5-methoxylindirubin-3'-oxime, and were used in experiments by dissolving in dimethyl sulfoxide (DMSO).

Example 5. Preparation of Methyl Vanillate
Methyl vanillate purchased from Sigma Aldrich was used.
Example 6. Preparation of Hesperidin
Hesperidin purchased from Sigma Aldrich was used.
Example 7. Preparation of Quercitrin
Quercitrin purchased from Sigma Aldrich was used.

Example 8. Preparation of *Euodia sutchuenensis* Dode Extract
An *Euodia sutchuenensis* Dode extract purchased from Korea Plant Extract Bank was used.

Examples 9-11. Preparation of Mixtures
Mixtures were prepared by mixing the methyl vanillate of Example 5, the hesperidin of Example 6, the quercitrin of Example 7 and the indirubin derivative represented by Chemical Formula 2 (A3051) of Example 2 at adequate ratios.

Example 12. Preparation of Mixture of *Euodia sutchuenensis* Dode Extract and Indirubin Derivative (A3334)
A mixture was prepared by mixing the *Euodia sutchuenensis* Dode extract of Example 8 (0.1 μg/mL, 1 μg/mL, 1 mg/mL) with the indirubin derivative represented by Chemical Formula 1 (A3334) of Example 1 (0.1 μM, 1 μM, 0.5 mM). The mixing ration of the *Euodia sutchuenensis* Dode extract and the indirubin derivative is described in the corresponding test example.

Example 13. Preparation of Mixture of *Euodia sutchuenensis* Dode Extract and Indirubin Derivative (A3051)
A mixture was prepared by mixing the *Euodia sutchuenensis* Dode extract of Example 8 (0.1 μg/mL, 1 μg/mL, 1 mg/mL) with the indirubin derivative represented by Chemical Formula 2 (A3051) of Example 2 (0.1 μM, 1 μM, 0.5 mM). The mixing ration of the *Euodia sutchuenensis* Dode extract and the indirubin derivative is described in the corresponding test example.

Example 14. Preparation of Mixture of *Euodia sutchuenensis* Dode Extract and Indirubin Derivative (A3486)
A mixture was prepared by mixing the *Euodia sutchuenensis* Dode extract of Example 8 (0.1 μg/mL, 1 μg/mL, 1 mg/mL) with the indirubin derivative represented by Chemical Formula 3 (A3486) of Example 3 (0.1 μM, 1 μM, 0.5 mM). The mixing ration of the *Euodia sutchuenensis* Dode extract and the indirubin derivative is described in the corresponding test example.

Comparative Example 1. Indirubin-3'-oxime (I3O or IO)

[Chemical Formula 5]

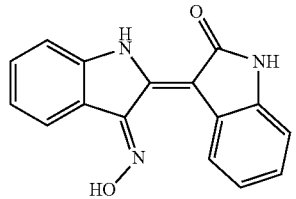

Comparative Example 2. 5,6-Dichloroindirubin (A2941)

[Chemical Formula 6]

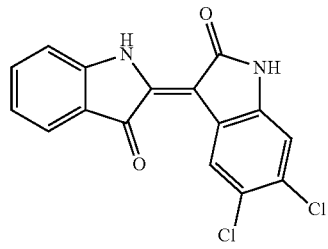

5,6-Dichloroindirubin of Chemical Formula 6, an intermediate of the indirubin derivative of Example 2 (Chemical Formula 2), was prepared in the same manner as in Example 2-①.

Comparative Example 3. 5,6-Dichloroindirubin-3'-oxime (A3050)

[Chemical Formula 7]

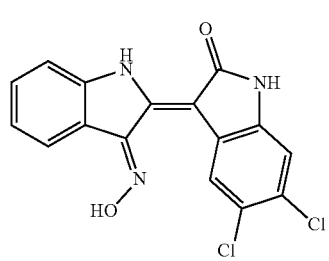

Comparative Example 4. 6-Chloro-5-nitroindirubin (A2735)

[Chemical Formula 8]

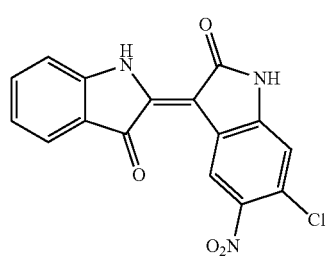

Comparative Example 5. 6-Chloro-5-nitroindirubin-3'-oxime (A2736)

[Chemical Formula 9]

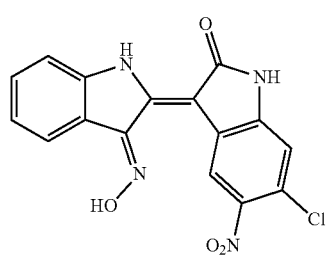

After dissolving 6-chloro-5-nitroindirubin (A2735; 350 mg, 1.02 mmol) in pyridine (7 mL) in a 50-mL round-bottom flask and adding $H_2NOH \cdot HCl$ (711.78 mg, 10.24 mmol), the mixture was refluxed at 120° C. or above for about 12 hours. After identifying the completion of reaction by TLC ($R_f$=0.5, ethyl acetate/hexane=1/1 (v/v)), the temperature of the reaction solution was lowered to room temperature. After completely evaporating the pyridine solvent and dissolving the product in water and ethyl acetate by sonicating for 30 minutes, the solution was extracted twice with ethyl acetate and then washed with a saturated sodium bicarbonate ($NaHCO_3$) solution. After dehydrating the extracted solution with anhydrous magnesium sulfate and evaporating the solvent, the product was recrystallized using methanol and hexane. A2736 (284 mg, yield: 78%) could be obtained as a red solid by drying the product in a vacuum pump. $^1$H NMR (400 MHz, DMSO-$d_6$) δ 13.81 (s, 1H), 11.77 (s, 1H), 11.30 (s, 1H), 9.13 (s, 1H), 8.16 (d, J=8.0 Hz, 1H), 7.42-7.35 (m, 2H), 7.04 (t, J=8.0 Hz, 1H), 6.99 (s, 1H).

Comparative Example 6. 6-Chloroindirubin-3'-methoxime (A2793)

[Chemical Formula 10]

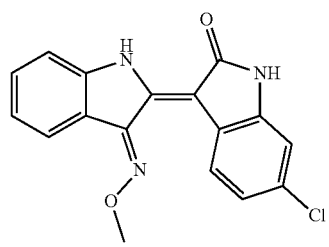

Comparative Example 7. 5-Bromoindirubin-3'-methoxime (A3391)

[Chemical Formula 11]

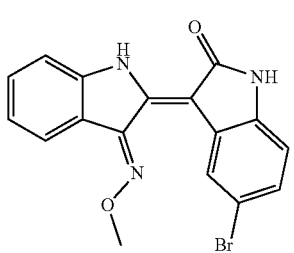

Comparative Example 8. 5-Methoxylindirubin-3'-methoxime (A3441)

[Chemical Formula 12]

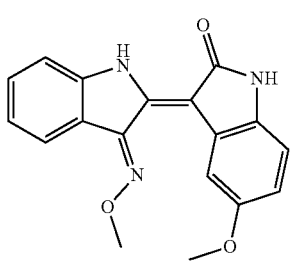

Comparative Example 9. 5-Chloroindirubin-3'-methoxime (A3440)

[Chemical Formula 13]

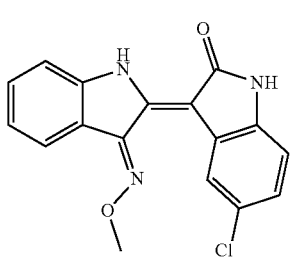

Comparative Example 10. 5-Bromoindirubin-3'-oxime (A3390)

[Chemical Formula 14]

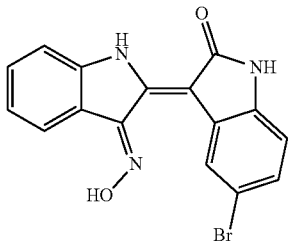

Comparative Example 11. 5-Bromoindirubin-3'-ethyloxime (A3472)

[Chemical Formula 15]

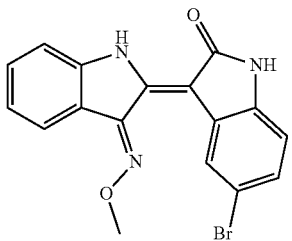

Comparative Example 12. 5-Methylindirubin (A3330)

[Chemical Formula 16]

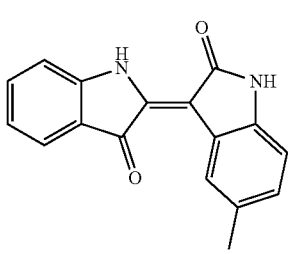

Test Example 1. Investigation of Cell Motility

Cell motility was compared for the indirubin derivatives prepared in Examples 1-4 and the indirubin derivatives prepared in Comparative Examples 1-12.

HaCaT cells, which are human keratinocytes playing an important role in wound healing, were cultured in a 12-well plate for 24 hours using DMEM containing 10% FBS. Then, after replacing the medium with DMEM containing 5% FBS, a scratch was made at the center of the cells using a 1000p (blue) tip. Then, after treating the scratched area with each of the indirubin derivatives of Examples 1-4 and Comparative Examples 1-12 at a concentration of 5 μg/mL or 1 μM, cell motility was observed 24 hours later.

Figure 2:
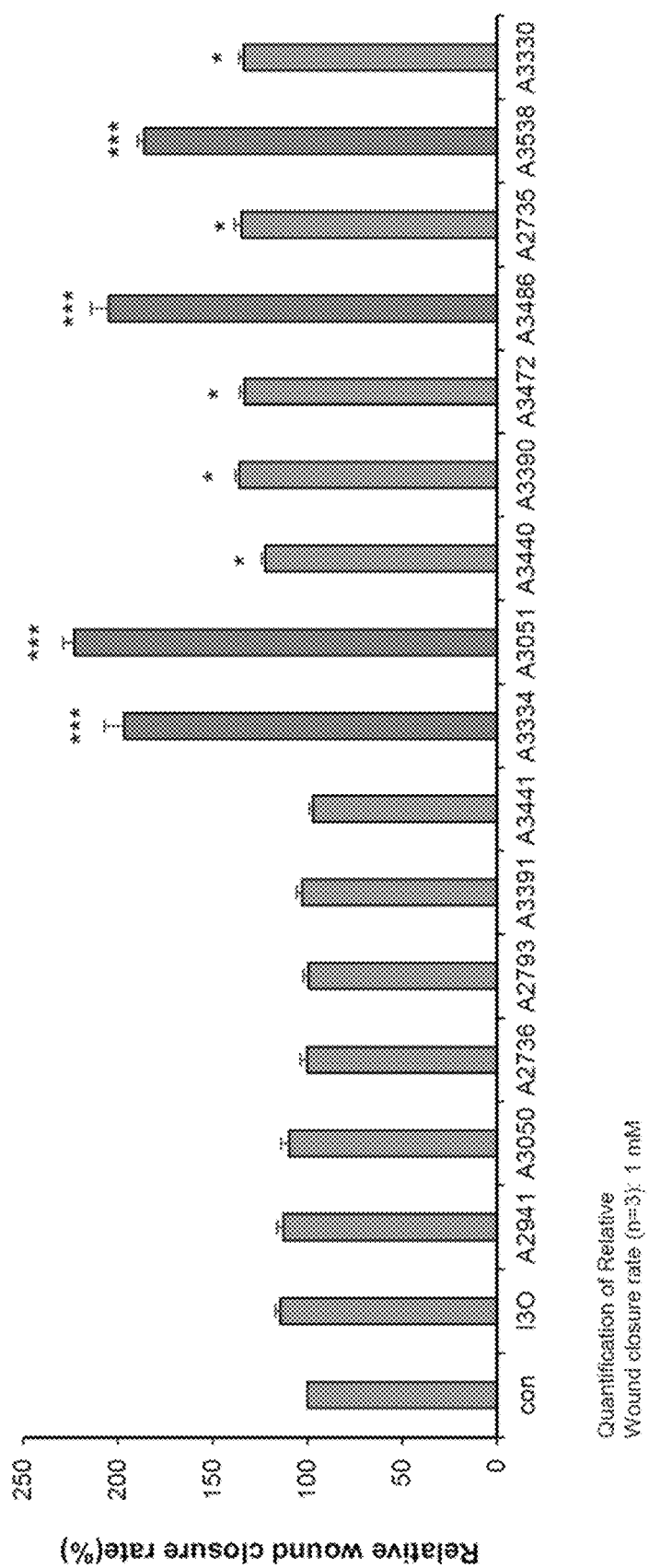
FIG. 2 quantitatively shows the cell motility of keratinocytes depending on treatment with indirubin derivatives prepared in Examples 1-4 and Comparative Examples 1-12.

FIG. 1 shows the cell motility of the keratinocytes depending on treatment with the indirubin derivatives prepared in Examples 1-4 and Comparative Examples 1-12, and FIG. 2 quantitatively shows the cell motility of the keratinocytes depending on treatment with the indirubin derivatives prepared in Examples 1-4 and Comparative Examples 1-12. The control group (con) means keratinocytes not treatment with an indirubin derivative.

In FIG. 2, the wound closure rate (%) is a measure of the cell motility of the keratinocytes, which play an important role in wound healing, when treated with the indirubin derivatives prepared in Examples 1-4 and Comparative Examples 1-12, obtained by quantifying the result of FIG. 1.

As seen from FIG. 1, it was confirmed that there was no difference in cell motility between the indirubin derivatives prepared in Comparative Examples 1-12 and the control group.

In contrast, the cells treated with the indirubin derivatives prepared in Examples 1-4 showed cell motility improved by up to 1.5-2 times as compared to the cells of the control group. In addition, it was confirmed that the treatment with the indirubin derivatives of Examples 1-4, A3334, A3051, A3486 and A3538, improved the cell motility of the keratinocytes, which play an important role in wound healing, by 2 times or more as compared to other similar indirubin derivatives.

That is to say, it was confirmed that the indirubin derivatives of Examples 1-4 exhibits an unexpected effect when compared with the existing indirubin derivatives of very similar structure, which can be seen as a significant increase in effect beyond the expected effect.

Test Example 2. Investigation of Wound Healing- and Collagen Synthesis-Promoting Effect Through Animal Experiments The wound healing-promoting effect of the indirubin derivatives prepared in Examples 1 and 2, the indirubin derivative of Comparative Example 1 (10) and EGF, known as an existing wound healing agent, as a positive control group was investigated through animal experiments.

The hair on the back of 7-week-old C3H mouse that entered the resting period was removed and a 1.5×1.5 cm$^2$ wound was made on the hair-removed region. 20 μL of a vehicle (10% DMSO, 45% ethanol, 18% propylene glycol, 27% water) and the indirubin derivative of Comparative Example 1 (10) were applied to a control group and a comparison group, respectively, once daily for 12 days. For the positive control group, 100 μM EGF was applied once daily for 12 days. For a first test group, 20 μL of the indirubin derivative of Example 2 (A3051) was applied once daily for 12 days. For a second test group, 20 μL of the indirubin derivative of Example 1 (A3334) was applied once daily for 12 days.

The tissue of each experimental mouse was fixed by immersing in 4% paraformaldehyde, embedded in paraffin and then sliced into 4 μm thickness. The sliced tissue was deparaffinized, rehydrated and then stained with Masson's trichrome and Picrosirius red for evaluation of the degree of collagen synthesis. For Masson's trichrome staining, a slide was placed in Weigert's iron hematoxylin solution for 10 minutes and in Biebrich scarlet-acid fuchsin and aniline blue for 5 minutes each. For Picrosirius red staining, a slide was placed in Weigert's solution for 8 minutes and in Picrosirius red for 1 hour.

Figure 3:
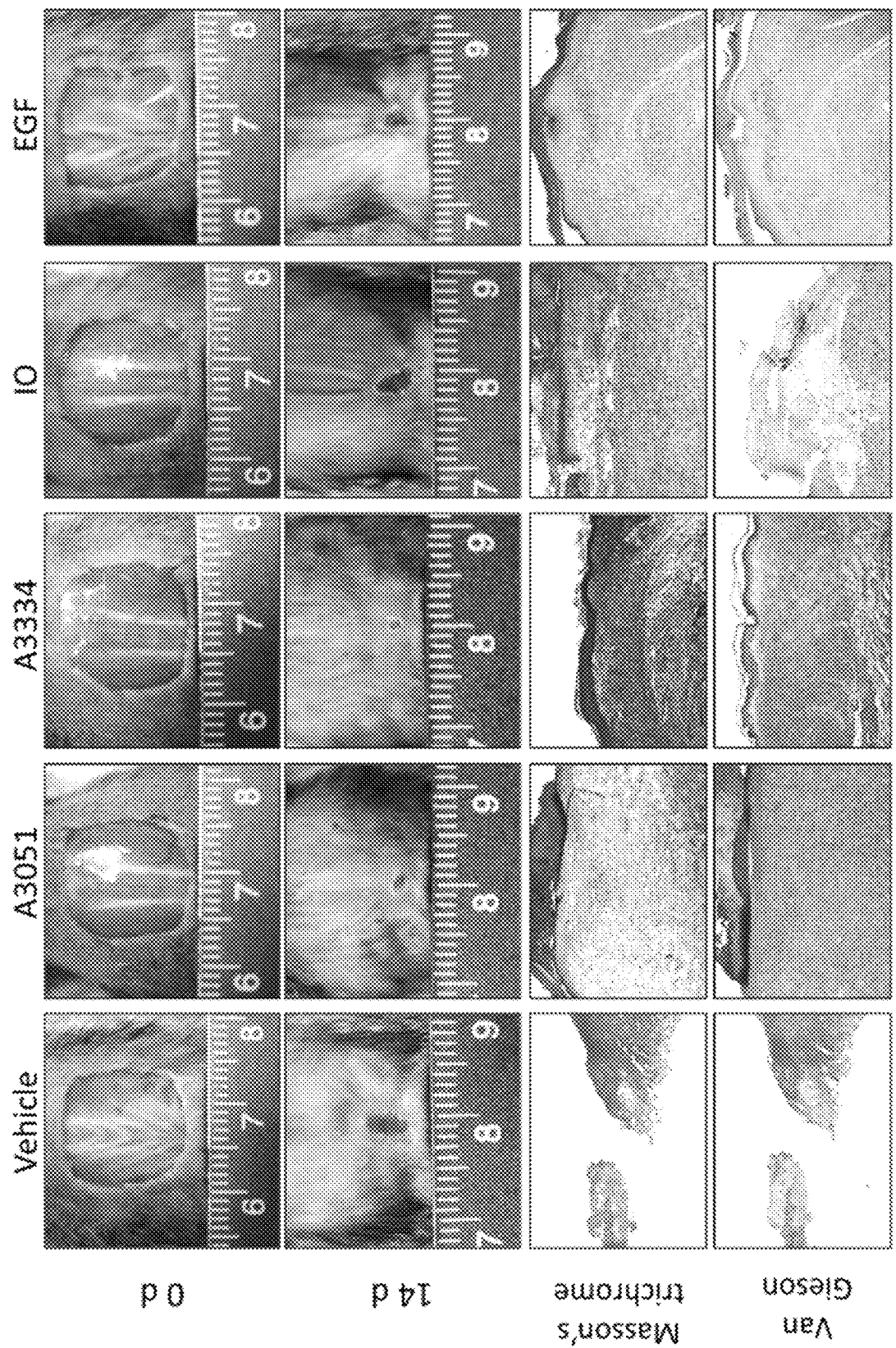
FIG. 3 shows a result of imaging and staining mouse acute wound tissue treated with indirubin derivatives of Example 1 and Example 2 according to the present disclosure, an indirubin derivative of Comparative Example 1 or EGF (positive control group) at different times (days 0 and 14). A result of staining the mouse acute wound tissue treated with the indirubin derivatives of Example 1 and Example 2 according to the present disclosure, the indirubin derivative of Comparative Example 1 or EGF (positive control group) with Masson's trichrome and Picrosirius red is shown at the bottom of FIG. 3 (collagen staining).

FIG. 3 shows a result of imaging and staining the mouse acute wound tissue treated with the indirubin derivatives of Example 1 and Example 2 according to the present disclosure, the indirubin derivative of Comparative Example 1 or EGF (positive control group) at different times (days 0 and 14). A result of staining the mouse acute wound tissue treated with the indirubin derivatives of Example 1 and Example 2 according to the present disclosure, the indirubin derivative of Comparative Example 1 or EGF (positive control group) with Masson's trichrome and Picrosirius red is shown at the bottom of FIG. 3 (collagen staining).

Figure 4:
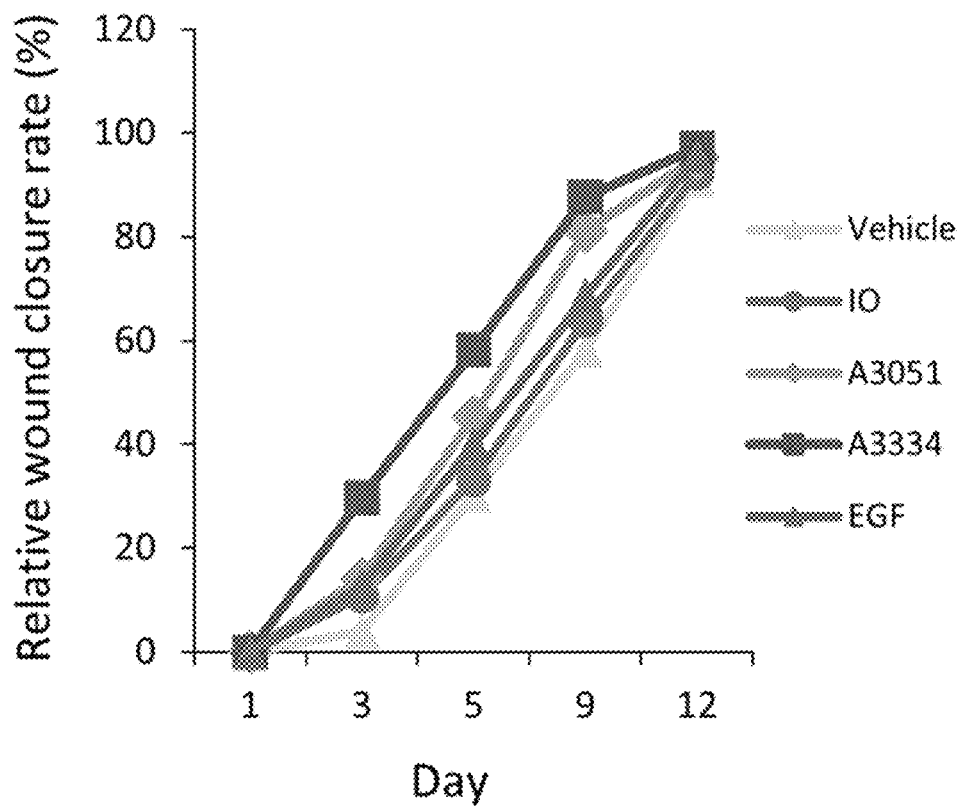
FIG. 4 shows a result of quantifying the degree of re-epithelialization of mouse acute wound tissue treated with indirubin derivatives of Example 1 and Example 2, an indirubin derivative of Comparative Example 1 or EGF (positive control group) at different times (days 1, 3, 5, 9 and 12).

FIG. 4 shows a result of quantifying the degree of re-epithelialization of the mouse acute wound tissue treated with the indirubin derivatives of Example 1 and Example 2, the indirubin derivative of Comparative Example 1 or EGF (positive control group) at different times (days 1, 3, 5, 9 and 12).

Figure 5:
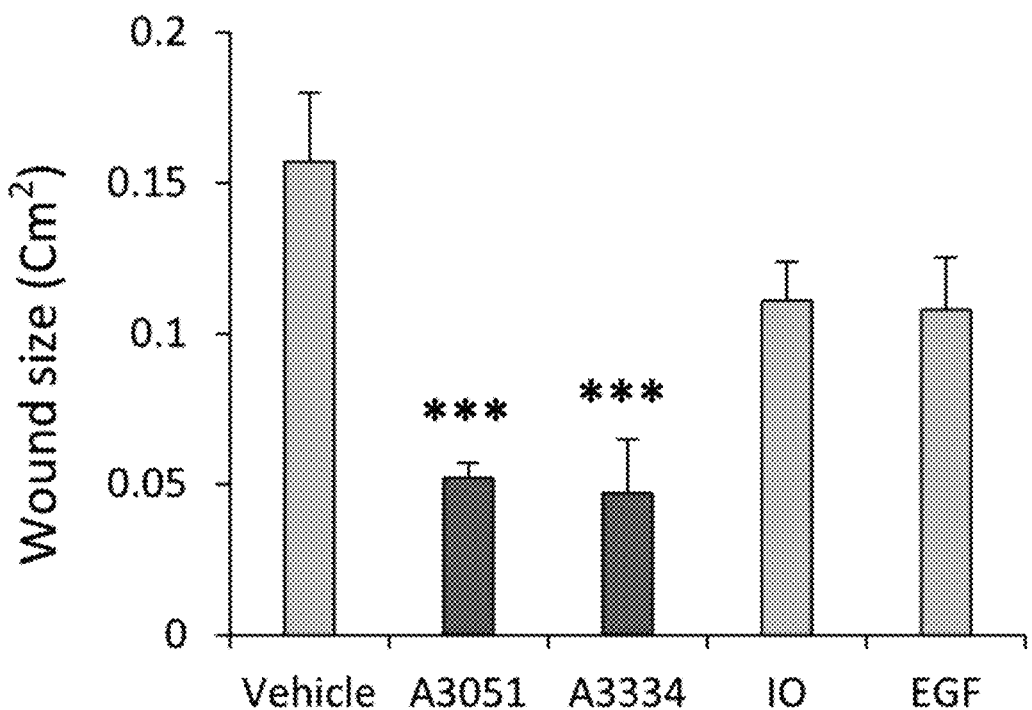
FIG. 5 shows a result of measuring the wound size ($cm^2$) of mouse treated with indirubin derivatives of Example 1 and Example 2, an indirubin derivative of Comparative Example 1 or EGF (positive control group) on day 14.

FIG. 5 shows a result of measuring the wound size (cm$^2$) of the mouse treated with the indirubin derivatives of Example 1 and Example 2, the indirubin derivative of Comparative Example 1 or EGF (positive control group) on day 14.

As shown in FIGS. 3-5, it was confirmed that the acute wound heals quickly in the mouse model when treated with the indirubin derivatives prepared in Examples 1 and 2 as compared to the control group, Comparative Example 1 or the positive control group. That is to say, it was confirmed that when the indirubin derivatives of Examples 1 and 2 were applied to the wound of mouse, the acute wound of the mouse was re-epithelialized comparably to or faster than the positive control group EGF and various wound healing markers of collagen tissue were increased.

In particular, the indirubin derivative of Example 1 (A3334) showed slightly superior wound repair effect as compared to the positive control group EGF and also showed scar-reducing effect of repairing the epidermal layer of skin without remaining scars such as lump, recess, etc.

It was confirmed that the indirubin derivative of Example 2 (A3051) exhibits 2-6 times better wound repair effect during the same period of time as compared to the positive control group EGF, suggesting that it can repair wound faster. In addition, it was confirmed that the epidermal layer is repaired cleanly and uniformly during wound healing without remaining scars such as lump, recess, etc. as compared to when treated with the positive control group EGF, suggesting that it is very effective in reducing scarring as compared to EGF.

In other words, it was confirmed that the indirubin derivatives of Examples 1 and 2 has an unexpectedly remarkably effect of reducing scarring by inducing uniform repair of the epidermal layer of skin, in addition to wound healing effect, unlike the existing wound healing agents or indirubin derivatives.

Also, as shown in FIG. 3, when the mouse acute wound tissue treated with the indirubin derivatives prepared in Example 1 and Example 2, the indirubin derivative prepared in Comparative Example 1 or EGF (positive control group) was stained with Masson's trichrome, Picrosirius red and van Gieson's stain to investigate the type and quantity of collagen, it was confirmed that the treatment with the indirubin derivatives of Examples 1 and 2 not only enables fast wound repair but also remarkably increases the quantity of collagen as compared to the control group, Comparative Example 1 or the positive control group.

When a mouse model treated with epidermal growth factor (EGF) in the same manner as the mouse model of Example 2 was treated with two stains (Masson's trichrome and Picrosirius red), it was confirmed that the use of the indirubin derivatives prepared in Examples 1 and 2 provides superior wound healing effect as compared to direct treatment with the epidermal growth factor (EGF) or the treatment with the indirubin derivative of Comparative Example 1.

Test Example 3. Analysis of Wound Healing Effect of Composition Containing Mixture of Indirubin Derivatives (Chemical Formula 1 or 2) as Active Ingredient For analysis of wound healing effect, cell motility was compared for treatment with the indirubin derivative prepared in Example 2, the methyl vanillate of Example 5, the hesperidin of Example 6, the quercitrin of Example 7 and the mixtures prepared in Examples 9-11.

HaCaT cells, which are human keratinocytes playing an important role in wound healing, were cultured in a 12-well plate for 24 hours using DMEM containing 10% FBS. Then, after replacing the medium with DMEM containing 5% FBS, a scratch was made at the center of the cells using a 1000p (blue) tip. Then, after treating the scratched area with each of the indirubin derivative prepared in Example 2, the methyl vanillate of Example 5, the hesperidin of Example 6, the quercitrin of Example 7 and the mixtures prepared in Examples 9-11 at a concentration of 1 μM or 5 μM, cell motility was observed 18 hours later.

Specifically, the concentration of the indirubin derivative prepared in Example 2, the hesperidin of Example 6 and the quercitrin of Example 7 was 1 μM, the concentration of the methyl vanillate of Example 5 was 5 μM, and the mixtures prepared in Examples 9-11 were prepared by mixing 1 μM indirubin derivative with 5 μM methyl vanillate, 1 μM hesperidin or 1 μM quercitrin.

Figure 6A:
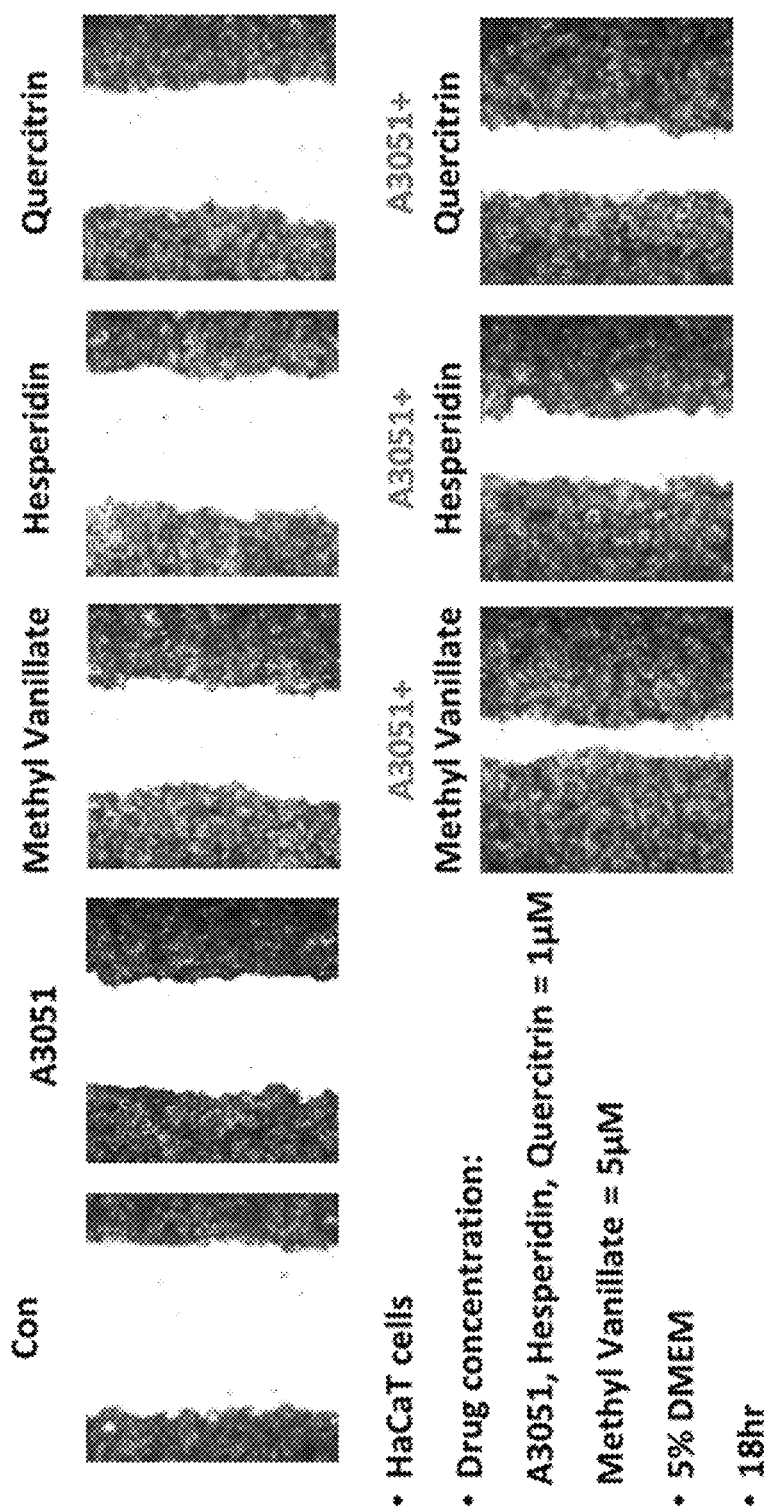
FIG. 6a shows the cell motility of keratinocytes depending on treatment with an indirubin derivative of Example 2, methyl vanillate of Example 5, hesperidin of Example 6, quercitrin of Example 7 or mixtures prepared in Examples 9-11.
Figure 6B:
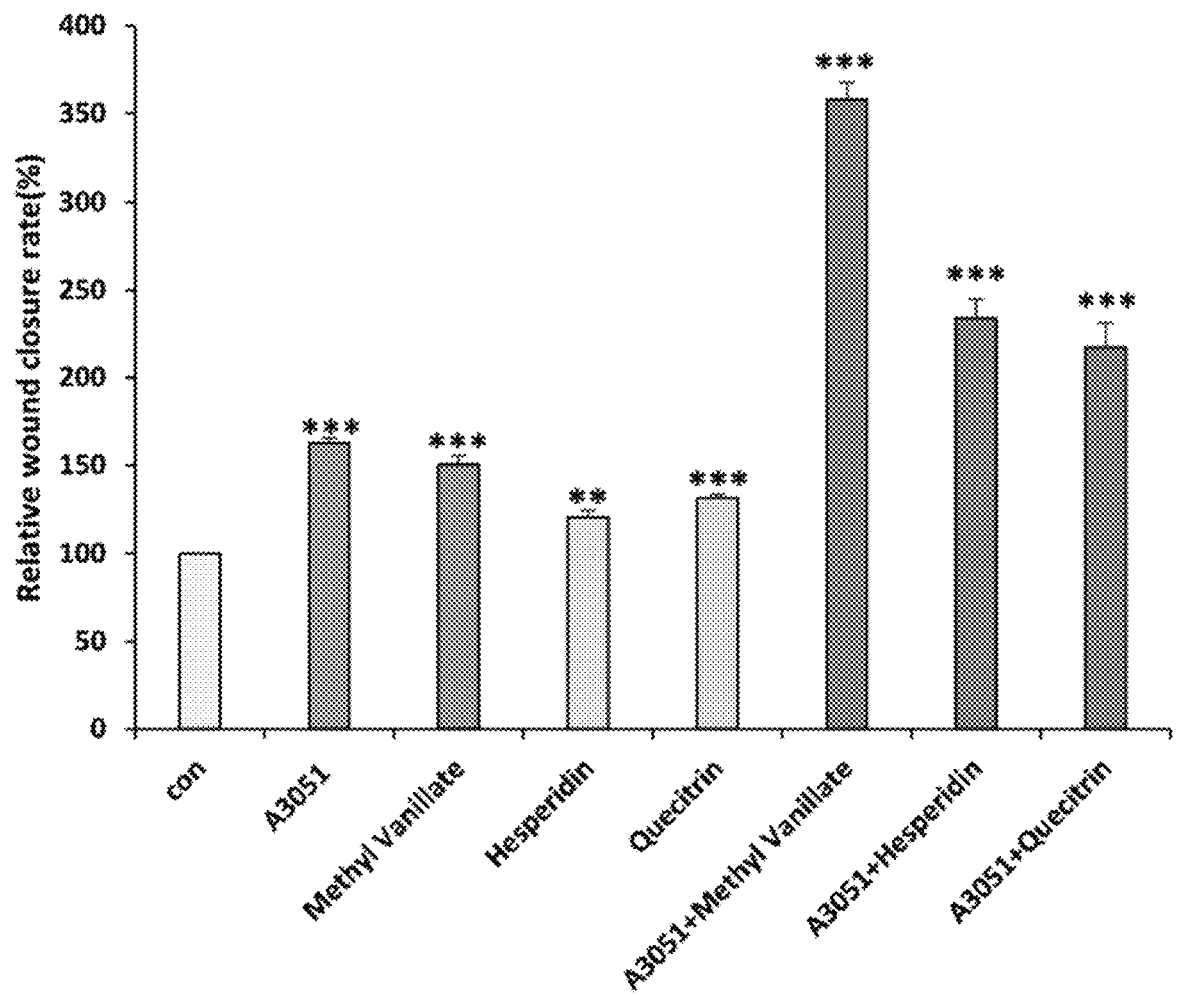
FIG. 6b quantitatively shows the cell motility of keratinocytes depending on treatment with an indirubin derivative of Example 2, methyl vanillate of Example 5, hesperidin of Example 6, quercitrin of Example 7 or mixtures prepared in Examples 9-11.

FIG. 6a shows the cell motility of keratinocytes depending on treatment with the indirubin derivative of Example 2, the methyl vanillate of Example 5, the hesperidin of Example 6, the quercitrin of Example 7 or the mixtures prepared in Examples 9-11. FIG. 6b quantitatively shows the cell motility of keratinocytes depending on treatment with the indirubin derivative of Example 2, the methyl vanillate of Example 5, the hesperidin of Example 6, the quercitrin of Example 7 or the mixtures prepared in Examples 9-11. The control group (control) means non-treated keratinocytes. The wound closure rate (%) is a measure of the cell motility of the keratinocytes, which play an important role in wound healing, when treated with the indirubin derivative prepared in Example 2, the methyl vanillate of Example 5, the hesperidin of Example 6, the quercitrin of Example 7 or the mixtures prepared in Examples 9-11 (FIG. 6).

As shown in FIG. 6, it was confirmed that there was no difference in cell motility between the treatment with the methyl vanillate of Example 5, the hesperidin of Example 6 or the quercitrin of Example 7 alone and the control group.

In contrast, the cells treated with the mixtures prepared in Examples 9-11 showed cell motility improved by up to 2.5-4 times as compared to the cells of the control group.

In this experiment, measurement was made 18 hours, 6 hours earlier than in FIG. 1, after the treatment with each active ingredient. It was confirmed that the treatment with the mixtures prepared in Examples 9-11 improved the cell motility of keratinocytes, which play an important role in wound healing, faster and more (1.4-2.3 times or more) as compared to when the cells were treated with the indirubin derivative of Example 2 (A3051) alone.

That is to say, it was confirmed that an unexpectedly remarkable significant effect (faster and more (2.5-4 times) recovery of cell motility) as compared to treatment with the indirubin derivative of Example 2, the methyl vanillate of Example 5, the hesperidin of Example 6 or the quercitrin of Example 7 alone was shown.

Test Example 4. Investigation of Wound Healing Effect of Mixtures Through Animal Experiments Wound healing-promoting effect was investigated after treating an animal model with the indirubin derivative of Example 2 (0.5 mM), the methyl vanillate of Example 5 (2.5 mM, 5 mM), the mixture prepared in Example 9 (0.5 mM A3051 and 3 or 5 mM methyl vanillate), EGF (positive control group 1) known as an existing wound healing agent or PTD+VPA (a mixture of a cell-penetrating peptide represented by Arg Lys Thr Gly His Gln Ile Cys Lys Phe Arg Lys Cys and valproic acid, positive control group 2).

The hair on the back of 7-week-old C3H mouse that entered the resting period was removed and a 1.5×1.5 cm² wound was made on the hair-removed region. 100 µM EGF or PTD+VPA was applied to a positive control group, once daily for 12 days. For test groups, 20 µL of the indirubin derivative of Example 2 (0.5 mM), the methyl vanillate of Example 5 (2.5 mM, 5 mM) or the mixture prepared in Example 9 was applied once daily for 12 days.

After measuring wound size of the mouse, the wound tissue was fixed by immersing in 4% paraformaldehyde, embedded in paraffin and then sliced into 4 µm thickness. The sliced tissue was deparaffinized, rehydrated and then the degree of re-epithelialization was analyzed.

Figure 7:
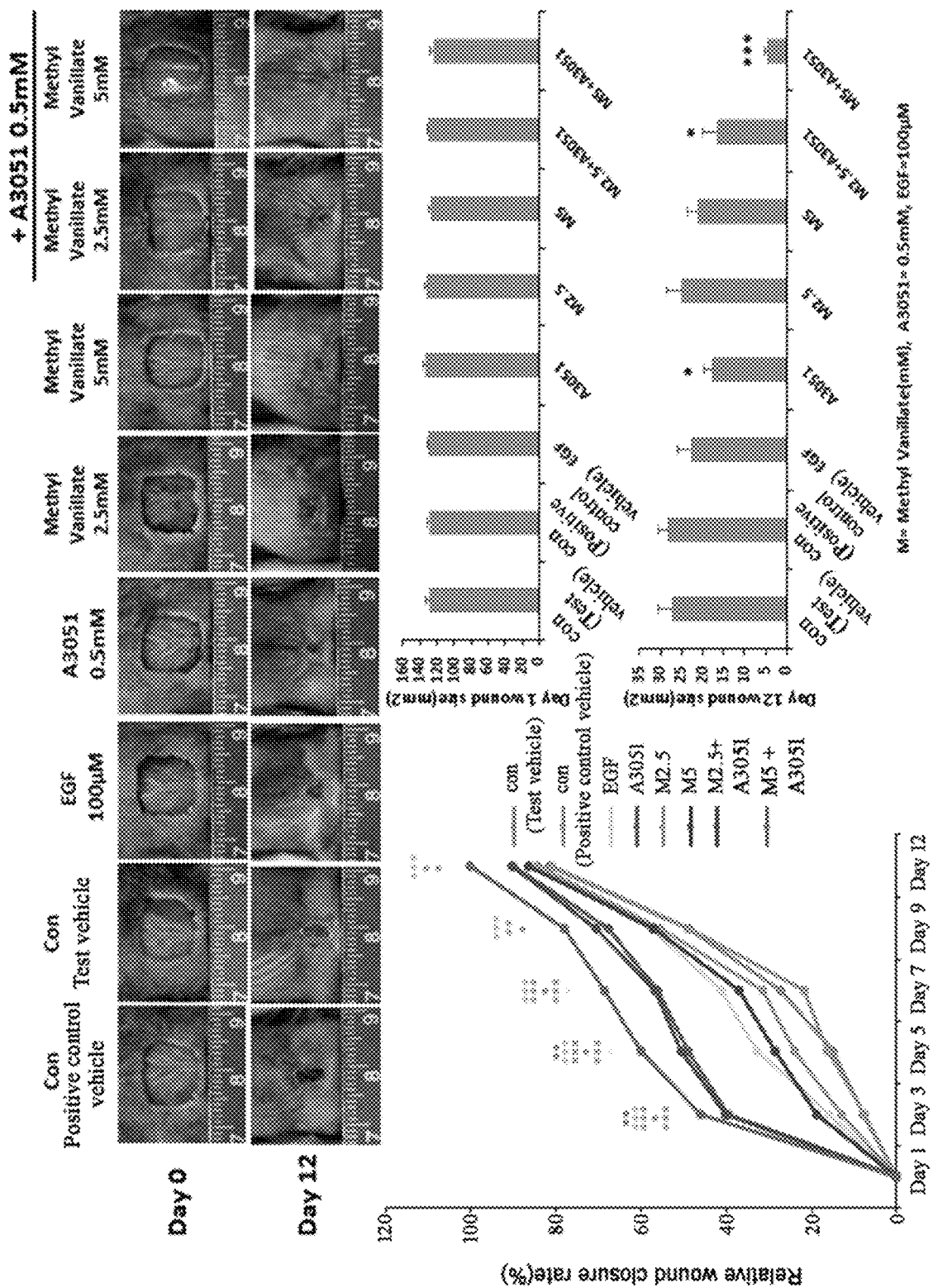
FIG. 7 shows a result of imaging and staining mouse acute wound treated with an indirubin derivative of Example 2 (0.5 mM), methyl vanillate of Example 5 (2.5 mM, 5 mM), a mixture prepared in Example 9 or EGF (positive control group) at different times (days 0 and 12). The graph at the left bottom of FIG. 7 shows a result of quantifying the degree of re-epithelialization of mouse acute wound treated with an indirubin derivative of Example 2 according to the present disclosure (0.5 mM), methyl vanillate of Example 5 (2.5 mM, 5 mM), a mixture prepared in Example 9 or EGF (positive control group) at different times (days 0 and 12). The graph at the right bottom of FIG. 7 shows a result of measuring the wound size ($mm^2$) of mouse treated with an indirubin derivative of Example 2 according to the present disclosure (0.5 mM), methyl vanillate of Example 5 (2.5 mM, 5 mM), a mixture prepared in Example 9 or EGF (positive control group) on days 1 and 12.

FIG. 7 shows a result of imaging and staining the mouse acute wound treated with the indirubin derivative of Example 2 (0.5 mM), the methyl vanillate of Example 5 (2.5 mM, 5 mM), the mixture prepared in Example 9 or EGF (positive control group) at different times (days 0 and 12). The graph at the left bottom of FIG. 7 shows a result of quantifying the degree of re-epithelialization of the mouse acute wound treated with the indirubin derivative of Example 2 according to the present disclosure (0.5 mM), the methyl vanillate of Example 5 (2.5 mM, 5 mM), the mixture prepared in Example 9 or EGF (positive control group) at different times (days 0 and 12). The graph at the right bottom of FIG. 7 shows a result of measuring the wound size (mm²) of the mouse treated with the indirubin derivative of Example 2 according to the present disclosure (0.5 mM), the methyl vanillate of Example 5 (2.5 mM, 5 mM), the mixture prepared in Example 9 or EGF (positive control group) on days 1 and 12. The control group (con) was treated with a solution containing no sample, con (positive control vehicle) was treated with a vehicle consisting of EGF-free distilled water, propylene glycol and ethanol at a volume ratio of 3:2:5, and con (test vehicle) was treated with an emulsion mixture solution of Kollipore®EL:Tween 80:PEG 400 at a mixing weight ratio of 80:6:14.

The composition of Example 2, 5 or 9 was prepared with a concentration suitable for an 'emulsion solution'.

The indirubin derivative of Example 2 (0.5 mM) is marked by A3051 the methyl vanillate of Example 5 (2.5 mM, 5 mM) by M2.5 and M5, and the mixture prepared in Example 9 by M2.5+A3051 or M5+A3051.

As shown in FIG. 7, the acute wound healed quickly when treated with the indirubin derivative of Example 2 (0.5 mM), the methyl vanillate of Example 5 (2.5 mM, 5 mM) or the mixture prepared in Example 9 as compared to the mouse model of the control group or the positive control group. Whereas the wound size was identical on day 1 after the treatment, the mouse to which the M5+A3051 mixture was administered showed significantly faster wound repair, less scarring and faster re-epithelialization on day 12 as compared to the positive control group (EGF).

It was confirmed that, from the mixture of Example 9, the M5+A3051 mixture exhibits 4 times or better wound repair effect as compared to the positive control group (EGF) during the same period of time, suggesting that it repairs wound faster. It was confirmed that the epidermal layer of skin is repaired cleanly and uniformly without remaining cars such as lump, recess, etc. during healing. That is to say, it was confirmed that, although the indirubin derivative of Example 2 also has wound repair effect, the M5+A3051 mixture of Example 9 is very effective for healing wound and reducing scarring.

Test Example 5. Investigation of Wound Healing Effect of Mixture of *Euodia sutchuenensis* Dode Extract and Indirubin Derivative Through Animal Experiments Cell migration was compared after treating cells with the indirubin derivative of Example 1 (0.1 µM, 1 µM), the indirubin derivative of Example 2 (0.1 µM, 1 µM) or the mixtures of Examples 12 and 13 (0.1 µM and 1 µM indirubin derivative mixed with 1 µg/mL *Euodia sutchuenensis* Dode extract, respectively).

A non-treated control group (con), a group treated with the *Euodia sutchuenensis* Dode extract of Example 8 (1 µg/mL) alone (*Euodia sutchuenensis* Dode 1 µg/mL) and a positive control group treated with 100 µM VPA (valproic acid) were prepared.

Experiment was conducted as follows. First, HaCaT cells were cultured in a 12-well plate for 24 hours. The HaCaT cells are human keratinocytes which are known to play an important role in wound healing. DMEM containing 10% FBS was used. After the culturing for 24 hours was completed, the medium was replaced with DMEM containing 5% FBS and a scratch was made at the center of the cells using a 1000p (blue) tip. Then, after treating the scratched area with a sample, cell migration and motility was observed 18 hours later.

As the sample, the indirubin derivative of Example 1 (0.1 µM, 1 µM), the indirubin derivative of Example 2 (0.1 µM, 1 µM) or the mixtures of Examples 12 and 13 (0.1 µM and 1 µM indirubin derivative mixed with 1 µg/mL *Euodia sutchuenensis* Dode extract, respectively) was used. The name and composition of each sample are described in the drawings.

Figure 8A:
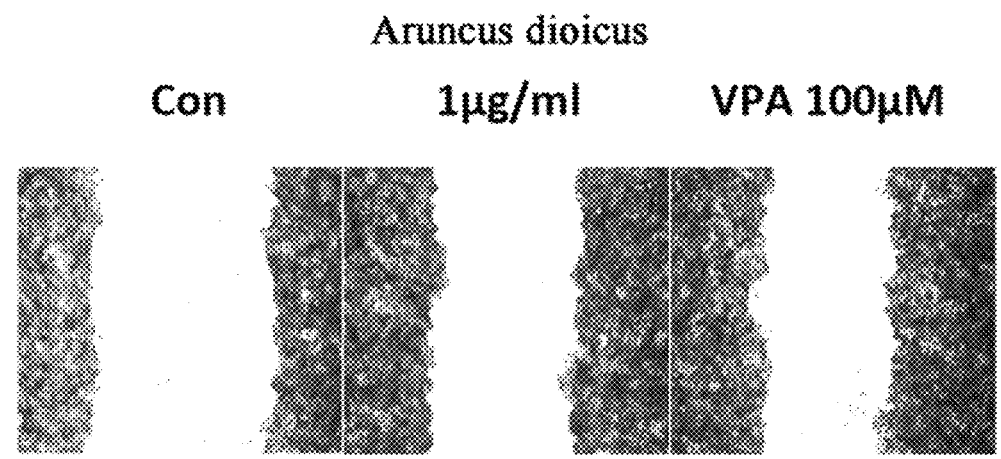
FIG. 8a shows a result of treating keratinocytes with a control group (con), an *Euodia sutchuenensis* Dode extract prepared in Example 8 (1 μg/mL) (*Euodia sutchuenensis* Dode 1 μg/mL) or a positive control group (VPA 100 μM) and imaging cell motility 18 hours later.

FIG. 8a shows a result of treating the keratinocytes with the control group (con), the *Euodia sutchuenensis* Dode extract prepared in Example 8 (1 µg/mL) (*Euodia sutchuenensis* Dode 1 µg/mL) or the positive control group (VPA 100 µM) and imaging cell motility 18 hours later.

Figure 8B:
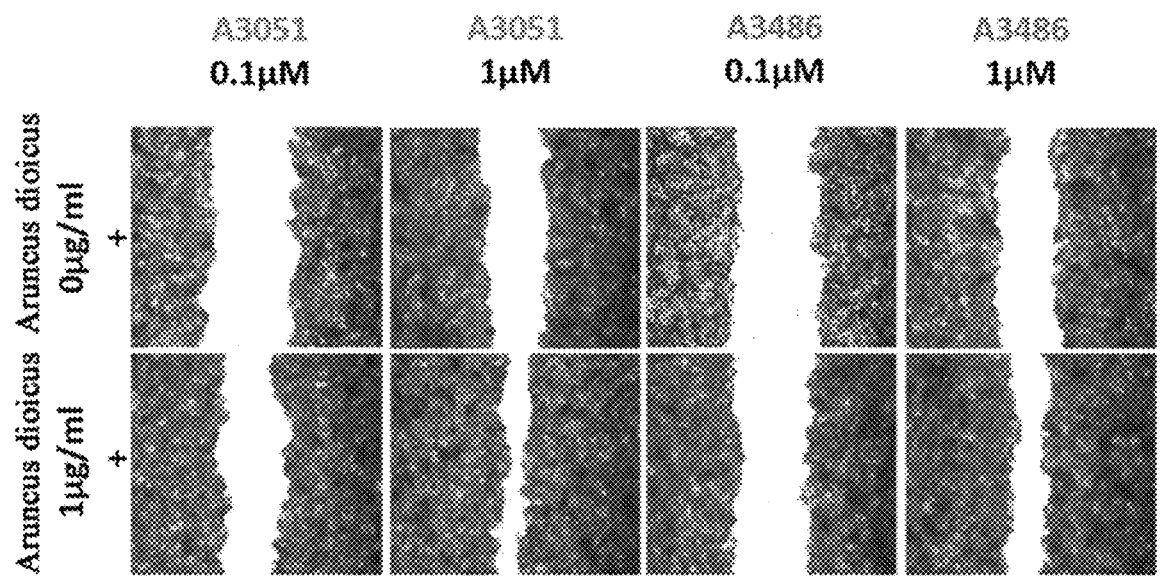
FIG. 8b shows a result of treating keratinocytes with an indirubin derivative of Example 1 (0.1 μM, 1 μM), an indirubin derivative of Example 2 (0.1 μM, 1 μM) or mixtures of Examples 12 and 13 (0.1 μM and 1 μM indirubin derivative mixed with 1 μg/mL *Euodia sutchuenensis* Dode extract, respectively) and imaging cell motility 18 hours later.
Figure 8C:
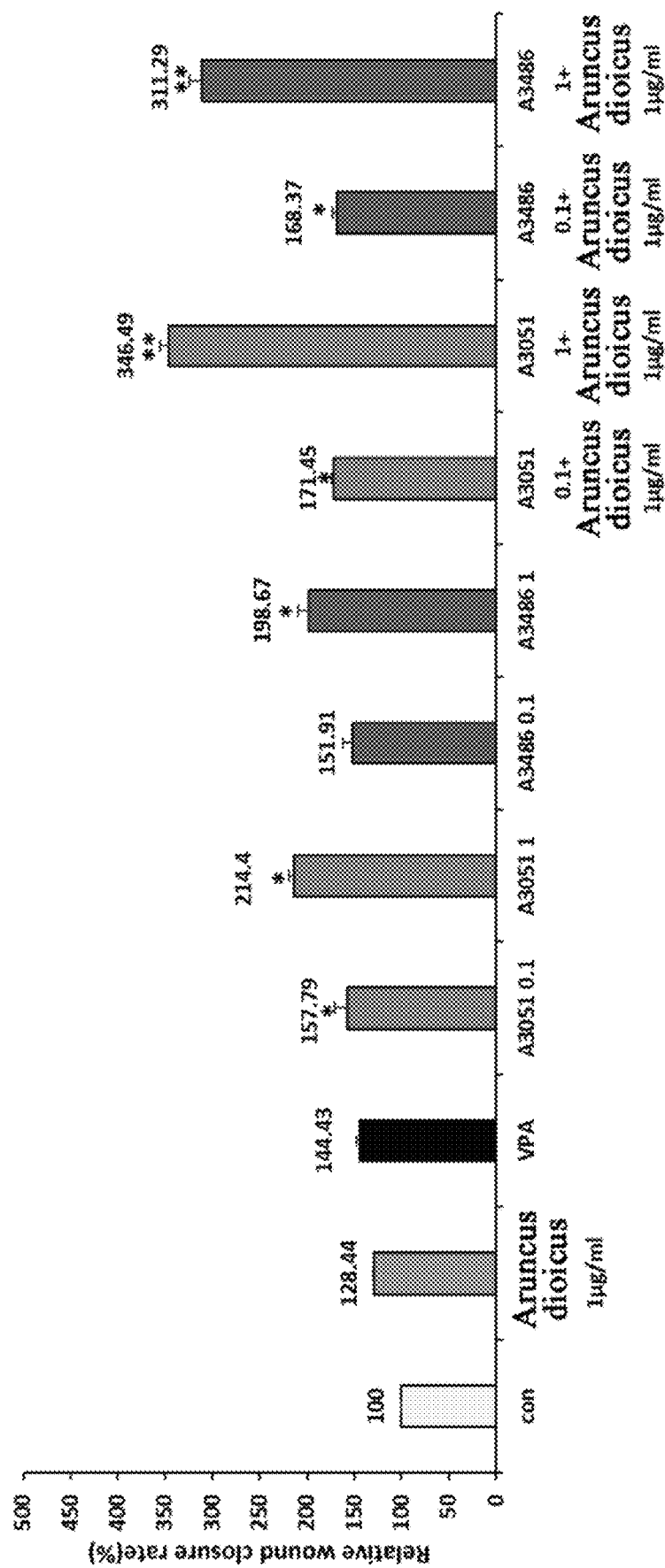
FIG. 8c shows a result of calculating cell motility from FIGS. 8a and 8b.

FIG. 8b shows a result of treating the keratinocytes with the indirubin derivative of Example 1 (0.1 µM, 1 µM), the indirubin derivative of Example 2 (0.1 µM, 1 µM) or the mixtures of Examples 12 and 13 (0.1 µM and 1 µM indirubin derivative mixed with 1 µg/mL *Euodia sutchuenensis* Dode extract, respectively) and imaging cell motility 18 hours later. FIG. 8c shows a result of calculating cell motility from FIGS. 8a and 8b.

Figure 8D:
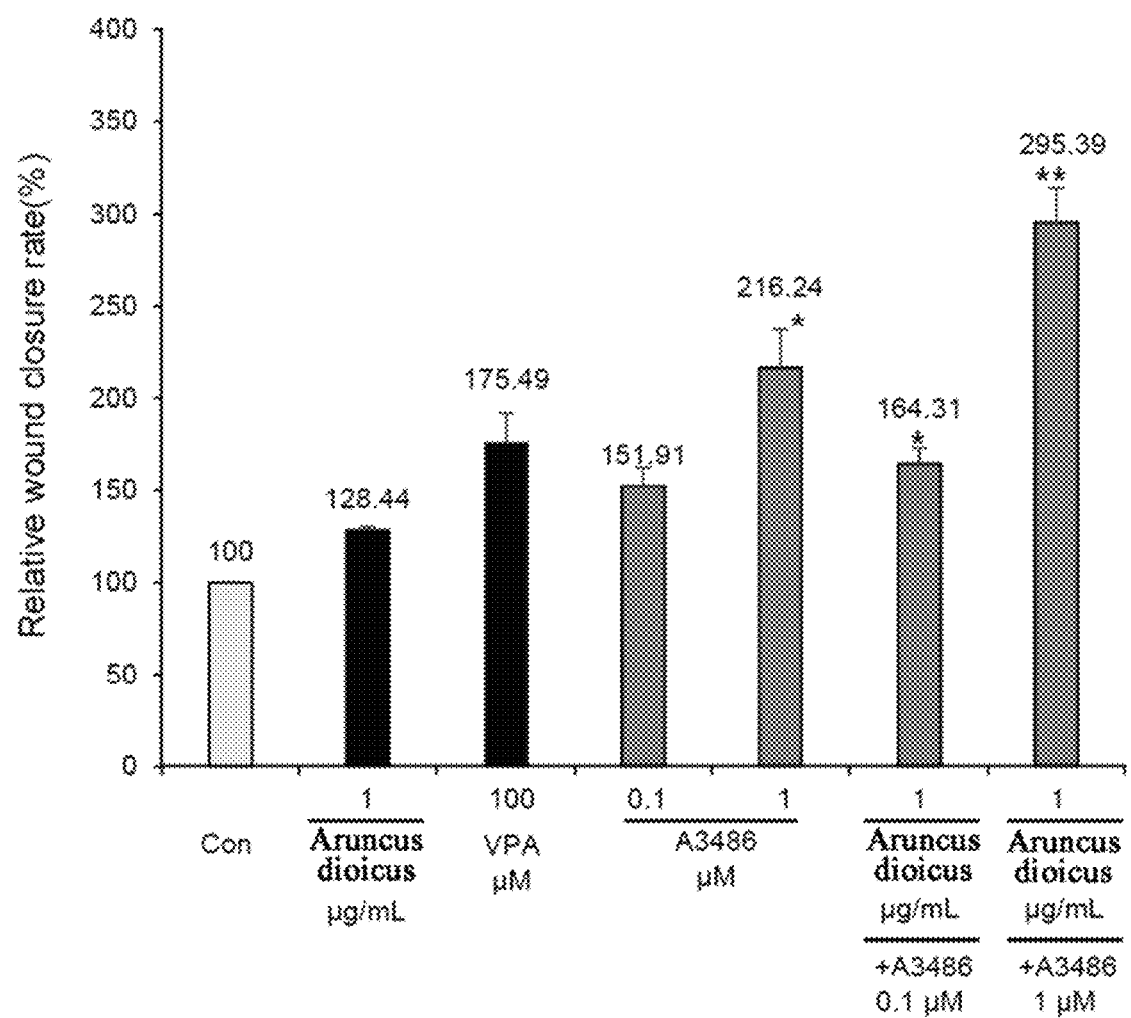
FIG. 8d shows a result of treating keratinocytes with an indirubin derivative of Example 3 (0.1 μM, 1 μM), a mixture of Example 14 (0.1 μM and 1 μM indirubin derivative mixed with 1 μg/mL *Euodia sutchuenensis* Dode extract, respectively) or an *Euodia sutchuenensis* Dode extract of Example 8 (*Euodia sutchuenensis* Dode) and calculating cell motility 18 hours later.

FIG. 8d shows a result of treating the keratinocytes with the indirubin derivative of Example 3 (0.1 µM, 1 µM), the mixture of Example 14 (0.1 µM and 1 µM indirubin derivative mixed with 1 µg/mL *Euodia sutchuenensis* Dode extract, respectively) or the *Euodia sutchuenensis* Dode extract of Example 8 (*Euodia sutchuenensis* Dode) and calculating cell motility 18 hours later.

The treatment with the *Euodia sutchuenensis* Dode extract alone (Example 8) as shown in FIG. 8a or the treatment with the indirubin derivative alone (*Euodia sutchuenensis* Dode 0 µg/mL) as shown in FIG. 8b showed no difference in cell motility from the control group (con). This can also be confirmed from the cell migration rate shows in FIGS. 8c and 8d.

Meanwhile, the mixtures of various ratios prepared in Examples 12, 13 and 14 according to the present disclosure showed significant recovery in cell motility, about 2 times or more as compared to the single treatments.

In particular, the recovery of cell migration rate (%) as compared to the control group was 28% for the single treatment with the *Euodia sutchuenensis* Dode extract and 50% and 114%, respectively, for the single treatments with the A3051 indirubin derivative. In contrast, it was increased to 71% and 246% for the treatment with the mixture of Example 12 and to 34-126% for the treatment with the mixture of Example 14, about 1.5-2 times higher than the sum for the treatment with the *Euodia sutchuenensis* Dode extract and the treatment with the indirubin derivative. That is to say, it can be seen that the composition for treating wound of the present disclosure exhibits an unexpectedly remarkable effect as compared to when the *Euodia sutchuenensis* Dode extract or the indirubin derivative is used alone, beyond the beyond the simple sum of the effects obtained from the respective compositions.

Test Example 6. Investigation of Wound Healing Effect of Mixture of *Euodia sutchuenensis* Dode Extract and Indirubin Derivative Through Animal Experiments Wound healing-promoting effect was investigated after treating an animal model with the indirubin derivative of Example 1 (0.5 mM), the indirubin derivative of Example 2 (0.5 mM) or the mixtures of Examples 12 and 13 (0.5 mM indirubin derivative mixed with 1 µg/mL *Euodia sutchuenensis* Dode extract).

The hair on the back of 7-week-old C3H mouse that entered the resting period was removed and a 1.5×1.5 cm² wound was made on the hair-removed region. A sample was applied to a positive control group, once daily for 12 days. After measuring wound size of the experimental animal on days 0 and 12, the wound tissue was fixed by immersing in 4% paraformaldehyde, embedded in paraffin and then sliced into 4 µm thickness. The sliced tissue was deparaffinized, rehydrated and then the degree of re-epithelialization was compared. Masson's trichrome staining and Picrosirius red staining were conducted for evaluation of the degree of collagen synthesis. For Masson's trichrome staining, a slide was immersed in Weigert's iron hematoxylin solution for 10 minutes and in Biebrich scarlet-acid fuchsin and aniline blue for 5 minutes each. For Picrosirius red staining, a slide was placed in Weigert's solution for 8 minutes and in Picrosirius red for 1 hour. β-Catenin, PCNA, keratin 14 and collagen I are important markers associated with wound healing. The sliced skin tissue was fluorescence-stained using β-catenin, PCNA, keratin 14 and collagen I antibodies and was observed using a fluorescence microscope (FIG. 9a).

The indirubin derivative of Example 1 (0.5 mM), the indirubin derivative of Example 2 (0.5 mM), the mixtures of Examples 12 and 13 (0.5 mM indirubin derivative mixed with 1 mg/mL *Euodia sutchuenensis* Dode extract), the *Euodia sutchuenensis* Dode extract of Example 8 (1 mg/mL) (*Euodia sutchuenensis* Dode 1 mg/mL), 100 µM EGF as a positive control group or 500 mM VPA (valproic acid) were used as samples. The control group (con) was treated with a sample-free solution, the control group (con1) was treated with water only and the control group (con2) was treated with 10% DMSO, 45% ethanol, 18% propylene glycol and 27% water.

Figure 9A:
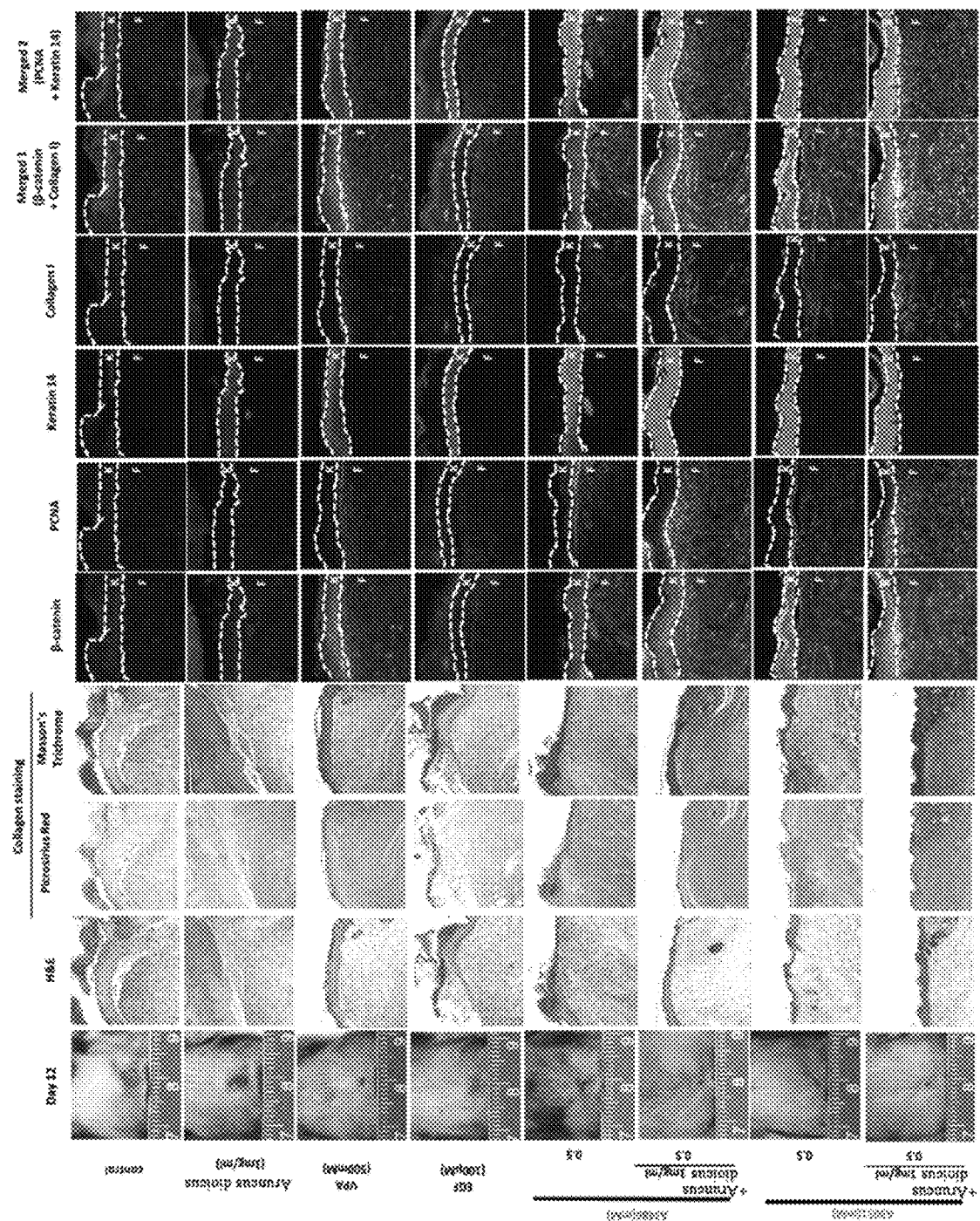
FIG. 9a shows a result of imaging and staining mouse acute wound tissue treated with an indirubin derivative of Example 1 (0.5 mM), an indirubin derivative of Example 2 (0.5 mM), mixtures of Examples 12 and 13, a control group (con), an *Euodia sutchuenensis* Dode extract of Example 8 (*Euodia sutchuenensis* Dode) or a positive control group (EGF and VPA) at different times (days 0 and 12).

FIG. 9a shows a result of imaging and staining the mouse acute wound tissue treated with the indirubin derivative of Example 1 (0.5 mM), the indirubin derivative of Example 2 (0.5 mM), the mixtures of Examples 12 and 13, the control group (con), the *Euodia sutchuenensis* Dode extract of Example 8 (*Euodia sutchuenensis* Dode) or the positive control group (EGF and VPA) at different times (days 0 and 12).

Figure 9B:
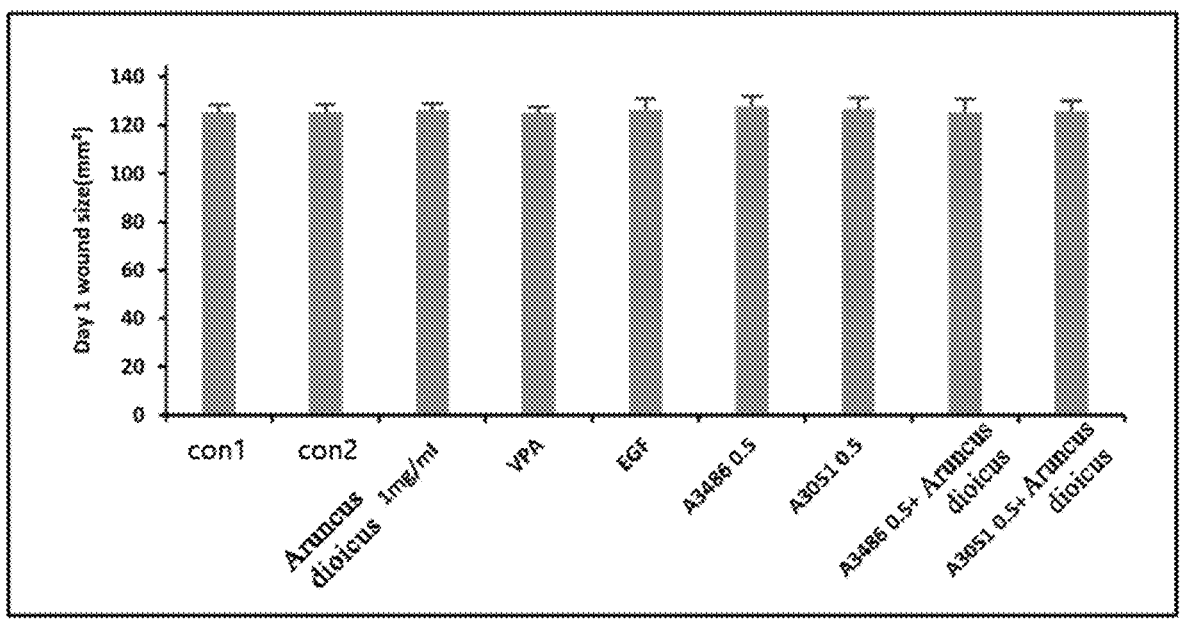
FIG. 9b shows a result of measuring the wound size ($mm^2$) of the mouse acute wound of each group in FIG. 9a on day 1.
Figure 9C:
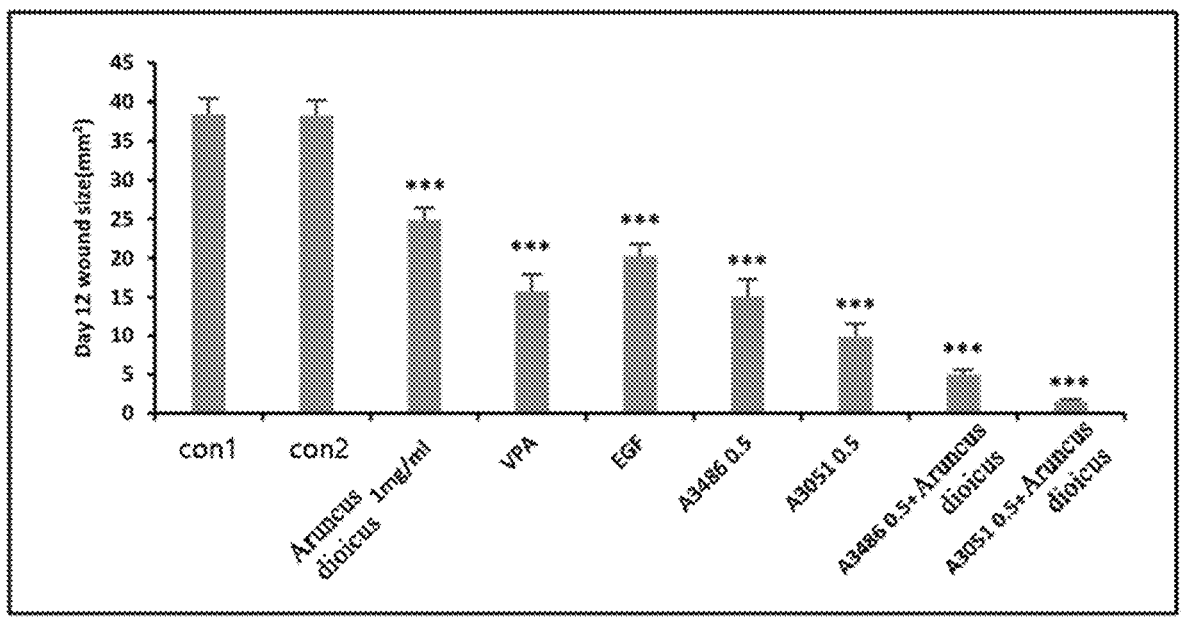
FIG. 9c shows a result of measuring the wound size ($mm^2$) of the mouse acute wound of each group in FIG. 9a on day 12.

FIG. 9b shows a result of measuring the wound size (mm²) of the mouse acute wound of each group in FIG. 9a on day 1, and FIG. 9c shows a result of measuring the wound size (mm²) of the mouse acute wound of each group in FIG. 9a on day 12.

In the drawings, the name and content of each sample treated to the wound site of the experimental animal are marked. For example, the indirubin derivative of Example 2 (0.5 mM) is marked by A3051 0.5 mM, the mixture of Example 13 by A3051 (0.5 mM)+*Euodia sutchuenensis* Dode 1 mg/mL, EGF (100 µM), VPA (500 mM), etc.

As shown in FIG. 9, it was confirmed that the treatment with the indirubin derivative alone resulted in a similar degree of wound repair as compared to the positive control group (EGF, VPA).

In contrast, as shown in FIG. 9, the mixtures of Examples 12 and 13 resulted in significant recovery in wound size as compared to the control group and the positive control group.

In addition, there was little difference the treatment with the *Euodia sutchuenensis* Dode extract of Example 8 alone and the control group (con) in the expression of β-catenin, PCNA, keratin 14 and collagen I or collagen investigated by Picrosirius red staining and Masson's trichrome staining. Meanwhile, the expression of β-catenin, PCNA, keratin 14 and collagen I was confirmed for treatment with the indirubin derivatives of Examples 1 and 2 alone, as compared to the control group (con). But, the expression level was slightly lower as compared to the positive control group.

In contrast, the acute wound tissue treated with the mixtures of the indirubin derivative and the *Euodia sutchuenensis* Dode extract of the same concentration of Example 12 and 13 showed remarkably increased expression of β-catenin, PCNA, keratin 14 and collagen I as compared to the positive control group, and also showed a remarkably superior result in collagen staining by Picrosirius red and Masson's trichrome. That is to say, it was confirmed that the mixtures of Example 12 and 13 increase the expression of β-catenin, PCNA, keratin 14 and collagen I and allow clean and uniform repair of the epidermal layer of skin without remaining scars such as lump, recess, etc. during healing, as compared to the positive control group.

It was confirmed that the mixtures of Example 12 and 13, prepared by mixing the *Euodia sutchuenensis* Dode extract which exhibited no effect on the expression of β-catenin, PCNA, keratin 14 and collagen I, and the indirubin derivative of Examples 1 and 2, which exhibited a slight effect, improved the expression of the various factors affecting scarring and wound healing. It is thought that, although the *Euodia sutchuenensis* Dode extract exhibits no effect in itself, it exhibits improved effect when used in combination with the indirubin derivative.

Test Example 7. Preparation of Diabetes-Induced Animal Model 3-week-old male C57BL/6N mice (Koatech, South Korea) were used. After accustoming the mice for a week to normal feed, high-fat diet (Product Data—D12492; 60% kcal, hereinafter referred to as HFD) was given for 4 weeks. Then, a diabetes-induced animal model was prepared by intraperitoneally injecting 40 mg/kg streptozocin (Sigma) once daily for a week. The mice were kept in cages maintained at constant temperature (22±2° C.) and relative humidity (40-60%) with light/dark cycles of 12/12 hours.

A non-diabetes-induced normal control group was given normal chow diet (Product Data—D12450B; 10% kcal, hereinafter referred to as NCD) for 4 weeks. Then, 40 mg/kg citrate buffer (pH 4.5) was intraperitoneally injected once daily for a week.

Blood glucose level was measured for 2 weeks in order to investigate whether diabetes was induced properly in the diabetes-induced animal model. Whereas the blood glucose level of the normal control group was 160-250 mg/dL, the blood glucose level of the diabetes-induced animal model was maintained at 300 mg/dL or higher.

Test Example 8. Wound Healing Effect in Diabetic Wound Animal Model 6 mice of the normal control group and 6 mice per test group of the diabetes-induced animal model of Test Example 7 were prepared. The hair on the back was removed and a 1.5×1.5 cm² wound was made on the hair-removed region.

Figure 10:
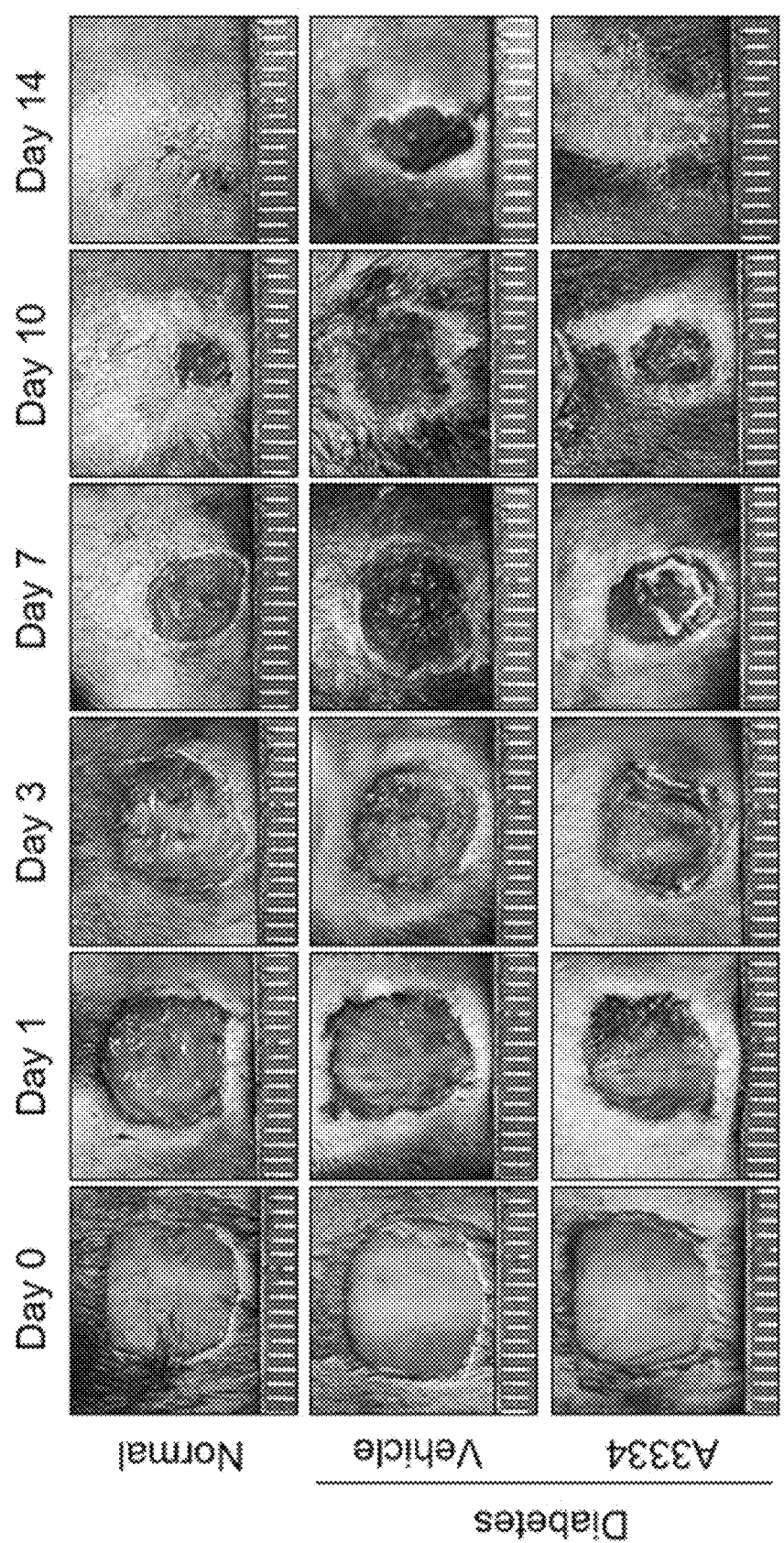
FIG. 10 shows a result of imaging the wound site of a normal control group, a negative control group and a test group in a diabetic animal model at different times.

For the normal control group, only 20 µL of an emulsion solution (Kollipore®EL:Tween 80:PEG 400 at a mixing weight ratio of 80:6:14) was applied to the wound site once daily for 14 days. For the negative control group, only 20 µL of the emulsion solution (Kollipore®EL:Tween 80:PEG 400 at a mixing weight ratio of 80:6:14) was applied to the wound site once daily for 14 days. For the test group, 20 µL of A3334 (Example 1) was applied to the wound site once daily for 14 days. Then, the wound site of the animal model was photographed and the wound area was measured on days 0, 1, 3, 7, 10 and 14 (FIG. 10). On day 14, after euthanizing the mouse with carbon dioxide, the wound site tissue was harvested and the histological structure was observed.

A3334 (Example 1) was prepared by preparing an emulsion solution by mixing Kollipore®EL:Tween 80:PEG 400 at a mixing weight ratio of 80:6:14 and then dissolving the A3334 indirubin derivative synthesized in Example 1 to a concentration of 0.5 mM.

TABLE 1

| Group | Administration | n |
|---|---|---|
| Normal control group (normal) | NCD for 4 weeks + intraperitoneal administration of 40 mg/kg citrate buffer (pH 4.5) once daily for a week + application of 20 µL of emulsion solution once daily for 2 weeks | 6 |
| Negative control group (vehicle) | HFD for 4 weeks + intraperitoneal administration of 40 mg/kg streptozocin once daily for a week + application of 20 µL of emulsion solution once daily for 2 weeks | 6 |
| Test group (A3334) | HFD for 4 weeks + intraperitoneal administration of 40 mg/kg streptozocin once daily for a week + application of 20 µL of A3334 (Example 1) once daily for 2 weeks | 6 |

Figure 11:
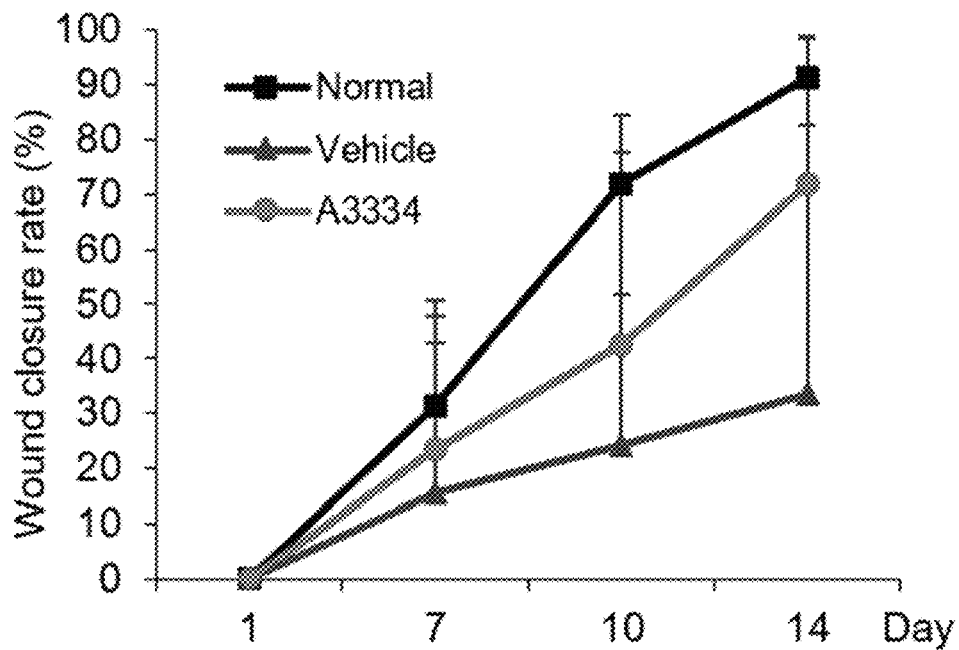
FIG. 11 shows a result of measuring wound closure rate (%) from the area of the wound site of a normal control group, a negative control group and a test group in a diabetic animal model at different times.

FIG. 10 shows a result of imaging the wound site of the normal control group, the negative control group and the test group in a diabetic animal model at different times, and FIG. 11 shows a result of measuring wound closure rate (%) from the area of the wound site of the normal control group, the negative control group and the test group in a diabetic animal model at different times.

The wound closure rate (%) was calculated according to Equation 1.

Wound closure rate (%)=[initial wound area on day 0−wound area on measurement day]/[initial wound area on day 0]×100   [Equation 1]

As shown in FIGS. 10 and 11, in the normal control group with no diabetes induced, the wound healed normally within 14 days. However, in the diabetes-induced negative control group, the wound did not heal until 14 days and about 60-70% of the wound site remained. In contrast, in the mouse to which A3334 (Example 1) was administered, the healing of the wound site was promoted similarly to the normal control group.

Figure 12:
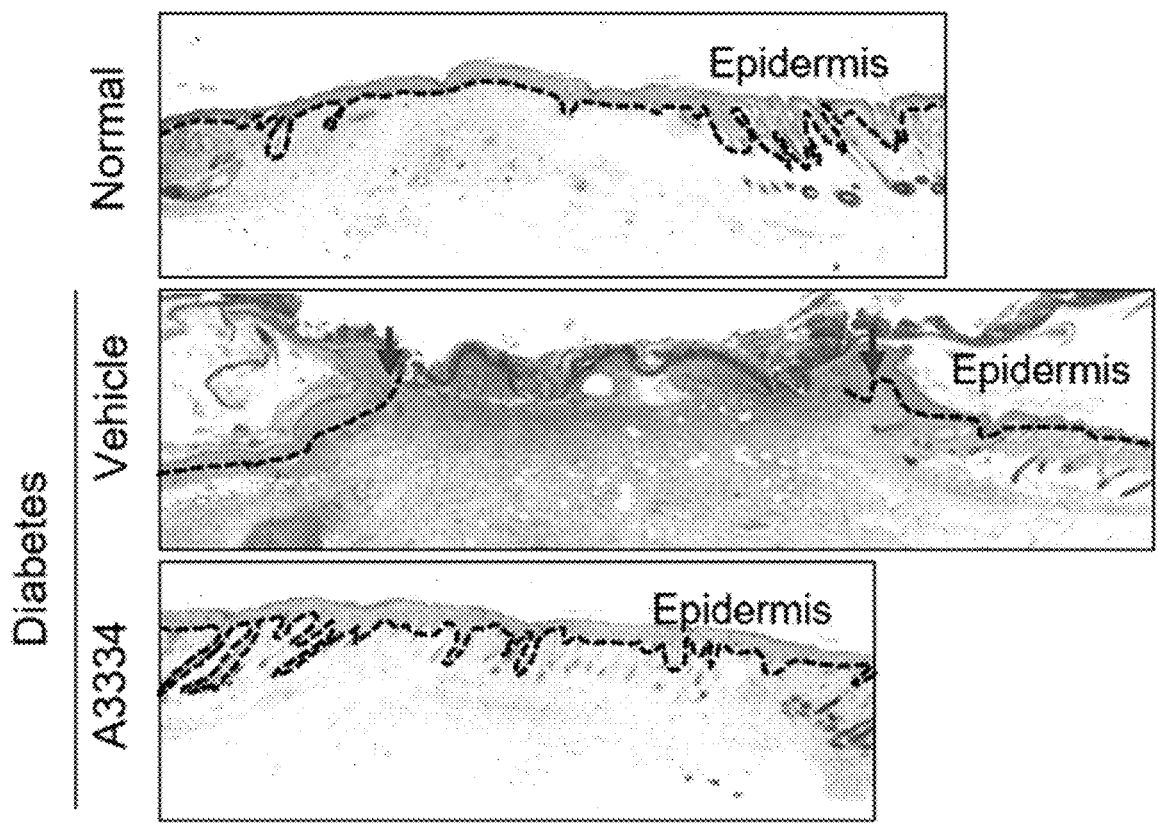
FIG. 12 shows H&E images obtained by staining the wound site tissue of a normal control group, a negative control group and a test group from a diabetic animal model with hematoxylin (purple) and eosin (pink).

FIG. 12 shows H&E images obtained by staining the wound site tissue of the normal control group, the negative control group and the test group from a diabetic animal model with hematoxylin (purple) and eosin (pink). Specifically, the wound site tissue obtained from the normal control group, the negative control group or the test group was fixed by immersing in 4% paraformaldehyde, embedded in paraffin and then sliced into 4 µm thickness. The sliced tissue was deparaffinized, rehydrated and then stained with hematoxylin (purple) and eosin (pink) for observation of histological structure.

It was confirmed that the most superior effect of improving wound healing was achieved when A3334 (Example 1) was applied. Whereas the negative control group, which is a diabetes-induced animal model, did not show re-epithelialization even after 14 days, the group to which A3334 (Example 1) was applied showed fast re-epithelialization despite the fact that diabetes was induced.

Figure 13:
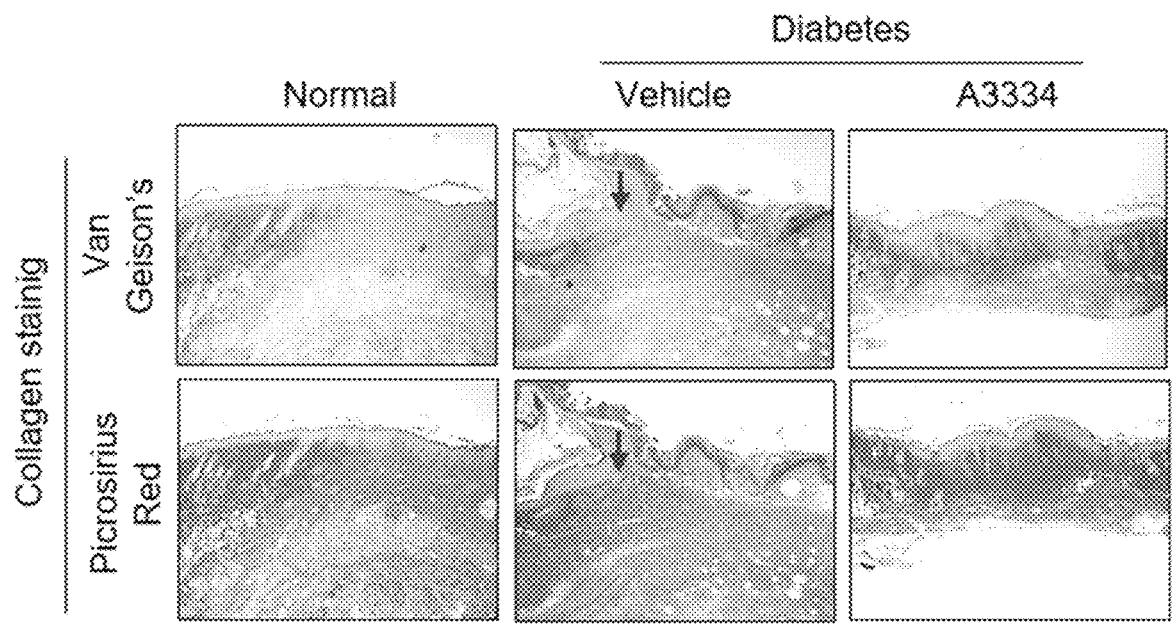
FIG. 13 shows images obtained by staining the wound site tissue of a normal control group, a negative control group and a test group from a diabetic animal model with Van Gieson's stain and Picrosirius red for evaluation of the degree of collagen synthesis.

FIG. 13 shows images obtained by staining the wound site tissue of the normal control group, the negative control group and the test group from a diabetic animal model with Van Gieson's stain and Picrosirius red for evaluation of the degree of collagen synthesis. Specifically, the wound site tissue obtained from the normal control group, the negative control group or the test group was fixed by immersing in 4% paraformaldehyde, embedded in paraffin and then sliced into 4 µm thickness. The sliced tissue was deparaffinized, rehydrated and then stained with Van Gieson's stain and Picrosirius red for observation of histological structure. For the Van Gieson's staining, the sliced tissue was immersed in Weigert's solution for 10 minutes and in picrofuchsin solution for 2 minutes. For the Picrosirius red staining, the sliced tissue was immersed in Weigert's solution for 8 minutes and in Picrosirius red for 1 hour.

As shown in FIG. 13, it was confirmed that A3334 (Example 1) increased collagen synthesis more than the normal control group (normal) and the negative control group (vehicle).

Test Example 9. Effect of Treating Diabetic Wound 6 mice of the normal control group and 6 mice per test group of the diabetes-induced animal model of Test Example 7 were prepared. The hair on the back was removed and a 0.8×0.8 cm² wound was made on the hair-removed region.

For the normal control group, only 20 µL of an emulsion solution (Kollipore®EL:Tween 80:PEG 400 at a mixing weight ratio of 80:6:14) was applied to the wound site once daily for 14 days. For the negative control group, only 20 µL of the emulsion solution (Kollipore®EL:Tween 80:PEG 400 at a mixing weight ratio of 80:6:14) was applied to the wound site once daily for 14 days. For the positive control group (VPA), 20 µL of a composition prepared by mixing 500 mM VPA in an emulsion solution was applied to the wound site once daily for 14 days.

Figure 14:
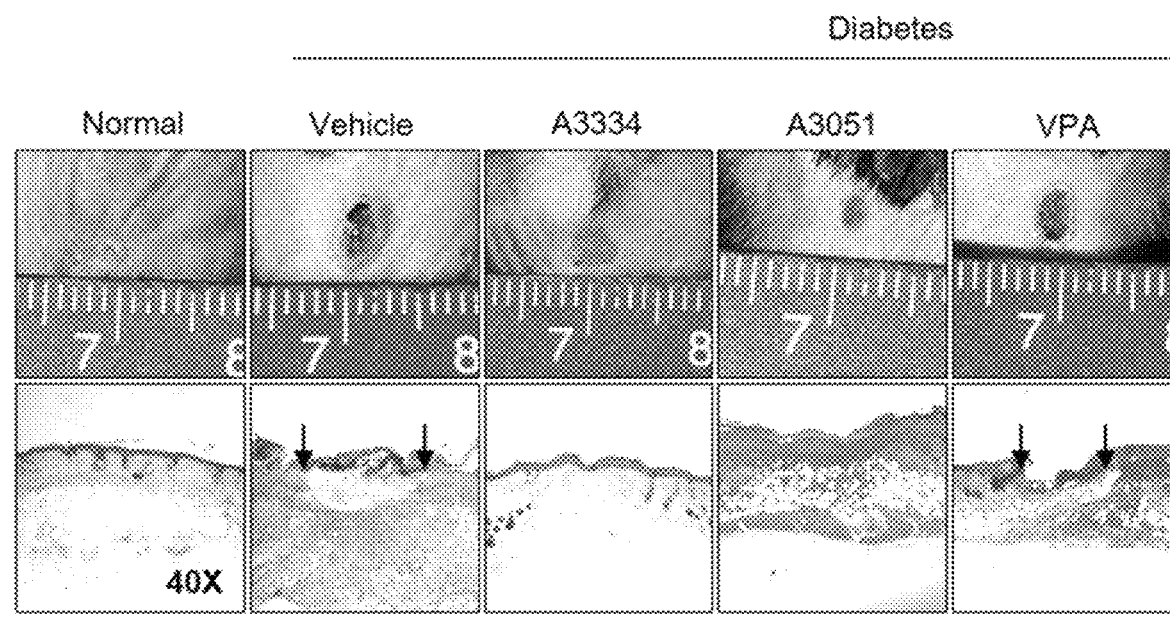
FIG. 14 shows H&E images obtained by staining the wound site tissue of a normal control group, a negative control group, a positive control group and first and second test groups from a diabetic animal model on day 14 with hematoxylin (purple) and eosin (pink).

For the first test group, 20 µL of A3334 (Example 1) was applied to the wound site once daily for 14 days. For the second test group, 20 µL of A3051 (Example 2) was applied to the wound site once daily for 14 days. Then, the wound site of each group was photographed and the wound area was measured (FIG. 14). On day 14, after euthanizing the mouse with carbon dioxide, the wound site tissue was harvested and the histological structure was observed.

TABLE 2

| Group | Administration | n |
|---|---|---|
| Normal control group (normal) | NCD for 4 weeks + intraperitoneal administration of 40 mg/kg citrate buffer (pH 4.5) once daily for a week + application of 20 µL of emulsion solution once daily for 2 weeks | 6 |

TABLE 2-continued

| Group | Administration | n |
|---|---|---|
| Negative control group (vehicle) | HFD for 4 weeks + intraperitoneal administration of 40 mg/kg streptozocin once daily for a week + application of 20 μL of emulsion solution once daily for 2 weeks | 6 |
| Positive control group (VPA) | HFD for 4 weeks + intraperitoneal administration of 40 mg/kg streptozocin once daily for a week + application of 20 μL of emulsion solution + 500 mM VPA once daily for 2 weeks | 6 |
| First test group (A3334) | HFD for 4 weeks + intraperitoneal administration of 40 mg/kg streptozocin once daily for a week + application of 20 μL of A3334 (Example 1) once daily for 2 weeks | 6 |
| Second test group (A3051) | HFD for 4 weeks + intraperitoneal administration of 40 mg/kg streptozocin once daily for a week + application of 20 μL of A3051 (Example 2) once daily for 2 weeks | 6 |

FIG. 14 shows H&E images obtained by staining the wound site tissue of the normal control group, the negative control group, the positive control group and first and second test groups from a diabetic animal model on day 14 with hematoxylin (purple) and eosin (pink).

Specifically, the wound site tissue obtained from the normal control group, the negative control group, the positive control group or the first or second test group was fixed by immersing in 4% paraformaldehyde, embedded in paraffin and then sliced into 4 μm thickness. The sliced tissue was deparaffinized, rehydrated and then stained with hematoxylin (purple) and eosin (pink) for observation of histological structure.

As shown in FIG. 14, in the normal control group with no diabetes induced, the wound healed normally within 14 days. However, in the diabetes-induced negative control group, the wound did not heal until 14 days and about 70% of the wound site remained. When VPA (valproic acid), which is known to exhibit wound healing effect by activating the Wnt signaling pathway, was administered, wound healing was delayed similarly to the negative control group. However, when in the mice to which A3334 (Example 1) and A3051 (Example 2) were administered, the healing of the wound site was promoted similarly to the normal control group.

In addition, whereas re-epithelialization did not occur even after 14 days for the group treated with VPA or the negative control group, re-epithelialization occurred quickly when A3334 (Example 1) or A3051 (Example 2) was applied as in the normal control group despite the fact that diabetes was induced.

Figure 15:
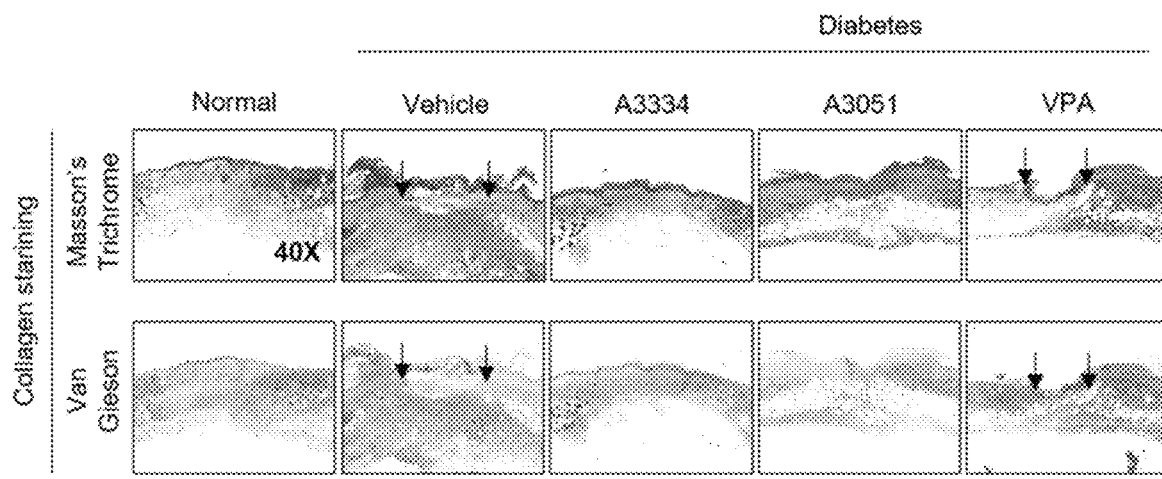
FIG. 15 shows images obtained by staining the wound site tissue of a normal control group, a negative control group and first and second test groups from a diabetic animal model with Van Gieson's stain and Masson's trichrome for evaluation of the degree of collagen synthesis.

FIG. 15 shows images obtained by staining the wound site tissue of the normal control group, the negative control group and the first and second test groups from a diabetic animal model with Van Gieson's stain and Masson's trichrome for evaluation of the degree of collagen synthesis. Specifically, the wound site tissue obtained from the normal control group, the negative control group, the positive control group or the first or second test group was fixed by immersing in 4% paraformaldehyde, embedded in paraffin and then sliced into 4 μm thickness. The sliced tissue was deparaffinized, rehydrated and then stained with Van Gieson's stain and Masson's trichrome for observation of histological structure. For the Van Gieson's staining, the sliced tissue was immersed in Weigert's solution for 10 minutes and in picrofuchsin solution for 2 minutes. For the Masson's trichrome staining, the sliced tissue was immersed in Weigert's iron hematoxylin solution for 10 minutes and in Biebrich scarlet-acid fuchsin and Aniline blue for 5 minutes each.

As shown in FIG. 15, it was confirmed that the A3334 (Example 1) and A3051 (Example 2) increased collagen synthesis more than the normal control group (normal), the negative control group (vehicle) and the positive control group (VPA).

Figure 16:
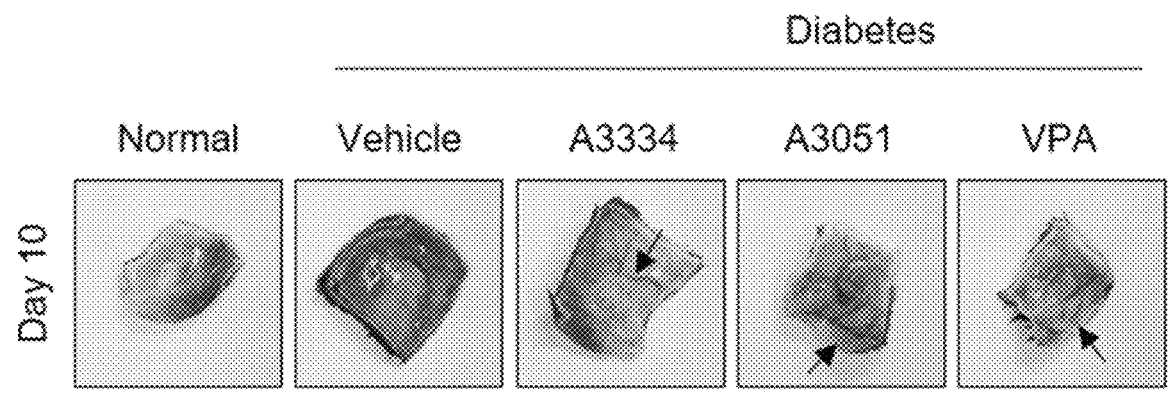
FIG. 16 shows a result of observing angiogenesis around the wound site of a normal control group, a negative control group, a positive control group and first and second test groups from a diabetic animal model.

FIG. 16 shows a result of observing angiogenesis around the wound site of the normal control group, the negative control group, the positive control group and the first and second test groups from a diabetic animal model. Specifically, the wound site tissue obtained from the normal control group, the negative control group, the positive control group or the first and second test groups was fixed by immersing in 4% paraformaldehyde and angiogenesis was observed.

As shown in FIG. 16, it was confirmed that the A3334 (Example 1) and A3051 (Example 2) increased angiogenesis unlike the normal control group (normal) or the negative control group (vehicle). Through this, it can be seen that since the A3334 (Example 1) and A3051 (Example 2) exhibit superior tissue regeneration effect through activation of collagen, α-SMA, etc. and exhibit superior effect of reducing wound healing time through activation of angiogenesis, as compared to the Wnt signaling pathway activator, VPA, they can provide better effect for diabetic wound as compared to the existing wound healing agent.

Test Example 10. Measurement of Solubility of Active Ingredient of the Present Disclosure For preparation of an emulsion solution, the solubility of the indirubin derivative of Example 2 was measured for various oils and surfactants. A sufficient amount of the indirubin derivative powder prepared in Example 2 was added to each oil or surfactant (1 mL) and then vortexed for 30 minutes. After shaking in a culture tank of 37° C. at 50 rpm for 72 hours until equilibrium was achieved, followed by centrifugation at 16,100×g for 5 minutes, the supernatant was diluted properly with methanol and then analyzed by LC/MS/MS. The oils or surfactants used, and the measured solubility are given in Table 3.

The Waters Xevo TQ MS-ACQUITY UPLC system was used for the analysis. An ACQUITY UPLC® BEH column (C18, 1.7 μm, 2.1×50 mm) was used and the analysis was made at room temperature. As a mobile phase, deionized distilled water containing 0.1% formic acid and acetonitrile containing 0.1% formic acid (30:70, v/v) were used after filtering through a 0.2-μm membrane filter. 0.5 μL of the sample was injected at a flow rate of 0.25 mL/min. The LC/MS/MS condition was: cone voltage=38 V; collision voltage=32 V; mother ion m/z=329; daughter ion m/z=229.

TABLE 3

| | | Solubility (mg/mL) |
|---|---|---|
| Oil | Olive oil | 0.83 |
| | Sunflower oil | 1.35 |
| | Kolliphor ® EL | 5.4 |
| Surfactant | Tween 20 | 4.58 |
| | Tween 80 | 4.92 |
| Co-surfactant | Transcutol P | 1.15 |
| | Propylene glycol | 0.25 |
| | PEG 400 | 3.1 |

Figure 17:
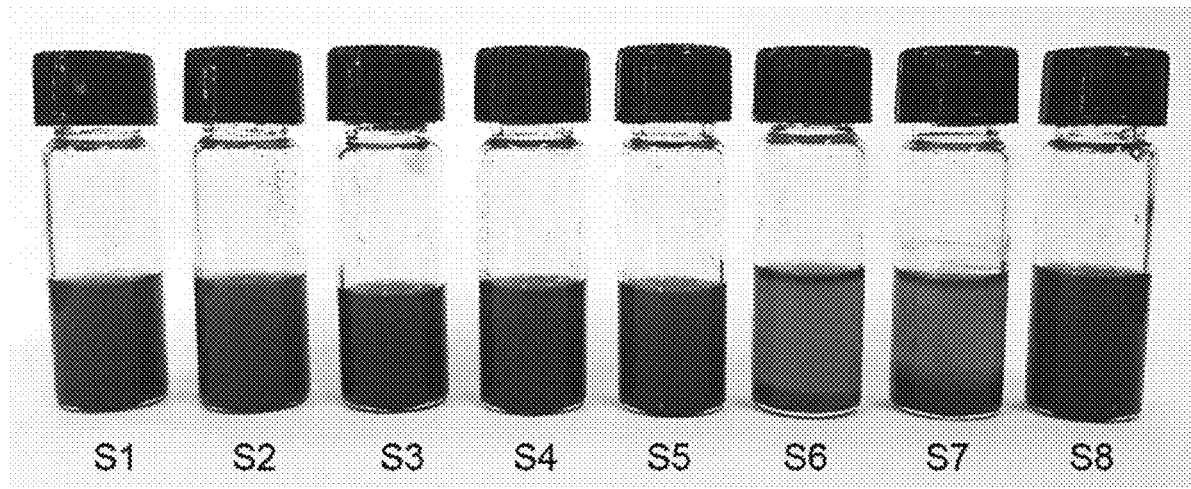
FIG. 17 shows emulsion solutions prepared by dissolving an indirubin derivative prepared in Example 2 of the present disclosure in various oils or surfactants.

FIG. 17 shows the emulsion solutions prepared by dissolving the indirubin derivative prepared in Example 2 of the present disclosure in various oils or surfactants. As shown in FIG. 17 and Table 3, the indirubin derivative prepared in Example 2 according to the present disclosure showed the highest solubility for Kolliphor® EL, Tween 20, Tween 80 and PEG 400. The Kolliphor® EL, Tween 20 or Tween 80 and PEG 400 are safe and unharmful to the human body, and they are used in various formulations, including formulations for dermal administration.

Test Example 11. Analysis of Ternary Phase Diagram

Based on the result of solubility test, Kolliphor® EL was selected as an oil phase of an emulsion solution, and a mixture of Tween 80 and PEG 400 was selected as a surfactant. In order to identify the region where an emulsion is formed therefrom, a ternary phase diagram was constructed at room temperature using the $H_2O$ titration method. After preparing surfactant mixtures of Tween 80 and PEG 400 at ratios of 1:1, 2:1 and 1:2, the surfactant was mixed with the oil phase, Kolliphor® EL, at various ratios (0.5:9.5, 1:9, 2:8, 3:7, 4:6, 5:5, 6:4, 7:3, 8:2, 9:1 and 9.5:0.5) to prepare emulsion solutions. While stirring the emulsion solution, water was dropped at a rate of 1 mL/min using an infusion pump and the region where a uniformly mixed state is maintained was marked in the phase diagram. The obtained ternary phase diagrams are shown in FIGS. 18a, 18b and 18c.

Figure 18A:
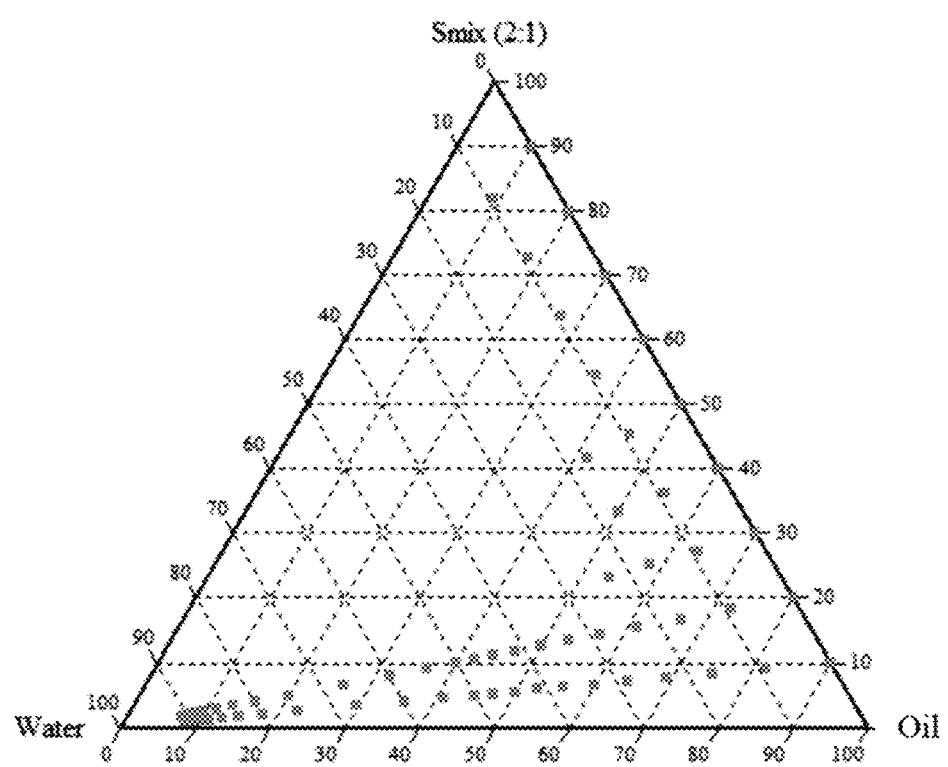
FIG. 18a is a ternary phase diagram for an emulsion solution prepared from a 2:1 surfactant mixture of Tween 80 and PEG 400.
Figure 18B:
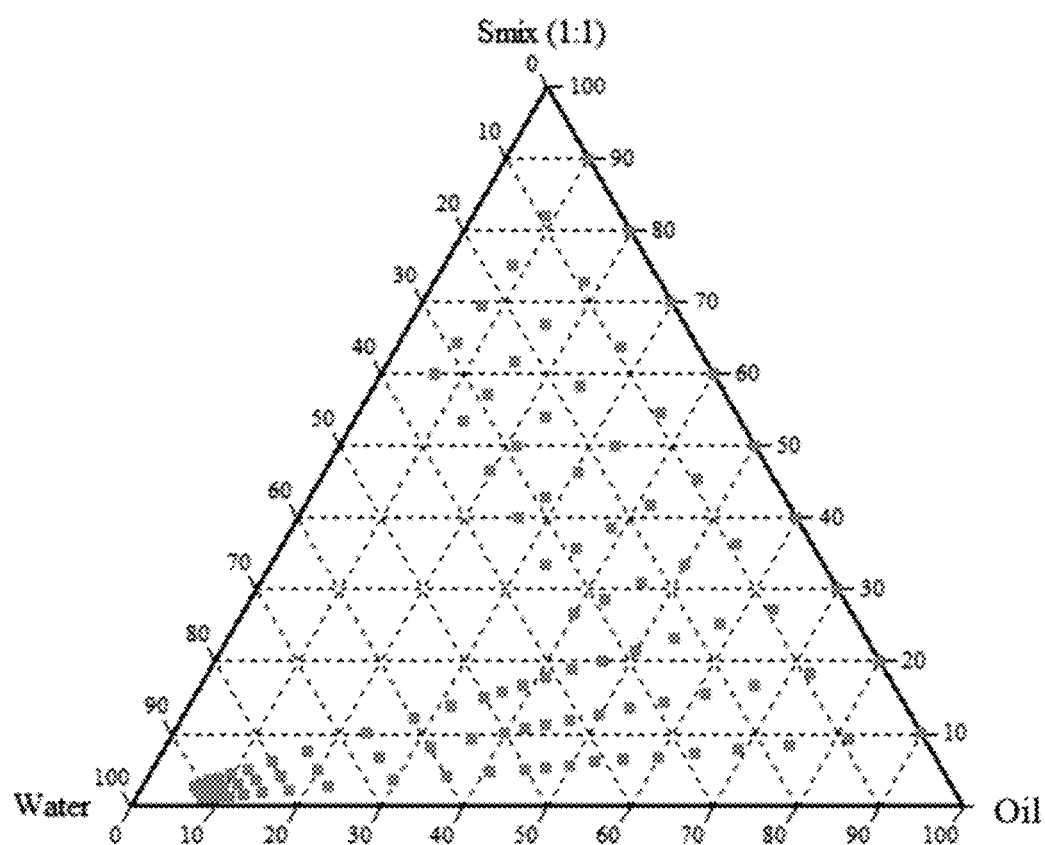
FIG. 18b is a ternary phase diagram for an emulsion solution prepared from a 1:1 surfactant mixture of Tween 80 and PEG 400.
Figure 18C:
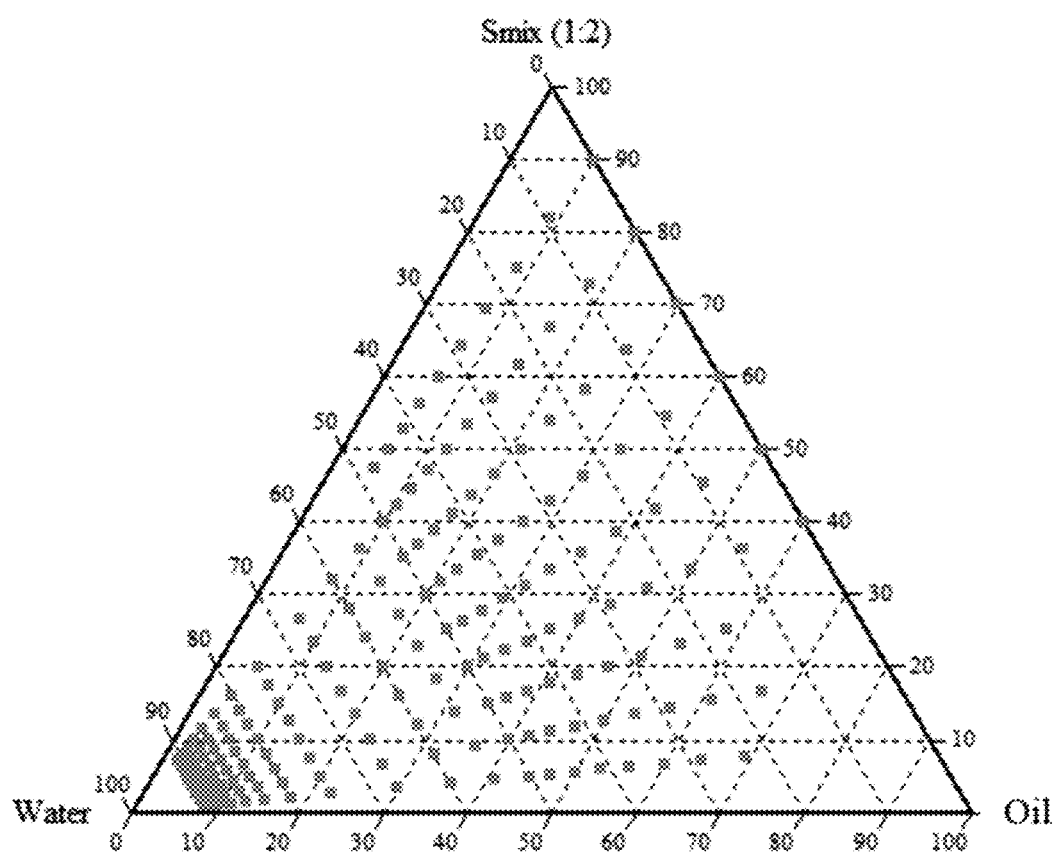
FIG. 18c is a ternary phase diagram for an emulsion solution prepared from a 1:2 surfactant mixture of Tween 80 and PEG 400. In the ternary phase diagrams of FIGS. 18a-18c, the regions where stable emulsions are formed are marked by red dots.

FIG. 18a is the ternary phase diagram for the emulsion solution prepared from a 2:1 surfactant mixture of Tween 80 and PEG 400, FIG. 18b is the ternary phase diagram for the emulsion solution prepared from a 1:1 surfactant mixture of Tween 80 and PEG 400, and FIG. 18c is the ternary phase diagram for the emulsion solution prepared from a 1:2 surfactant mixture of Tween 80 and PEG 400. In the ternary phase diagrams of FIGS. 18a-18c, the regions where stable emulsions are formed are marked by red dots.

As can be seen from FIGS. 18a, 18b and 18c, a surfactant mixture of Tween 80 and PEG 400 at a mixing weight ratio of 1:2, which showed the widest range, was selected for the emulsion solution. Then, in order to determine the ratio of the surfactant and the oil phase, the solubility, droplet size, viscosity and zeta-potential of emulsion solutions prepared with various ratios were compared.

Test Example 12. Development of Formulation of Pharmaceutical Composition for Preventing or Treating Wound In order to develop an oil-in-water emulsion formulation having appropriate solubility and long-term stability of the indirubin derivative prepared in Example 2, the most stable emulsion solution was selected by mixing a surfactant, a polyethylene glycol and an oil.

Various emulsion solutions were prepared from the surfactant, the polyethylene glycol and the oil selected in Test Example 11 at ratios of 10:30:60-90:3:7. An emulsion containing the active ingredient of the present disclosure (indirubin derivative of Example 2 powder) was prepared by adding the active ingredient such that the concentration was 10 wt % based on the total weight of the composition and then stirring overnight (for example, 20 g of the indirubin derivative powder prepared in Example 2 was mixed with 80 g of the emulsion solution to prepare a 100-g composition).

The composition could further contain a cyclodextrin as a solubilizer. In this test example, 100 parts by weight of a cyclodextrin was used based on 100 parts by weight of the indirubin derivative (active ingredient) for better solubilization of the indirubin derivative.

The prepared emulsion looked uniformly mixed and had opaque red color. A result of analyzing the solubility, droplet size, viscosity and zeta-potential of each emulsion is given in Table 4.

TABLE 4

| Emulsion solution (Kollipore ®EL:Tween 80:PEG 400) mixing weight ratio | Solubility (mg/mL) | Droplet size (nm) | Viscosity (mPas) | Zeta-potential (mV) |
|---|---|---|---|---|
| F1 | 10:30:60 | 2.99 | 1525.7 | 23.33 | −5.14 |
| F2 | 20:26:54 | 3.58 | 921.3 | 44.46 | −6.87 |
| F3 | 30:23:47 | 3.81 | 624.9 | 59.12 | −7.23 |
| F4 | 40:20:40 | 4.11 | 479.4 | 65.07 | −6.94 |
| F5 | 50:16:34 | 5.67 | 332.3 | 72.72 | −7.99 |
| F6 | 60:13:27 | 6.86 | 264.9 | 88.85 | −9.72 |
| F7 | 70:10:20 | 7.59 | 183.8 | 91.39 | −10.83 |
| F8 | 80:6:14 | 7.69 | 41.5 | 98.3 | −20.38 |
| F9 | 90:3:7 | 6.88 | 29.3 | 99.52 | −20.99 |

As shown in Table 4, the droplet size decreased as the oil content was increased. Although all the formulations had physical properties appropriate to be used as pharmaceutical and cosmetic compositions, F8 had the most preferred size, viscosity, zeta-potential and solubility.

Test Example 13. Evaluation of Stability of Emulsion 1

In order to evaluate the stability of emulsions, emulsions F8 and F10-F12 were prepared with the compositions described in Table 5 in the same manner as in Test Example 12. The stability of the emulsions was measured based on the change in relative solubility (%) at low temperature (4° C.) and room temperature (25° C.). The change in the relative solubility (%) until 3 months after the preparation is recorded in FIG. 19 and FIG. 20.

TABLE 5

| | Emulsion composition | | | Active (indirubin derivative of ingredient Example 2) | Solubilizer (2-hydroxy β-cyclodextrin) | Water phase |
|---|---|---|---|---|---|---|
| | Oil | Surfactant | Polyethylene glycol | | | |
| DMSO control | — | — | — | 12.5 g | 12.5 g | Distilled water 100 g |
| F8 | Kollipore ® EL 80 g | Tween 80 6.7 g | PEG 400 13.3 g | 12.5 g | 12.5 g | Distilled water 100 g |
| F10 | — | — | PEG 400 100 g | 12.5 g | 12.5 g | Distilled water 100 g |
| F11 | — | Tween 80 100 g | — | 12.5 g | 12.5 g | Distilled water 100 g |
| F12 | Kollipore ® EL 100 g | — | — | 12.5 g | 12.5 g | Distilled water 100 g |

Figure 19:
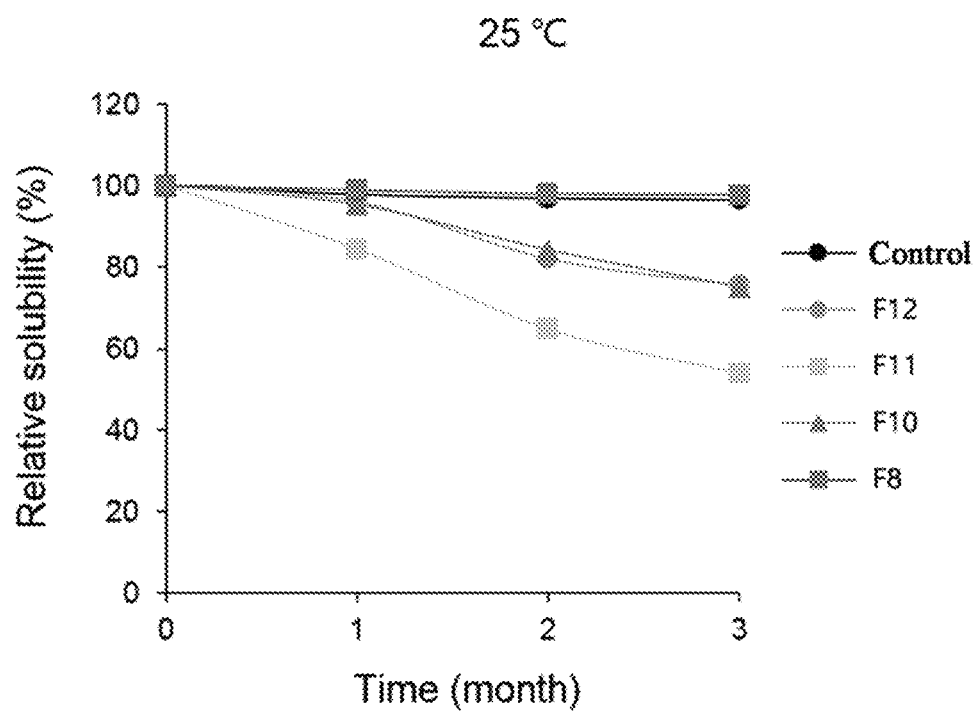
FIG. 19 shows a result of measuring the change in relative solubility (%) of emulsions F8 and F10-F12 at room temperature (25° C.).
Figure 20:
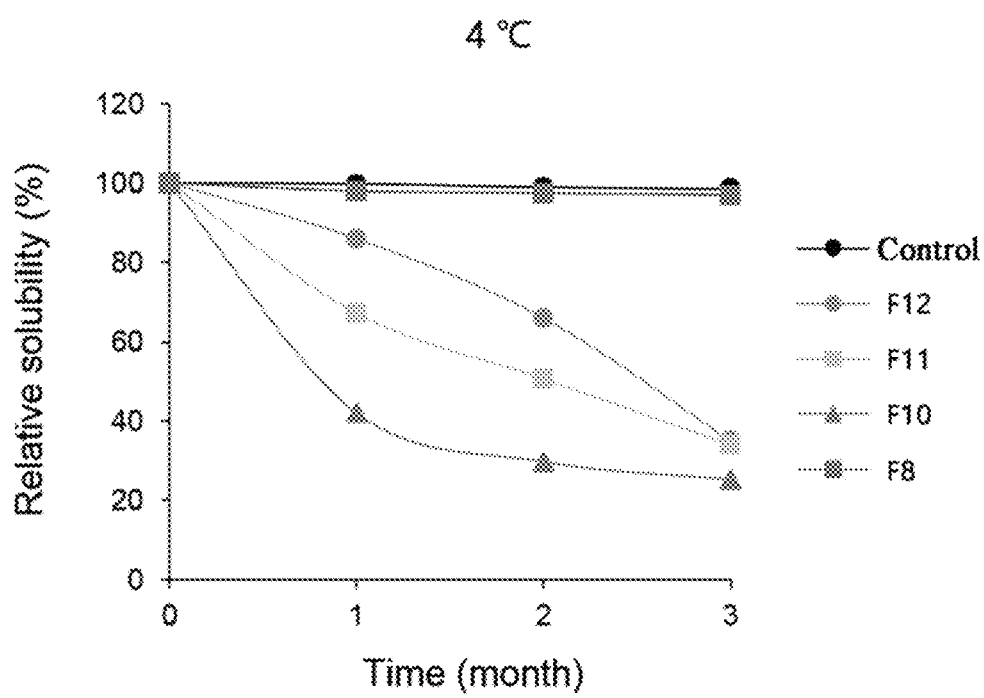
FIG. 20 shows a result of measuring the change in relative solubility (%) of emulsions F8 and F10-F12 at low temperature (4° C.).

FIG. 19 shows a result of measuring the change in relative solubility (%) of the emulsions F8 and F10-F12 at room temperature (25° C.), and FIG. 20 shows a result of measuring the change in relative solubility (%) of the emulsions F8 and F10-F12 at low temperature (4° C.).

As shown in FIGS. 19-20 and Table 5, as a result of monitoring the change in relative solubility after keeping at low temperature or room temperature for 3 months, the emulsion of the present disclosure (F8) did not show significant change in solubility % between immediately after the preparation and 3 months later. In contrast, the emulsions prepared with different compositions from the emulsion of the present disclosure (F12, F11 and F10) showed 40% or more change in solubility at low temperature and room temperature immediately after the preparation and 3 months later. In particular, it was confirmed that the solubility was decreased rapidly by 80% or more when stored at low temperature.

Test Example 14. Evaluation of Stability of Emulsion 2

In order to investigate whether the active ingredient of the indirubin derivative of Example 2 maintains activity stably in the emulsion, emulsions F8 and F10-F12 were prepared with the compositions described in Table 5 in the same manner as in Test Example 13. The stability of the activity of the indirubin derivative in the emulsions was measured based on the change in relative Wnt reporter activity (%) at low temperature (4° C.) and room temperature (25° C.). The change in the relative Wnt reporter activity (%) until 3 months after the preparation is recorded in FIGS. 21 and 22.

The Wnt reporter activity (%) was measured as follows. After treating HEKTOP reporter cells with the active ingredient prepared in the form of an emulsion, the Wnt reporter activity was measured 24 hours later.

Figure 21:
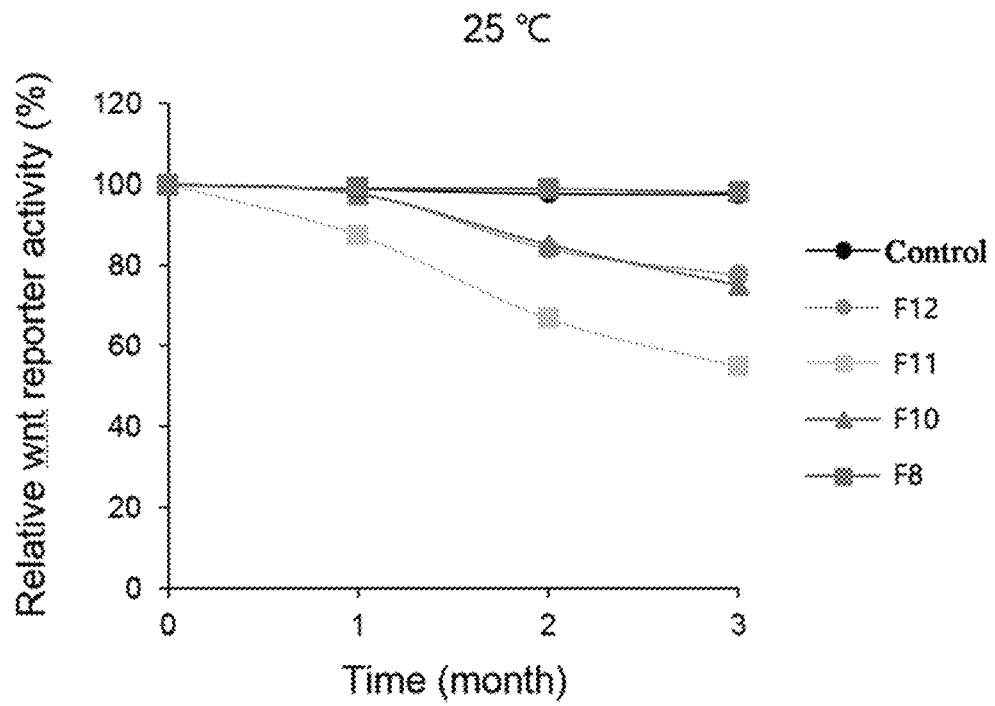
FIG. 21 shows a result of measuring the change in relative Wnt reporter activity (%) of emulsions F8 and F10-F12 at room temperature (25° C.).
Figure 22:
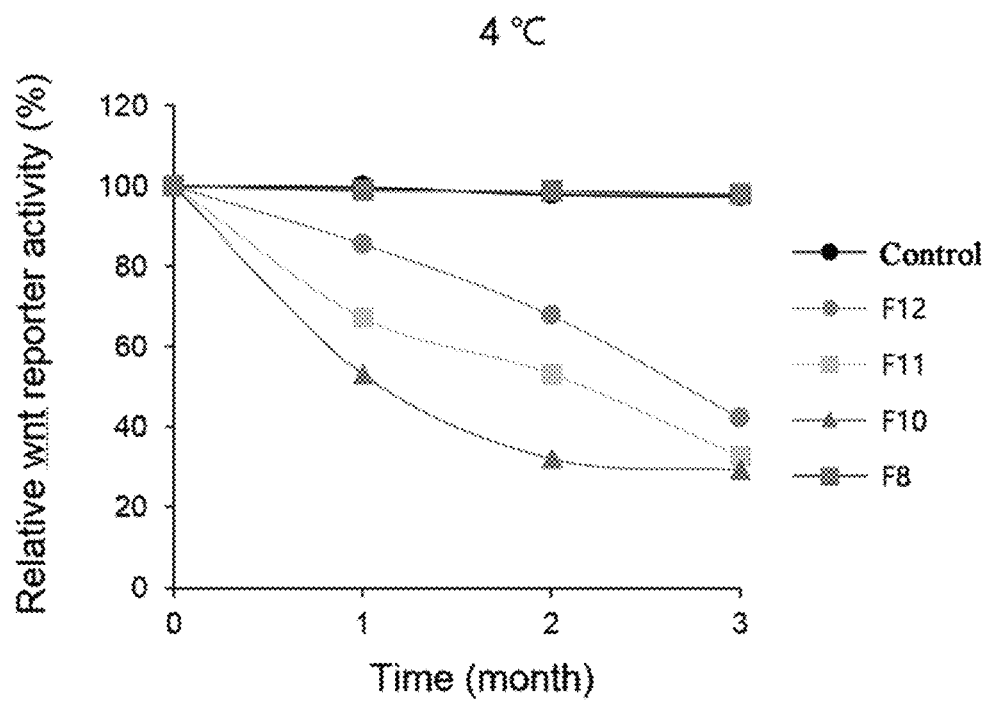
FIG. 22 shows a result of measuring the change in relative Wnt reporter activity (%) of emulsions F8 and F10-F12 at low temperature (4° C.).

FIG. 21 shows a result of measuring the change in the relative Wnt reporter activity (%) of the emulsions F8 and F10-F12 at room temperature (25° C.), and FIG. 22 shows a result of measuring the change in the relative Wnt reporter activity (%) of the emulsions F8 and F10-F12 at low temperature (4° C.).

As shown in FIGS. 21 and 22, as a result of monitoring the change in the relative Wnt reporter activity (%) at low temperature and room temperature for 3 months, the emulsion of the present disclosure (F8) did not show significant change in the Wnt reporter activity % between immediately after the preparation and 3 months later. In contrast, the emulsions prepared with different compositions from the emulsion of the present disclosure (F12, F11 and F10) showed 40% or more decrease in the Wnt reporter activity at low temperature and room temperature immediately after the preparation and 3 months later. In particular, it was confirmed that the solubility was decreased rapidly by 80% or more when stored at low temperature.

Preparation Example 1: Cream-Type Cosmetic Composition for Preventing or Treating Wound A cream-type cosmetic composition for preventing or treating wound, which contains a mixture of one or more indirubin derivative selected from Chemical Formulas 1-4 as an active ingredient, was prepared. The cream-type cosmetic composition was prepared by mixing ingredients including one or more indirubin derivative selected from Chemical Formulas 1-4 as described below.

| One or more indirubin derivative selected from Chemical Formulas 1-4 | 4.0 wt % |
|---|---|
| Glycerin | 2.0 wt % |
| Paraben | 0.2 wt % |
| Allantoin | 2.0 wt % |
| Betaine | 3.0 wt % |
| Sodium hyaluronate | 1.0 wt % |
| Tocopherol acetate | 5.0 wt % |
| Shea butter | 2.0 wt % |
| Trehalose | 1.0 wt % |
| Antiseptic and fragrance | Adequate |
| Purified water | To 100 wt % |
| Total | 100 wt % |

Preparation Example 2: Pharmaceutical Composition for Preventing or Treating Wound (Ointment)

A pharmaceutical composition for preventing or treating wound (ointment), which contains a mixture of one or more indirubin derivative selected from Chemical Formulas 1-4 as an active ingredient, was prepared. The pharmaceutical composition for preventing or treating wound (ointment) was prepared by mixing ingredients including one or more indirubin derivative selected from Chemical Formulas 1-4 as described below.

| One or more indirubin derivative selected from Chemical Formulas 1-4 | 10 wt % |
|---|---|
| Diethyl sebacate | 8 wt % |
| Spermaceti | 5 wt % |
| Polyoxyethylene oleyl ether phosphate | 6 wt % |
| Sodium benzoate | Adequate |
| Vaseline | To 100 wt % |
| Total | 100 wt % |

Preparation Example 3: Application to Milk

| Milk | 99.9 wt % |
|---|---|
| One or more indirubin derivative selected from Chemical Formulas 1-4 | 0.1 wt % |

Preparation Example 4: Application to Beverage

| One or more indirubin derivative selected from Chemical Formulas 1-4 | 10 mg |
|---|---|
| Potassium lactate | 50 mg |
| Citric acid | 5 mg |
| Nicotinamide | 10 mg |
| Riboflavin sodium hydrochloride | 3 mg |
| Pyridoxine hydrochloride | 2 mg |
| Arginine | 10 mg |
| Sucrose fatty acid ester | 10 mg |
| Water | 200 mL |

The invention claimed is:

1. A method of treating wound, comprising:
administering to a subject at least one therapeutically effective dose of a composition comprising one or more indirubin derivatives selected from Chemical Formulas 1-4 as an active ingredient:

[Chemical Formula 1]

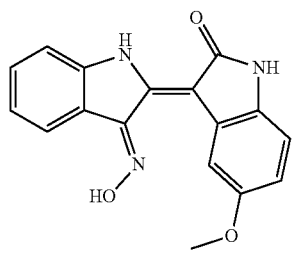

[Chemical Formula 2]

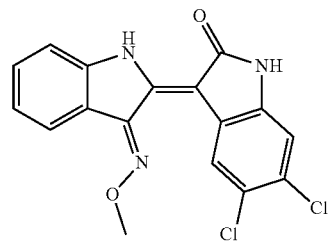

[Chemical Formula 3]

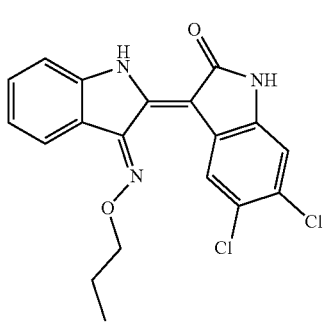

[Chemical Formula 4]

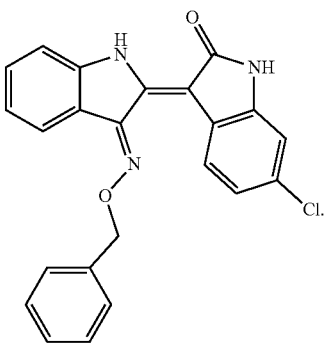

2. The method according to claim 1, wherein the composition further comprises an *Euodia sutchuenensis* Dode extract.

3. The method according to claim 1, wherein the composition further comprises one or more compounds selected from a group consisting of methyl vanillate, hesperidin and quercitrin.

4. The method according to claim 1, wherein the wound is caused by burn, ulcer, injury, surgical operation, childbirth, chronic wound, diabetic wound or dermatitis.

5. The method according to claim 1, wherein the composition is for topical application to skin.

6. The method according to claim 1, wherein the composition is prepared into a formulation selected from a group consisting of a cream, a gel, an ointment, an emulsion, a suspension, a spray and a transdermal patch.

7. The method according to claim 1, wherein the composition is an emulsion formulation further comprising an oil, a surfactant and a polyethylene glycol.

8. The method according to claim 7, wherein a mixing weight ratio of the oil, the surfactant and the polyethylene glycol is 0.3-30:1:2-2.5.

9. The method according to claim 1, wherein the active ingredient is comprised in an amount of 1-20 wt % based on the total weight of the composition.

10. The method according to claim 7, wherein the surfactant is one or more selected from the group consisting of polyoxyethylene sorbitan monolaurate, polyoxyethylene sorbitan monopalmitate, polyoxyethylene sorbitan monostearate and polyoxyethylene sorbitan oleate.

11. The method according to claim 7, wherein the oil is one or more selected from the group consisting of polyethoxylated castor oil, sunflower oil and olive oil.

12. The method according to claim 7, wherein the composition further comprises a cyclodextrin and the cyclodextrin is comprised in an amount of 100-1000 parts by weight based on 100 parts by weight of the active ingredient present in the composition.

13. The method according to claim 7, wherein the emulsion formulation is a stable formulation not exhibiting change in Wnt activity and solubility in distilled water at 4-25° C. for 3 months.

* * * * *